US012562591B2

(12) United States Patent
Lynch et al.

(10) Patent No.: US 12,562,591 B2
(45) Date of Patent: Feb. 24, 2026

(54) AUTOCLAVABLE CONTAINER FOR STERILIZING A WIRELESSLY CHARGEABLE BATTERY

(71) Applicant: Stryker Corporation, Kalamazoo, MI (US)

(72) Inventors: Robert E. Lynch, Portage, MI (US); Daniel Reichert, Climax, MI (US); Patrick Hooper, Portage, MI (US); Gerard Mouatt, Portage, MI (US); Burton C. Judson, Kalamazoo, MI (US); David E. Hershberger, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 902 days.

(21) Appl. No.: 17/598,072

(22) PCT Filed: Mar. 27, 2020

(86) PCT No.: PCT/US2020/025429
§ 371 (c)(1),
(2) Date: Sep. 24, 2021

(87) PCT Pub. No.: WO2020/198666
PCT Pub. Date: Oct. 1, 2020

(65) Prior Publication Data
US 2022/0224154 A1     Jul. 14, 2022

Related U.S. Application Data

(60) Provisional application No. 62/965,614, filed on Jan. 24, 2020, provisional application No. 62/824,780, filed on Mar. 27, 2019.

(51) Int. Cl.
*H02J 50/00*     (2016.01)
*A61L 2/07*     (2006.01)
(Continued)

(52) U.S. Cl.
CPC .............. *H02J 50/005* (2020.01); *A61L 2/07* (2013.01); *A61L 2/202* (2013.01); *A61L 2/206* (2013.01);
(Continued)

(58) Field of Classification Search
CPC ... A61L 2/07; A61L 2/20; A61L 2/202; A61L 2/206; A61L 2/208; A61L 2/26;
(Continued)

(56) References Cited

U.S. PATENT DOCUMENTS

| | | |
|---|---|---|
| 645,576 A | 3/1900 | Trower et al. |
| 3,861,873 A | 1/1975 | MacFarlane et al. |

(Continued)

FOREIGN PATENT DOCUMENTS

| | | |
|---|---|---|
| DE | 10109358 C1 | 11/2002 |
| DE | 202012102803 U1 | 10/2013 |

(Continued)

OTHER PUBLICATIONS

English language abstract for JPH 02-142562 A extracted from espacenet.com database on Jan. 29, 2024, 2 pages.

(Continued)

*Primary Examiner* — Timothy C Cleveland
(74) *Attorney, Agent, or Firm* — Howard & Howard Attorneys PLLC

(57)     ABSTRACT

An autoclavable container for sterilizing a wirelessly chargeable battery is disclosed. The autoclavable container includes a lid including metal and a base including a material permitting the transmission of an electromagnetic wave therethrough and having a glass transition temperature above 140 degrees Celsius. The lid defines a plurality of apertures configured to allow a sterilant to permeate the lid. The lid includes a mount configured to receive a filter defining a microbial barrier. The base defines a plurality of (Continued)

receptacles, each receptacle shaped to receive a wirelessly chargeable battery. The base also includes a plurality of protrusions, each protrusion being aligned with a corresponding receptacle.

11 Claims, 38 Drawing Sheets

(51) Int. Cl.

| | |
|---|---|
| *A61L 2/202* | (2026.01) |
| *A61L 2/206* | (2026.01) |
| *A61L 2/208* | (2026.01) |
| *A61L 2/26* | (2006.01) |
| *H02J 7/00* | (2006.01) |
| *H02J 50/10* | (2016.01) |

(52) U.S. Cl.
CPC .............. *A61L 2/208* (2013.01); *A61L 2/26* (2013.01); *H02J 7/0045* (2013.01); *H02J 50/10* (2016.02); *A61L 2202/122* (2013.01); *A61L 2202/14* (2013.01)

(58) Field of Classification Search
CPC ........... A61L 2202/122; A61L 2202/14; A61L 2202/182; H02J 50/005; H02J 50/10; H02J 7/0045
See application file for complete search history.

(56) References Cited

U.S. PATENT DOCUMENTS

| | | | |
|---|---|---|---|
| 4,617,178 A | 10/1986 | Nichols | |
| 4,641,076 A | 2/1987 | Linden | |
| 4,783,321 A | 11/1988 | Spence | |
| 4,986,414 A | 1/1991 | Ashley et al. | |
| 5,183,643 A | 2/1993 | Nichols | |
| 5,225,767 A | 7/1993 | Gulczynski | |
| 5,407,069 A | 4/1995 | Schmieding et al. | |
| 5,455,466 A | 10/1995 | Parks et al. | |
| 5,720,930 A | 2/1998 | Bean | |
| 5,734,254 A | 3/1998 | Stephens | |
| 5,744,933 A | 4/1998 | Inoue et al. | |
| 5,952,814 A | 9/1999 | Van Lerberghe | |
| 6,018,227 A | 1/2000 | Kumar et al. | |
| 6,077,485 A | 6/2000 | Baker | |
| 6,118,249 A | 9/2000 | Brockmann et al. | |
| 6,184,651 B1 | 2/2001 | Fernandez et al. | |
| 6,184,655 B1 | 2/2001 | Malackowski | |
| 6,301,128 B1 | 10/2001 | Jang et al. | |
| 6,379,631 B1 | 4/2002 | Wu | |
| 6,439,625 B1 | 8/2002 | Schainholz et al. | |
| 6,605,922 B2 | 8/2003 | Tamai et al. | |
| 6,844,702 B2 | 1/2005 | Giannopoulos et al. | |
| 6,847,190 B2 | 1/2005 | Schaefer et al. | |
| 7,501,198 B2 | 3/2009 | Barlev et al. | |
| 7,705,559 B2 | 4/2010 | Powell et al. | |
| 7,948,208 B2 | 5/2011 | Partovi et al. | |
| 8,169,185 B2 | 5/2012 | Partovi et al. | |
| 8,183,827 B2 | 5/2012 | Lyon | |
| 8,258,745 B2 | 9/2012 | Smith et al. | |
| 8,278,873 B2 | 10/2012 | Smith et al. | |
| 8,344,690 B2 | 1/2013 | Smith et al. | |
| 8,344,691 B2 | 1/2013 | Smith et al. | |
| 8,418,872 B2 | 4/2013 | Smith | |
| 8,431,153 B2 | 4/2013 | Shukla | |
| 8,432,293 B2 | 4/2013 | Symons | |
| 8,519,668 B2 | 8/2013 | Hui | |
| 8,567,048 B2 | 10/2013 | Singh et al. | |
| 8,590,724 B2 | 11/2013 | Kreidler et al. | |
| 8,629,652 B2 | 1/2014 | Partovi et al. | |
| 8,638,062 B2 | 1/2014 | Baarman et al. | |
| 8,803,475 B2 | 8/2014 | Smith et al. | |
| 8,808,283 B2 | 8/2014 | Moua et al. | |
| 8,890,470 B2 | 11/2014 | Partovi | |
| 8,901,779 B2 | 12/2014 | Kesler et al. | |
| 8,947,047 B2 | 2/2015 | Partovi et al. | |
| 9,000,720 B2 | 4/2015 | Stulen et al. | |
| 9,024,576 B2 | 5/2015 | Maenpaa | |
| 9,106,203 B2 | 8/2015 | Kesler et al. | |
| 9,124,121 B2 | 9/2015 | Ben-Shalom et al. | |
| 9,131,034 B2 | 9/2015 | Ma et al. | |
| 9,136,729 B2 | 9/2015 | Ashinghurst et al. | |
| 9,142,989 B2 | 9/2015 | Fell et al. | |
| 9,143,003 B2 | 9/2015 | Baarman et al. | |
| 9,178,369 B2 | 11/2015 | Partovi | |
| 9,178,569 B2 | 11/2015 | Chakravarty et al. | |
| 9,276,437 B2 | 3/2016 | Partovi et al. | |
| 9,301,718 B2 | 4/2016 | Lin | |
| 9,327,041 B2 | 5/2016 | Hawkes | |
| 9,364,288 B2 | 6/2016 | Smith et al. | |
| 9,381,058 B2 | 7/2016 | Houser et al. | |
| 9,472,966 B2 | 10/2016 | Frushour et al. | |
| 9,554,411 B1 | 1/2017 | Hall et al. | |
| 9,583,803 B2 | 2/2017 | Miller et al. | |
| 9,590,446 B2 | 3/2017 | Park et al. | |
| 9,597,143 B2 | 3/2017 | Madan et al. | |
| 9,667,091 B2 | 5/2017 | Baek et al. | |
| 9,680,335 B2 | 6/2017 | Kang et al. | |
| 9,711,999 B2 | 7/2017 | Hietala et al. | |
| 9,722,447 B2 | 8/2017 | Partovi | |
| 9,837,862 B2 | 12/2017 | Sherman et al. | |
| 9,842,686 B2 | 12/2017 | Peterson et al. | |
| 9,872,723 B2 | 1/2018 | Smith | |
| 9,924,815 B2 | 3/2018 | Canty | |
| 9,929,584 B2 | 3/2018 | Aghassian et al. | |
| 9,941,590 B2 | 4/2018 | Luzinski et al. | |
| 9,948,128 B2 | 4/2018 | Ashinghurst et al. | |
| 10,056,790 B2 | 8/2018 | Miller et al. | |
| 10,063,105 B2 | 8/2018 | Leabman | |
| 10,111,710 B2 | 10/2018 | Lober | |
| 10,115,520 B2 | 10/2018 | Partovi | |
| 10,236,709 B2 * | 3/2019 | Decker ................... H02J 50/00 |
| 10,250,066 B2 | 4/2019 | Jankins et al. | |
| 10,284,023 B2 | 5/2019 | Kim et al. | |
| 10,312,722 B2 | 6/2019 | Decker et al. | |
| 10,396,606 B2 | 8/2019 | Hall et al. | |
| 10,468,904 B2 | 11/2019 | Decker et al. | |
| 10,485,889 B2 | 11/2019 | Kusano et al. | |
| 11,316,371 B1 | 4/2022 | Partovi et al. | |
| 2003/0102842 A1 | 6/2003 | Tamai et al. | |
| 2004/0145342 A1 | 7/2004 | Lyon | |
| 2005/0139599 A1 | 6/2005 | Schainholz et al. | |
| 2007/0048176 A1 | 3/2007 | Orrico | |
| 2007/0090788 A1 | 4/2007 | Hansford et al. | |
| 2010/0154353 A1 | 6/2010 | Cesa et al. | |
| 2011/0279226 A1 | 11/2011 | Chen et al. | |
| 2012/0116380 A1 | 5/2012 | Madan et al. | |
| 2012/0116381 A1 | 5/2012 | Houser et al. | |
| 2013/0300204 A1 | 11/2013 | Partovi | |
| 2014/0074185 A1 | 3/2014 | Fell et al. | |
| 2014/0079589 A1 | 3/2014 | Landgrebe et al. | |
| 2014/0132210 A1 | 5/2014 | Partovi | |
| 2014/0276665 A1 | 9/2014 | Lopez et al. | |
| 2014/0327390 A1 | 11/2014 | Park et al. | |
| 2014/0347233 A1 | 11/2014 | Mahanfar et al. | |
| 2014/0350545 A1 | 11/2014 | Moua et al. | |
| 2015/0088115 A1 | 3/2015 | Smith | |
| 2015/0102681 A1 | 4/2015 | Leabman et al. | |
| 2015/0180284 A1 | 6/2015 | Kang et al. | |
| 2015/0326059 A1 | 11/2015 | Abu Qahouq | |
| 2015/0365136 A1 | 12/2015 | Miller et al. | |
| 2016/0079800 A1 | 3/2016 | Ashinghurst et al. | |
| 2016/0087483 A1 | 3/2016 | Hietala et al. | |
| 2016/0111886 A1 | 4/2016 | Sherman et al. | |
| 2016/0126771 A1 | 5/2016 | Aghassian et al. | |
| 2016/0134140 A1 | 5/2016 | Tittle et al. | |
| 2016/0181854 A1 | 6/2016 | Leabman | |
| 2016/0190856 A1 | 6/2016 | Baek et al. | |
| 2016/0192989 A1 | 7/2016 | Aman | |
| 2016/0249910 A1 | 9/2016 | Shelton, IV et al. | |
| 2016/0249918 A1 | 9/2016 | Shelton, IV et al. | |
| 2016/0310077 A1 | 10/2016 | Hunter et al. | |

(56) References Cited

U.S. PATENT DOCUMENTS

| | | | |
|---|---|---|---|
| 2016/0329614 | A1 | 11/2016 | Madan et al. |
| 2016/0338760 | A1 | 11/2016 | Houser et al. |
| 2016/0352134 | A1 | 12/2016 | Pawar et al. |
| 2017/0360976 | A1 | 12/2017 | Thomas et al. |
| 2018/0052854 | A1 | 2/2018 | Cue et al. |
| 2018/0169286 | A1 | 6/2018 | Henniges et al. |
| 2018/0372806 | A1 | 12/2018 | Laughery et al. |
| 2020/0281679 | A1 | 9/2020 | Wissmann |

FOREIGN PATENT DOCUMENTS

| | | | |
|---|---|---|---|
| DE | 102014112544 | A1 | 3/2016 |
| EP | 2774869 | A1 | 9/2014 |
| EP | 2849353 | A1 | 3/2015 |
| EP | 3098937 | A1 | 11/2016 |
| EP | 3242376 | A1 | 11/2017 |
| JP | H02142562 | A | 5/1990 |
| JP | 2005348941 | A | 12/2005 |
| WO | 03105308 | A1 | 12/2003 |
| WO | 2006001557 | A1 | 1/2006 |
| WO | 2007015639 | A2 | 2/2007 |
| WO | 2007090025 | A1 | 8/2007 |
| WO | 2016044651 | A1 | 3/2016 |
| WO | 2016186168 | A1 | 11/2016 |
| WO | 2016187295 | A1 | 11/2016 |
| WO | 2018192875 | A1 | 10/2018 |

OTHER PUBLICATIONS

English language abstract for WO 2016/186168 A1 extracted from espacenet.com database on Jan. 29, 2024, 2 pages.

International Search Report for Application No. PCT/US2020/025429 dated Sep. 24, 2020, 3 pages.

Partial International Search Report for Application No. PCT/US2020/025429 dated Jul. 14, 2020, 2 pages.

English language abstract and machine-assisted English translation for DE 101 09 358 C1 extracted from espacenet.com database on Oct. 6, 2021, 10 pages.

Machine-assisted English language abstract and machine-assisted English translation for DE 20 2012 102 803 U1 extracted from espacenet.com database on Oct. 6, 2021, 9 pages.

Machine-assisted English language abstract and machine-assisted English translation for DE 10 2014 112 544 A1 extracted from espacenet.com database on Oct. 6, 2021, 10 pages.

English language abstract and machine-assisted English translation for EP 2 774 869 A1 extracted from espacenet.com database on Oct. 6, 2021, 10 pages.

English language abstract for WO 2018/192875 A1 extracted from espacenet.com database on Oct. 6, 2021, 2 pages.

English language abstract and machine-assisted English translation for JP 2005-348941 A extracted from espacenet.com database on Aug. 5, 2025, 10 pages.

* cited by examiner

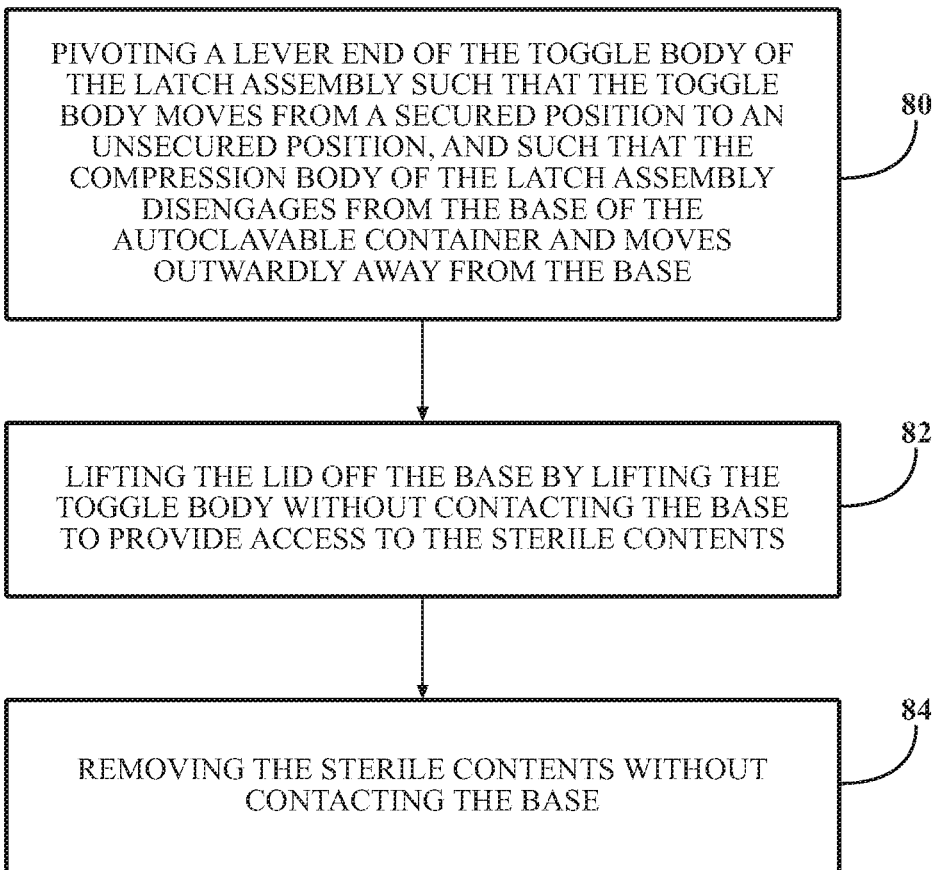

PIVOTING A LEVER END OF THE TOGGLE BODY OF THE LATCH ASSEMBLY SUCH THAT THE TOGGLE BODY MOVES FROM A SECURED POSITION TO AN UNSECURED POSITION, AND SUCH THAT THE COMPRESSION BODY OF THE LATCH ASSEMBLY DISENGAGES FROM THE BASE OF THE AUTOCLAVABLE CONTAINER AND MOVES OUTWARDLY AWAY FROM THE BASE ⎯ 80

LIFTING THE LID OFF THE BASE BY LIFTING THE TOGGLE BODY WITHOUT CONTACTING THE BASE TO PROVIDE ACCESS TO THE STERILE CONTENTS ⎯ 82

REMOVING THE STERILE CONTENTS WITHOUT CONTACTING THE BASE ⎯ 84

172 — Identification Data

174 — Useful Life of Battery

176 — Nominal Open Circuit Voltage

178 — Amount of Producible Current

180 — Amount of Available Energy

182 — Charging Instructions

184 — Charging History of Battery

186 — Autoclaving History of Battery

188 — Measured Post-Charge Voltage

190 — Highest Charging Temperature

192 — Device Usage

170

Sampling Length $lr$

FIG. 18E
$$Ra = \frac{1}{lr} \int_0^{lr} |Z(X)| \, dx$$
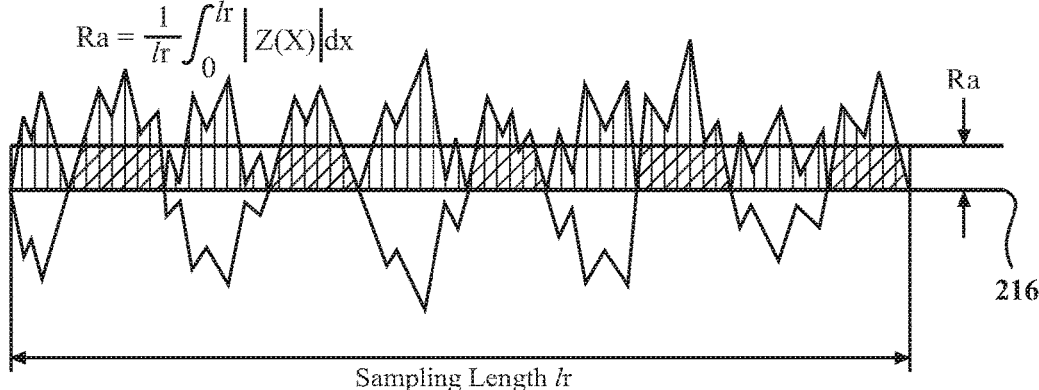
Ra
216
Sampling Length $lr$
$$Rq = \sqrt{\frac{1}{lr} \int_0^{lr} Z^2(X) \, dx}$$
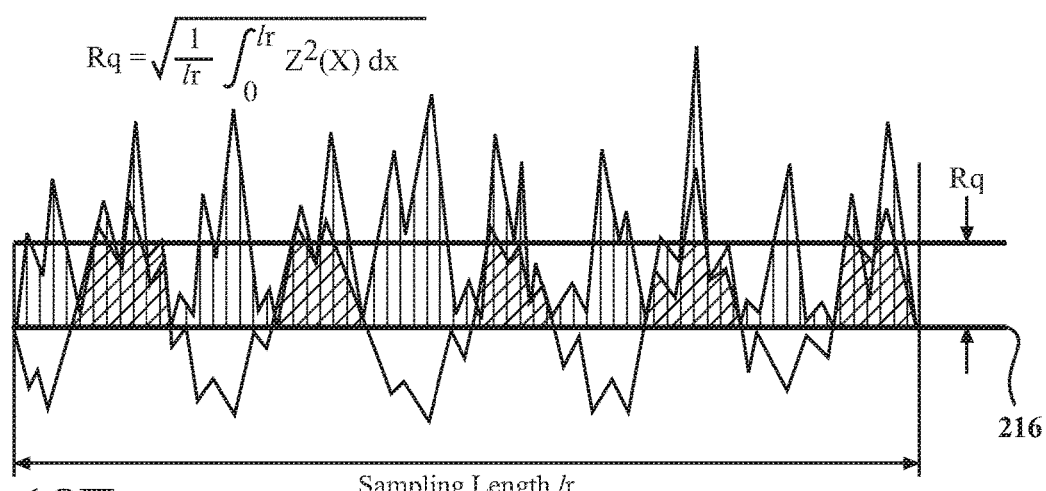
Rq
216
Sampling Length $lr$
FIG. 18F
$$Rsm = \frac{1}{m} \sum_{i=1}^{m} X_{si}$$
Xs1    Xs2    Xs3    Xsi    Xsm
216
Sampling Length $lr$
FIG. 18G

AUTOCLAVABLE CONTAINER FOR STERILIZING A WIRELESSLY CHARGEABLE BATTERY

CROSS-REFERENCE TO RELATED APPLICATIONS

This patent application is a National Stage of International Patent Application No. PCT/US2020/025429, filed on Mar. 27, 2020 which claims priority to and all the benefits of both U.S. Provisional Patent Application No. 62/965,614 filed on Jan. 24, 2020 and U.S. Provisional Patent Application No. 62/824,780 filed on Mar. 27, 2019, which are herein incorporated by reference in their entireties.

BACKGROUND

Non-rechargeable batteries are known as primary batteries while rechargeable batteries are known as secondary batteries. A secondary battery is capable of repeatedly being charged, storing the charge and delivering the charge to a medical device, such as a surgical tool, to which the battery is attached. The use of a battery eliminates the need to provide a power cord connected to an external power source. The elimination of the power cord offers benefits over corded surgical tools. Surgical personnel using this type of tool do not have to concern themselves with either sterilizing a cord so that it can be brought into the sterile surgical field surrounding the patient or ensuring that, during surgery, an unsterilized cord is not inadvertently introduced into the surgical field. Moreover, the elimination of the cord results in the removal of the physical clutter and field-of-view blockage the cord otherwise brings to a surgical procedure.

Batteries used to power surgical tools are exposed to adverse environmental elements to which batteries used for non-medical uses are seldom exposed. For example, during a surgical procedure, a medical battery may be exposed to blood or other body fluid. Tissue removed from the patient may adhere to the battery. It is therefore a required practice to sterilize the battery or ensure that the battery is housed within a sterilized housing between surgical procedures. Therefore, the batteries must either be sterilizable themselves, or may be non-sterile batteries that have a sterilizable housing in which the batteries are disposed. In the example of sterilizable batteries, the cleaning/sterilization process typically involves rinsing the battery to remove contaminants that are readily visible on the surface of the battery. However, these events may cause a conductive bridge to form between the battery contacts, which can lead to the formation of a layer of metal oxide on one or more of the contacts. This oxide layer functions as an impedance layer that reduces the efficiency of both the charging of the battery and the efficiency of the battery to deliver charge to the tool to which the battery is coupled.

The batteries may also be subjected to immersion in a steam-filled chamber as part of an autoclaving process. To survive the high temperatures present during the autoclave process, specialized batteries must be used. Autoclave temperatures often exceed 120 degrees Celsius. Even with specialized batteries that are designed to withstand autoclave temperatures, damage may still occur to the batteries during the autoclave process (although less damage than would occur with conventional batteries used in other environments). As a result, batteries used in medical environments that are subjected to autoclaving may sustain more damage than batteries used in other industries.

In addition, as batteries may be unused for a period of time before being connected to a surgical tool for use in a procedure, the batteries may gradually lose charge. Accordingly, a battery that started out with a full state of charge may gradually lose charge while disposed in a storage location and may not have a required level of charge when the battery is desired to be used. Health care professionals who use the surgical tools and associated batteries need to have confidence that the batteries used in the tools have a sufficient level of charge and have a sufficient level of health to be used in a surgical procedure or other potentially critical setting.

SUMMARY

An autoclavable container for sterilizing a wirelessly chargeable battery is disclosed. The autoclavable container includes a lid including metal and a base including a material permitting the transmission of an electromagnetic wave therethrough and having a glass transition temperature above 140 degrees Celsius. The lid defines a plurality of apertures configured to allow a sterilant to permeate the lid. The lid includes a mount configured to receive a filter defining a microbial barrier. The base defines a plurality of receptacles, each receptacle shaped to receive a wirelessly chargeable battery. The base also includes a plurality of protrusions, each protrusion being aligned with a corresponding receptacle.

An autoclavable container for sterilizing a wirelessly chargeable battery is disclosed. The autoclavable container includes a lid including metal and a base including a material permitting the transmission of an electromagnetic wave therethrough and having a glass transition temperature above 140 degrees Celsius. The lid defines a plurality of apertures configured to allow a sterilant to permeate the lid. The lid includes a mount configured to receive a filter defining a microbial barrier. The base defines a plurality of receptacles, each receptacle shaped to receive a wirelessly chargeable battery. The base also includes a plurality of protrusions, each protrusion being aligned with a corresponding receptacle. The autoclavable container also includes a latch assembly that includes a lever body having a handle portion and a body portion, the body portion defining a pivot aperture and a link aperture. The lever body is coupled to the first body and movable between a secured position and an unsecured position. A pivot shaft is disposed in the pivot bore of the first body and the pivot aperture of the lever body for facilitating pivoting movement of the lever body about the pivot shaft, wherein a head portion of the pivot shaft protrudes from the lever body. A link shaft is disposed in the link aperture and protrudes therefrom. The latch assembly further includes a clasp body having an interface end and a link end, wherein the link end defines a link bore configured to receive the link shaft such that the clasp body is pivotably coupled to the lever body, and wherein the interface end is configured to engage the lip of the base. The head portion of the pivot shaft is spaced from the clasp body when the lever body is in the secured position and as the lever body is pivoted away from the secured position the head portion engages the clasp body such that as the lever body is further pivoted toward the unsecured position the head portion moves the interface end of the clasp body away from the base.

An autoclavable container for sterilizing a wirelessly chargeable battery further disclosed. The autoclavable container may include a base including a lip, a lid configured for engaging the base, and a latch assembly. The latch assembly may include a first body fixedly coupled to the lid. The first body may define a pivot bore extending therethrough. The latch assembly may further include a lever body having a handle portion and a body portion, and the body portion may define a pivot aperture and a link aperture. The lever body may be coupled to the first body and pivotable between a secured position and an unsecured position. The latch assembly may further include a pivot shaft disposed in the pivot bore of the first body and the pivot aperture of the lever body for facilitating pivoting movement therebetween. The latch assembly may further include a link shaft disposed in the link aperture and movable therewith such that the link shaft passes between the pivot shaft and the lid as the lever body is pivoted between the secured position and the unsecured position. The latch assembly may further include a clasp body having an interface end and a link end, wherein the link end defines a link bore configured to receive the link shaft such that the clasp body is coupled to the lever body, and wherein the interface end is configured to engage the lip of the base. The latch assembly may further include a detent assembly disposed on the first body in abutment with the lever body for limiting free movement of the body from the unsecured position and the secured position.

A method of removing sterile contents housed in an autoclavable container in a sterile manner is disclosed. The container includes a base, a lid engageable with the base, and a latch assembly including a first body fixedly coupled to the lid, a lever body pivotably coupled to the body, and a clasp body engaged to the base. The method includes a step of pivoting a handle portion of the lever body of the latch assembly about the first body fixedly coupled to the lid such that the lever body moves from a secured position to an unsecured position, wherein the handle portion of the lever body is further from the base in the unsecured position than in the secured position, and such that the clasp body of the latch assembly disengages from the base of the autoclavable container and moves outwardly away from the base in response to pivoting the lever body from the secured position to the unsecured position. The method also includes steps of lifting the lid off the base by lifting the lever body without contacting the base to provide access to the sterile contents and removing the sterile contents without contacting the base.

An autoclavable container for sterilizing a wirelessly chargeable battery is disclosed. The autoclavable container includes a lid and a base, with one of the base and the lid defining a plurality of apertures configured to allow a sterilant to permeate the container. The autoclavable container also includes a removable tray including metal, the removable tray being configured to receive a wirelessly chargeable battery and allow for removal of the battery through lifting of the tray from the base. The removable tray includes a periphery and an opening in the periphery such that the removable tray includes an open periphery, the opening permitting the transmission of electromagnetic waves therethrough.

A system for sterilizing a wirelessly chargeable battery, the system including a wireless charging device including an antenna configured to transmit electromagnetic waves to provide charging power, a wirelessly chargeable battery, and an autoclavable container configured to be disposed on the wireless charging device. The autoclavable container includes a lid and a base, with one of the base and the lid defining a plurality of apertures configured to allow a sterilant to permeate the container. The autoclavable container also includes a removable tray including metal, the removable tray being configured to receive a wirelessly chargeable battery and allow for removal of the battery through lifting of the tray from the base. The removable tray includes a periphery and an opening in the periphery such that the removable tray includes an open periphery, the opening permitting the transmission of electromagnetic waves therethrough.

A system for sterilizing a wirelessly chargeable battery, the system includes a wirelessly chargeable battery including a bottom surface, an autoclavable container configured to receive the wirelessly chargeable battery. The autoclavable container includes a lid and a base, the lid defining a plurality of apertures configured to allow a sterilant to permeate the lid, the lid including a mount configured to receive a filter defining a microbial barrier, and the base defining a receptacle being shaped to receive a wirelessly chargeable battery and a protrusion aligned with the receptacle. The receptacle includes a floor and a standoff extending from the floor such that the wirelessly chargeable battery received by the receptacle is disposed on the plurality of standoffs and the bottom surface of the wirelessly chargeable battery is spaced from the floor to allow circulation of a sterilant underneath the battery such that a majority of the bottom surface is exposed to the sterilant.

A method of sterilizing a wirelessly chargeable battery in an autoclavable container including a lid and a base, the base including a receptacle being shaped to receive the wirelessly chargeable battery, a standoff extending from at least one of the floor of the receptacle and a bottom surface of the wirelessly chargeable battery. The method includes positioning the wirelessly chargeable battery within the receptacle of the autoclavable container such that the standoff spaces the bottom surface of the wirelessly chargeable battery from the floor of the receptacle, placing the autoclavable container in an autoclave, and sterilizing the autoclavable container such that a majority of a bottom surface of the battery is exposed to a sterilant.

An autoclavable wirelessly chargeable battery is disclosed. The autoclavable wirelessly chargeable battery includes a housing, a cell disposed within the housing, a ferrite base disposed between the cell and the housing, an induction coil disposed on the ferrite base, the induction coil being configured to receive electromagnetic waves, a radiofrequency coil disposed on the ferrite base, the radiofrequency coil being configured to receive radiofrequency signals, a microcontroller disposed between the housing and the cell and coupled to the induction coil and the radiofrequency coil, and a thermally insulative material at least partially disposed between the cell and the ferrite base.

An autoclavable wirelessly chargeable battery is disclosed. The autoclavable wirelessly chargeable battery includes a housing, a cell disposed within the housing, a thermally insulative material at least partially disposed between the housing and the cell, a ferrite base disposed between the cell and the housing, an induction coil disposed on the ferrite base, the induction coil being configured to receive electromagnetic waves, a radiofrequency coil disposed on the ferrite base, the radiofrequency coil being configured to receive radiofrequency signals, wherein the ferrite base is a monolithic component and the radiofrequency coil and the induction coil share the ferrite base. The autoclavable wirelessly chargeable container also includes a microcontroller disposed between the housing and the cell and coupled to the induction coil and the radiofrequency coil.

An autoclavable wirelessly chargeable battery is disclosed. The autoclavable wirelessly chargeable battery includes a housing, a cell disposed within the housing, a thermally insulative material at least partially disposed between the housing and the cell, a ferrite base disposed between the cell and the housing, an induction coil disposed on the ferrite base, the induction coil being configured to receive electromagnetic waves, a radiofrequency coil embedded in a medium of a flexible printed circuit board such that adjacent windings of the radiofrequency coil are fixed relative to one another by the medium of the flexible printed circuit board, the flexible printed circuit board being disposed on the ferrite base, the radiofrequency coil being configured to receive radiofrequency signals. Furthermore, the ferrite base is a monolithic component and the radiofrequency coil and the induction coil share the ferrite base. The autoclavable wirelessly chargeable battery also includes a microcontroller disposed between the housing and the cell and coupled to the induction coil and the radiofrequency coil.

An autoclavable wirelessly chargeable battery is disclosed. The autoclavable wirelessly chargeable battery includes a housing, a cell disposed within the housing, a thermally insulative material at least partially disposed between the housing and the cell, a ferrite base disposed between the cell and the housing, an induction coil disposed on the ferrite base and configured to receive electromagnetic waves, and a radiofrequency coil embedded in a medium of a flexible printed circuit board such that adjacent windings of the radiofrequency coil are fixed relative to one another by the medium of the flexible printed circuit board, the flexible printed circuit board being disposed on the ferrite base and the radiofrequency coil being configured to receive radiofrequency signals. Furthermore, the ferrite base is a monolithic component and the radiofrequency coil and the induction coil share the ferrite base and a microcontroller disposed between the housing and the cell and coupled to the induction coil and the radiofrequency coil.

A polymeric autoclavable container for sterilization having improved drying properties is disclosed. The polymeric autoclavable container includes a lid and a base, with at least one of the base and the lid defining a plurality of apertures configured to allow a sterilant to permeate the autoclavable container. Additionally, the base includes a polymeric material permitting the transmission of an electromagnetic wave therethrough, has a glass transition temperature above 140 degrees Celsius, and has a textured inner surface exhibiting a water contact angle of less than 90 degrees.

A polymeric autoclavable container for sterilization having improved drying properties is disclosed. The autoclavable container includes a lid and a base, with at least one of the base and the lid defining a plurality of apertures configured to allow a sterilant to permeate the autoclavable container. Additionally, the base includes a polymeric material permitting the transmission of an electromagnetic wave therethrough, has a glass transition temperature above 140 degrees Celsius, and has an inner surface which is hydrophilic.

A method of manufacturing a base for an autoclavable container is disclosed. The method includes molding the base for the autoclavable container from a polymeric material permitting the transmission of an electromagnetic wave therethrough and having a glass transition temperature above 140 degrees Celsius such that an inner surface exhibits a contact angle less than 90 degrees.

A method of manufacturing a base for an autoclavable container is disclosed. The method includes molding the base for an autoclavable container from a polymeric material permitting the transmission of an electromagnetic wave therethrough and having a glass transition temperature above 140 degrees Celsius and texturing the molded base such that an inner surface of the base exhibits a water contact angle of less than 90 degrees.

BRIEF DESCRIPTION OF THE DRAWINGS

Advantages of the present disclosure will be readily appreciated, as the same becomes better understood by reference to the following detailed description, when considered in connection with the accompanying drawings. Non-limiting and non-exhaustive instances of the present disclosure are described with reference to the following figures, wherein like numerals refer to like parts throughout the various views unless otherwise specified.

FIG. 3 is a flow chart of a method of removing sterile contents housed in an autoclavable container in a sterile manner.

FIGS. 18E-18G are plots illustrating various parameters used to characterize the plot of the roughness of the example texture in FIG. 18D.

DETAILED DESCRIPTION

Figure 1:
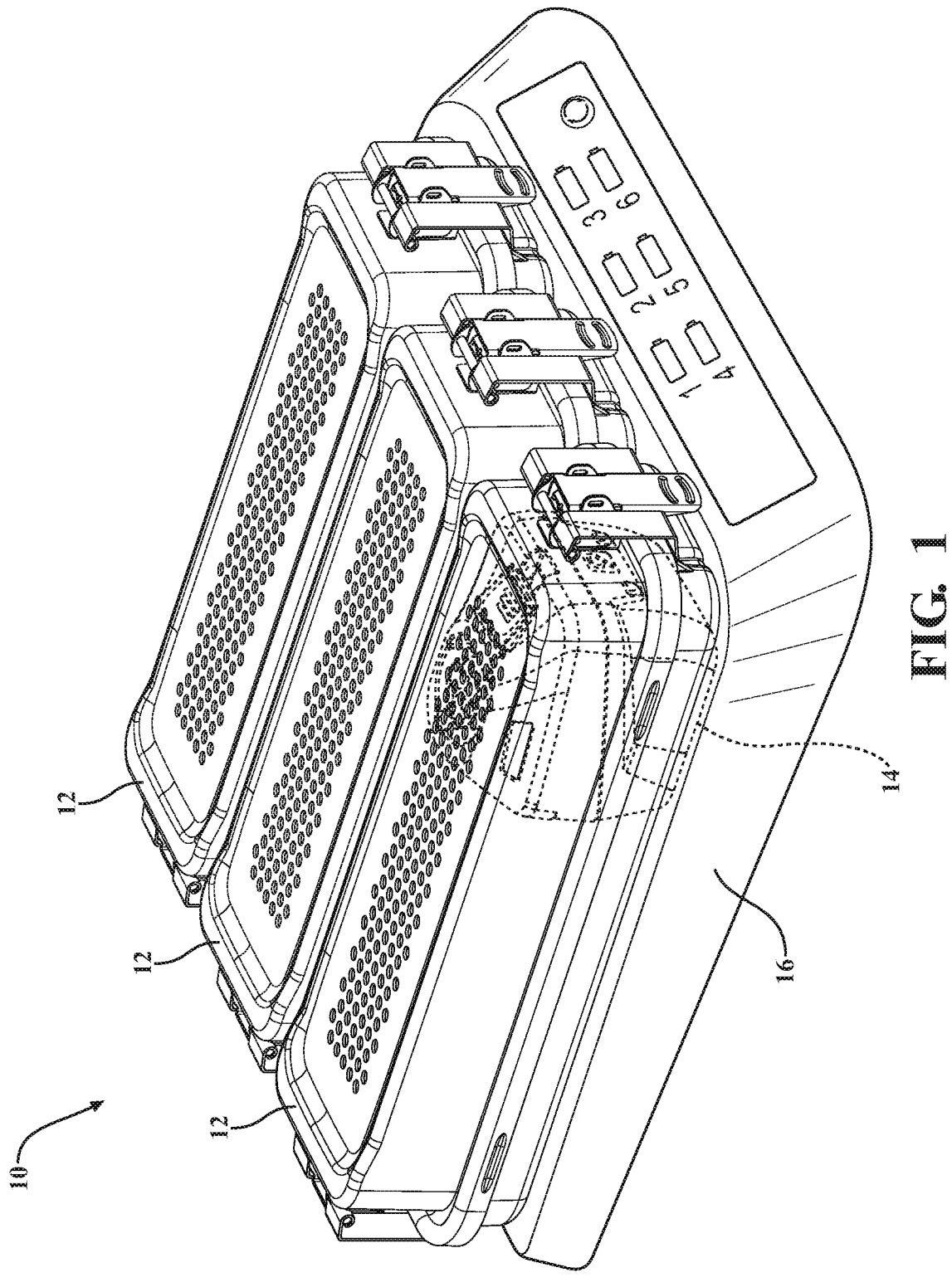
FIG. 1 is a perspective view of an autoclavable container housing a wirelessly chargeable battery and placed on a charging module.

In the following description, numerous specific details are set forth in order to provide a thorough understanding of the present disclosure. It will be apparent, however, to one having ordinary skill in the art that the specific detail need not be employed to practice the present disclosure. In other instances, well-known materials or methods have not been described in detail in order to avoid obscuring the present disclosure.

Reference throughout this specification to "one instance", "an instance", "one example" or "an example" means that a particular feature, structure or characteristic described in connection with the instance of example is included in at least one instance of the present disclosure. Thus, appearances of the phrases "in one instance", "in an instance", "one example" or "an example" in various places throughout this specification are not necessarily all referring to the same instance or example. Furthermore, the particular features, structures or characteristics may be combined in any suitable combinations and/or sub-combinations in one or more instances or examples. In addition, it is appreciated that the figures provided herewith are for explanation purposes to persons ordinarily skilled in the art and that the drawings are not necessarily drawn to scale.

The present disclosure particularly describes a battery that is capable of being charged by a wireless charging module having at least one charging bay. The wirelessly chargeable battery may be sterilized and placed in an autoclavable container that is capable of being sterilized and retaining a sterile state of a volume contained therein. In other words, the autoclavable container provides a microbial barrier such that the contents within the autoclavable container are maintained in a sterile state until the autoclavable container has been opened. The autoclavable container may then be transported to the charging module and the wirelessly chargeable battery may be charged while remaining in the sterile volume. The wirelessly chargeable battery may also communicate with the charging module while the wirelessly chargeable battery remains in the sterile volume. While the wirelessly chargeable battery is being transported to the charging module, the wirelessly chargeable battery and its internal components may be in a low power state.

When the wirelessly chargeable battery is placed in proximity to the charging bay, a communication antenna associated with the charging bay generates an electromagnetic field that is used to communicate with a battery communication device. A power antenna is also associated with the charging bay and may be disabled when the communication antenna is enabled. In one instance, the battery communication device includes a communication device, such as a near-field communication (NFC) tag with an integrated RF antenna. In other instances, other tags such as RFID tags or other suitable circuits coupled to an antenna may be used. The antenna is energized by the electromagnetic field of the charging module and the battery communication device exits the low power state to pair with the charging module. In one instance, all other components of the wirelessly chargeable battery, such as the battery controller, charging circuit, etc., may exit the low power state when the RF tag antenna is energized or when the wirelessly chargeable battery is paired with the charging module.

After the wirelessly chargeable battery and charging module have been paired, the charging module may receive battery state data, such as battery state of charge data and battery state of health data, from the NFC tag or other communication device. The charging module may indicate the battery state data on one or more indicators, such as within a display area of the charging module (see FIG. 11A). The charging module may also receive battery operational data from the NFC tag.

When the charging module has received the battery state data and/or the battery operational data, the charging module may determine whether the wirelessly chargeable battery is ready to charge by transmitting an associated request to the wirelessly chargeable battery. If the wirelessly chargeable battery responds to the request with a message indicating that it is ready to charge, the charging module begins a charging process.

The charging module may begin the charging process by disabling the communication antenna and enabling the power antenna of the charging bay associated with the battery. The power antenna generates an electromagnetic field that inductively couples to a corresponding antenna within the battery. Charging power is then provided from the charger power antenna to the battery antenna to charge the battery cells. After a predetermined time has elapsed, the charger controller may disable the power antenna, re-enable the communication antenna, and begin the process again by pairing the charging device to the battery using the communication antenna and battery communication device. In this way, the charger controller may periodically receive updated data from the battery to determine whether additional power should be wirelessly provided to the battery.

FIG. 1 is a perspective view of a system 10 that includes an autoclavable container 12 for sterilizing a wirelessly chargeable battery 14 and a charging module 16 for providing charging power to the wirelessly chargeable battery 14. As described more fully herein, each autoclavable container 12 may receive one or more wirelessly chargeable batteries 14, and each charging module 16 may receive one or more autoclavable containers 12. After the autoclavable container 12 receives a wirelessly chargeable battery 14 and the charging module 16 receives autoclavable container 12, the charging module 16 establishes communication with the wirelessly chargeable battery 14 and provides charging power to the wirelessly chargeable battery 14. Herein, each of the autoclavable container 12, the wirelessly chargeable battery 14, and the charging module 16 will be described in further detail.

The autoclavable container 12 is configured to receive one or more wirelessly chargeable batteries 14 for sterilization in an autoclave and for charging by the charging module 16. The autoclavable container 12 allows the wirelessly chargeable batteries 14 to be sterilized and transported to a desired location of use (e.g., an operating room) using a variety of methods.

In one such method, the wirelessly chargeable batteries 14 may be placed within the autoclavable container 12 prior to sterilization. The autoclavable container 12 may then be sterilized in an autoclave process (or other suitable sterilization process) while the wirelessly chargeable batteries 14 remain inside the autoclavable container 12. Thus, in this method, the wirelessly chargeable batteries 14 and the autoclavable container 12 may be sterilized together and a volume 30 (shown in FIG. 2B) within the autoclavable container 12 may be sterilized or maintained in a sterile state. The autoclavable container 12 may then be carried or otherwise transported to the desired location of use while maintaining the sterile state of wirelessly chargeable batteries 14 and sterile volume 30.

In another such method, the wirelessly chargeable batteries 14 may be sterilized in an autoclaving process (or another suitable process) and may then be placed into the autoclavable container 12. The autoclavable container 12 may alternatively be sterilized to ensure that a volume 30 (shown in FIG. 2B) within the autoclavable container 12 is suitably sterile. The wirelessly chargeable batteries 14 are thus placed into the sterile volume 30 of the autoclavable container 12 such that the sterile state of the wirelessly chargeable batteries 14 is maintained. The autoclavable container 12 may then be sealed and carried or otherwise transported to the desired location of use while maintaining the sterile state of the wirelessly chargeable batteries 14 and the sterile volume 30.

Accordingly, after using either of the above methods to sterilize the wirelessly chargeable batteries 14, the autoclavable container 12 housing the wirelessly chargeable batteries 14 may be placed within a proximity of the charging module 16 to charge the wirelessly chargeable batteries 14. As such, the charging module 16 may provide charging power to the wirelessly chargeable batteries 14 while the wirelessly chargeable batteries 14 remain microbially sealed within sterile volume 30. In addition, the charging module 16 may communicate with the wirelessly chargeable batteries 14 while the wirelessly chargeable batteries 14 are housed within the sterile volume 30 to obtain battery operational data, battery state data, and/or any other suitable data described herein.

In an alternative instance, the wirelessly chargeable batteries 14 may be placed in the autoclavable container 12 prior to sterilization, and the autoclavable container 12 may be placed within a proximity of the charging module 16 such that the wirelessly chargeable batteries 14 receive charging power while the autoclavable container 12 and the wirelessly chargeable batteries 14 are in the non-sterile state. In such an instance, after the wirelessly chargeable batteries 14 receive charging power from the charging module 16, the autoclavable container 12 and the wirelessly chargeable batteries 14 may be sterilized in an autoclave such that the wirelessly chargeable batteries 14 are stored in a sterile and charged state until the autoclavable container 12 is opened.

In another alternative instance, the autoclavable container 12 may be used to sterilize a surgical instrument other than the wirelessly chargeable batteries 14. For instance, the methods described herein may be used to sterilize manual surgical instruments, such as scalpels, forceps and osteotomes. The methods described herein may also be used to sterilize powered surgical instruments, such as rotary handpieces, drills, or endoscopes.

FIGS. 2A-2F illustrate various views of the autoclavable container 12. As shown, the autoclavable container 12 is substantially rectangular in shape. However, it should be recognized that the autoclavable container 12 may be any suitable shape that enables the autoclavable container 12 to operate as described herein.

Figure 2A:
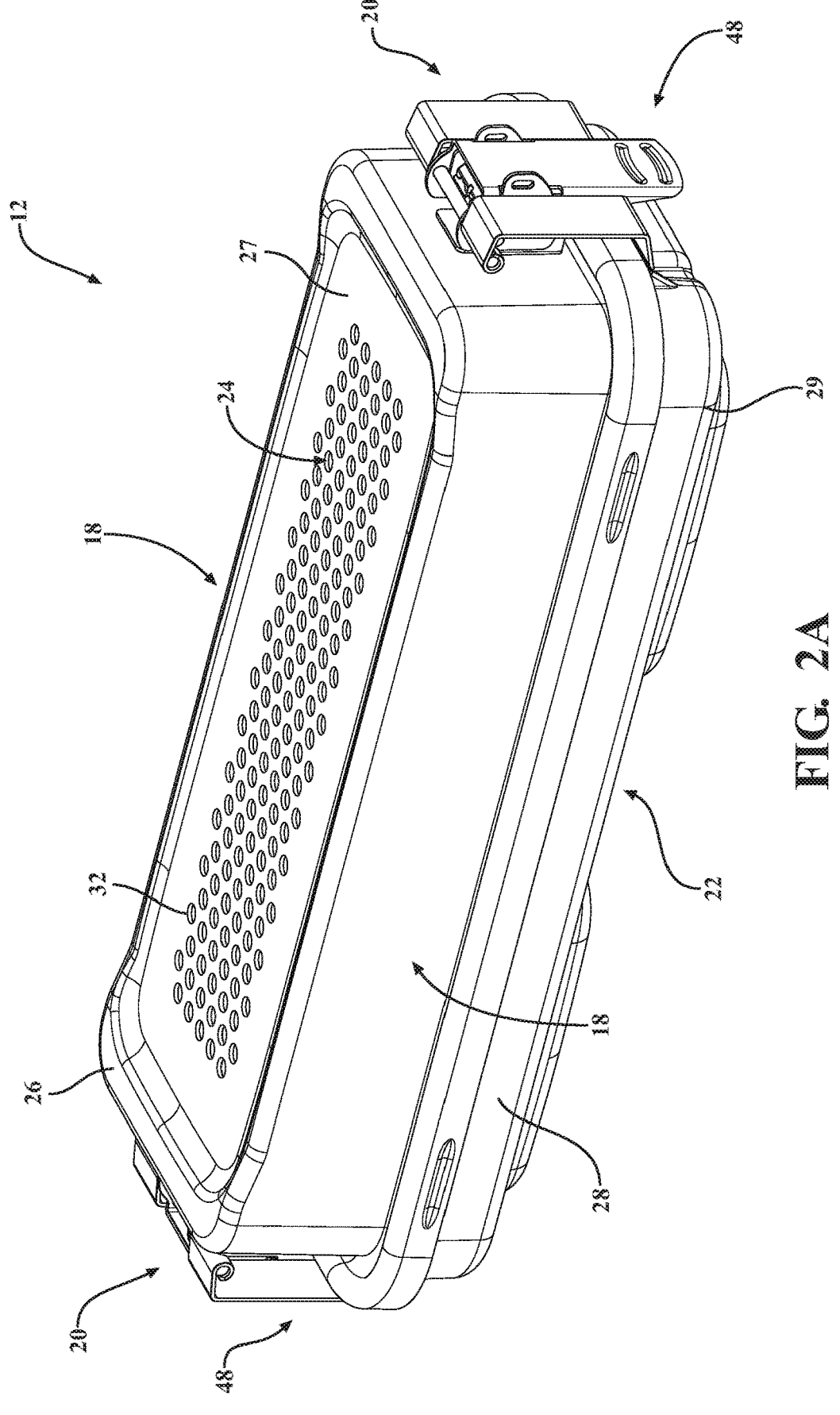
FIG. 2A is a perspective view of the autoclavable container.

As shown in FIG. 2A, the autoclavable container 12 may include two opposing side portions 18, two opposing end portions 20, a bottom portion 22, and a top portion 24. In the instance shown in FIG. 2A, the autoclavable container 12 includes a lid 26 and a base 28, which are sealable to one another through use of one or more seals to define the volume 30 (shown in FIG. 2B) within the autoclavable container 12. The lid 26 and the base 28 each include an outer surface 27, 29, respectively. The lid 26 and the base 28 also include an inner surface 31, 33, respectively (shown in FIGS. 6B and 6C, respectively) which cooperate to define the volume 30. In one instance, the lid 26 is removable from the base 28 to enable one or more wirelessly chargeable batteries 14 to be removably placed inside the autoclavable container 12, as shown in FIG. 2A.

The lid 26 of the autoclavable container 12 may include metal and is configured to retain heat to facilitate drying of contents thereof. For example, in an instance where the autoclavable container 12 houses a wirelessly chargeable battery 14, the autoclavable container 12 may be placed in an autoclave to sterilize the wirelessly chargeable battery 14 with a high-temperature sterilant, such as steam, hydrogen peroxide, ozone, or ethylene oxide. This may result in liquid condensing on the inside of the autoclavable container 12 or the wirelessly chargeable battery disposed therein. After the wirelessly chargeable battery 14 is sterilized and removed from an autoclave, the lid 26 retains heat from the autoclave to facilitate drying of the wirelessly chargeable battery 14 housed within the autoclavable container 12. As such, the lid 26 includes a thermal conductivity of greater than or equal to 1 W/(m*K) at 298 Kelvin. In some instances, the lid 26 consists of, or consists essentially of, metal. In other instances, the lid 26 may not include metal. For example, the lid 26 may include a polymeric material. In such instances, the lid 26 may include a material other than metal that still facilitates drying of contents thereof by retaining heat from the autoclave.

The base 28 of the autoclavable container 12 includes a material having a glass transition temperature above 140 degrees Celsius. As previously stated, the autoclavable container 12 housing a wirelessly chargeable battery 14 may be placed in an autoclave to sterilize the wirelessly chargeable battery 14 with a high-temperature sterilant. As such, the base 28 includes a material having a glass transition temperature above 140 degrees Celsius because temperatures inside an autoclave can exceed 120 degrees Celsius.

The base 28 of the autoclavable container 12 also includes a material permitting the transmission of an electromagnetic wave therethrough. As previously stated, the charging module 16 may receive the autoclavable container 12 and provide charging power to the wirelessly chargeable battery 14. In some instances, the charging power is provided as an electromagnetic wave. Therefore, the base 28 includes a material permitting transmission of electromagnetic waves therethrough to receive the charging power via an electromagnetic wave. As such, the base 28 may include a material comprising a dielectric constant of less than or equal to ten or a dielectric constant less than or equal to five to permit the transmission of electromagnetic waves therethrough. For example, the base 28 may include a polymeric material permitting the transmission of an electromagnetic wave therethrough, such as a plastic. As another example, the base 28 may include a material other than a polymeric material that permits the transmission of an electromagnetic wave therethrough, such as a glass.

In one such instance, the material permitting the transmission of an electromagnetic wave therethrough may be a polymeric material and the base 28 may be formed of the polymeric material via injection molding. The polymeric material may comprise the poly(aryl ether sulfone) (P) in a weight amount of at least 10%, at least 30% or at least 50%, based on the total weight of the polymeric material. Preferably, the polymeric material comprises the poly(aryl ether sulfone) (P) in a weight amount of at least 70%, based on the total weight of the polymeric material. More preferably, the polymeric material comprises the poly(aryl ether sulfone) (P) in a weight amount of at least 90%, if not at least 95%, based on the total weight of the polymeric material. Still more preferably, the polymeric material consists essentially of the poly(aryl ether sulfone) (P). The most preferably, it consists essentially of the poly(aryl ether sulfone) (P). The poly(aryl ether sulfone) (P) advantageously has a weight average molecular weight in the range of from 20,000 to 100,000. Preferably, the poly(aryl ether sulfone) (P) has a weight average molecular weight in the range of from 40,000 to 70,000. The weight average molecular weight can be determined by Gel Permeation Chromatography using conventional polystyrene calibration standards. The base 28 may comprise a polyphenylsulfone homopolymer, i.e. a polymer of which essentially (and, preferably, all) the recurring units are of formula (H). RADEL® R polyphenylsulfone from SOLVAY ADVANCED POLYMERS, L.L.C. is an example of a polyphenylsulfone homopolymer.

As shown in FIG. 2A, the autoclavable container 12 may include a latch assembly 48. One configuration of the latch assembly 48 is illustrated in FIGS. 4A-4F, wherein the latch ssembly 48 is generally shown and labelled in FIGS. 4A-5C, and more specifically shown and labelled in FIGS. 4E and 4F. Other configurations of the latch assembly may also be implemented to fasten the lid 26 to the base 28. For example, the latch assembly shown in FIGS. 1-2B, which operates in substantially the same manner as will be described below in connection with the latch assembly 48 shown in FIGS. 4A-5C. Alternatively, the latch assembly shown in FIGS. 6A and 6B may also be utilized.

Most generally, the latch assembly 48 allows the user to securely fasten the lid 26 to the base 28 by utilizing mechanical advantage. To this end, the latch assembly 48 may comprise a first body 502, a lever body 504, and a clasp body 506. As will be described in further detail below, the first body 502 may be fixedly coupled to the lid 26, the lever body 504 may be coupled to the first body 502, and the clasp body 506 may be coupled to the lever body 504. In some configurations the first body 502 may be coupled to the base 28 and configured such that the clasp body 506 engages the lid 26 to fasten the base 28 to the lid 26. Herein, when the lever body 504 is moved such that the latch assembly 48 is moved between the unsecured position and the secured position, the lever body 504 may be said to have moved between the unsecured position and the secured position.

By moving the lever body 504 between the secured position and unsecured position, a user may secure/unsecure the lid 26 to/from the base 28 without needing to separately touch the clasp body 506 (described below). Shown in FIGS. 4A-4D, the base 28 includes a lip 68 integrally formed with the base 28. This is advantageous because, during transfer of the autoclavable container 12, the base 28 may contact a non-sterile surface. More generally stated, when removing sterile contents from the autoclavable container 12, it is advantageous to limit contact between a user and the autoclavable container 12 when removing the sterile contents. As such, because the user may remove the lid 26 of the autoclavable container 12 from the base 28 of the autoclavable container 12 without separately contacting the base 28 and/or the clasp body 506, the user is able to remove sterile contents from the autoclavable container 12 in a sterile manner.

As mentioned above, the first body 502 is fixedly coupled to the lid 26, and as shown in the figures, may be connected to one of the ends 20 of the lid 26. Here, the lid 26 includes two latch assemblies 26, which are arranged on the shorter of two pairs of opposing sides. The first body 502 comprises an outer face 508 that is parallel to the ends 20 of the lid 26 to which the first body 502 is coupled, and two lateral faces 510 that extend from the outer face 508 toward the lid 26. Several features are defined in the lateral faces 510, a pivot bore 512 is defined in the first body 502 and extends between each of the lateral faces 510 and defines a pivot axis 514. The pivot axis 514 is generally parallel to the outer face 508 and configured to receive a pivot shaft 516, as will be discussed in further detail below. The first body 502 may further define a link slot 518 that extends between each of the lateral faces 510 and is configured to receive a link shaft 520, also discussed in further detail below. The link slot 518 is radially arranged about the pivot axis 514 such that, when viewed from a direction parallel with the pivot axis 514, the link slot 518 has an arcuate profile, which is curved about a center point arranged on the pivot axis 514. Said differently, a centerline of the link slot 518 is defined by a semi-circular arc centered on the pivot axis 514. In the embodiment illustrated herein, the length of the arc that defines the link slot 518 may be between seventy-five degrees (75°) and one hundred and thirty-five degrees (135°), and in some cases may be between approximately 100° and 120°. Additionally, the first body 502 is configured such that at least a portion of the link slot 518 is arranged between the pivot bore 512 and the lid 26.

Operation of the latch assembly 48 is effected via the lever body 504. The lever body 504 has a handle portion 522 and a body portion 524, the handle portion 522 is configured to be grasped by a user in furtherance of operating the latch assembly 48 and the body portion 524 is configured to effect coordinated movement of the latch assembly 48 in response to actuation of the handle portion 522. The body portion 524 of the lever body 504 may comprise a front wall 526 and two side walls 528. The side walls 528 extend in a generally perpendicular direction from opposing sides of the front wall 526 toward an edge 530. The front wall 526 and the side walls 528 may be formed, for example, by bending opposite edges 530 of a flat material to form a U shape. A pair of wings 532 protrude from the front wall 526 in a generally parallel direction to partially form the handle portion 522 of the lever body 504. A pivot aperture 534 and a link aperture 536 are defined in the body portion 524 of the lever body 504, each extending through at least one of the side walls 528. The pivot aperture 534 is configured to receive the pivot shaft 516 and the link aperture 536 is configured to receive the link shaft 520. A recess 562 may further be defined in one or both of the side walls 528. The recess 562 shown in FIG. 4E extends through the side wall 528, however the recess may be a dimple, having localized area of reduced thickness disposed on only one side of one or both of the side walls 528, or a dimple that produces a raised feature on one side of one or both of the side walls 528 resulting from deformation of the opposing side of the respective side wall 528.

Figure 4A:
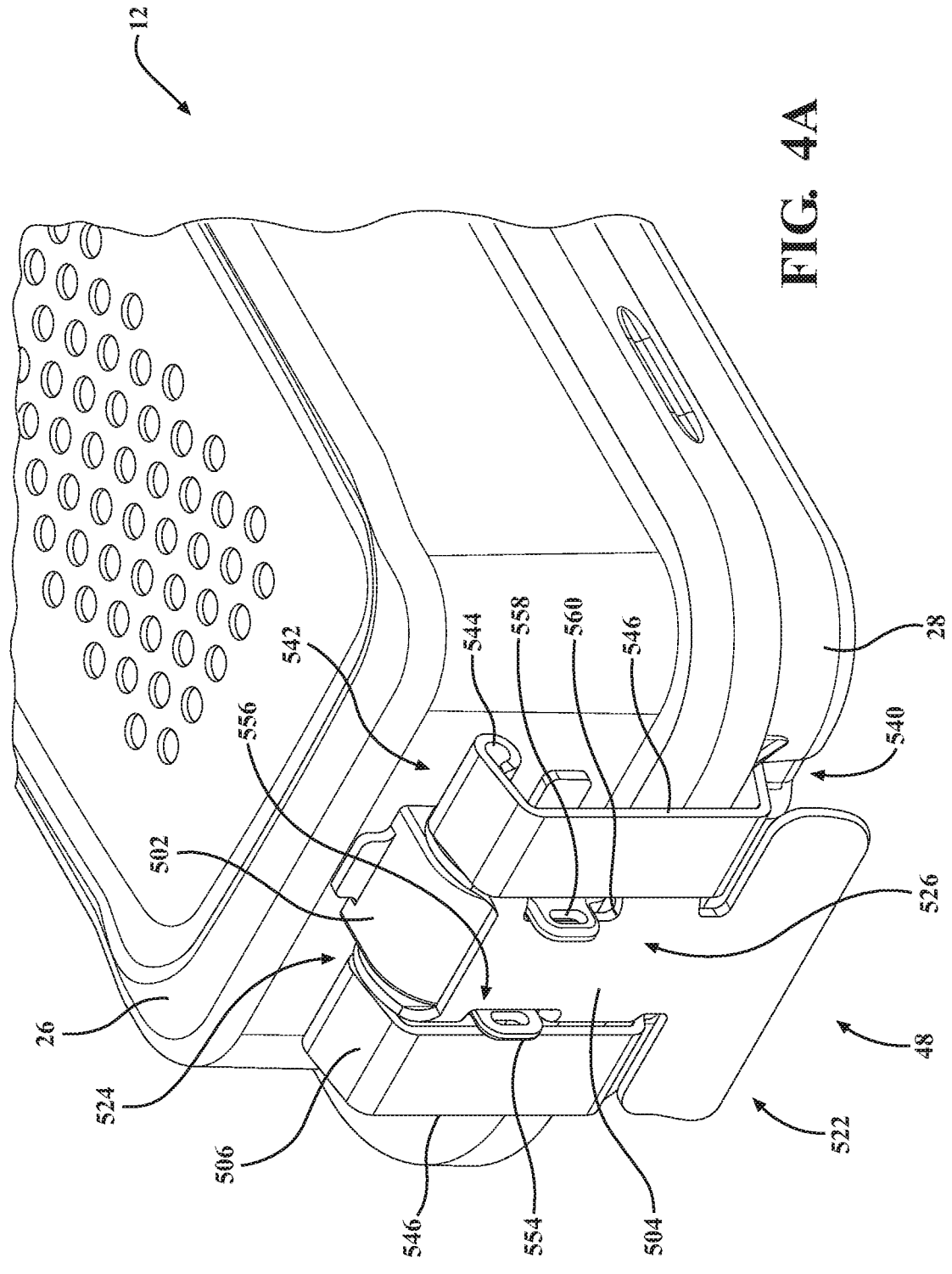
FIG. 4A is a perspective view of a latch assembly of the autoclavable container in a secured position.
Figures 4B, 4C:
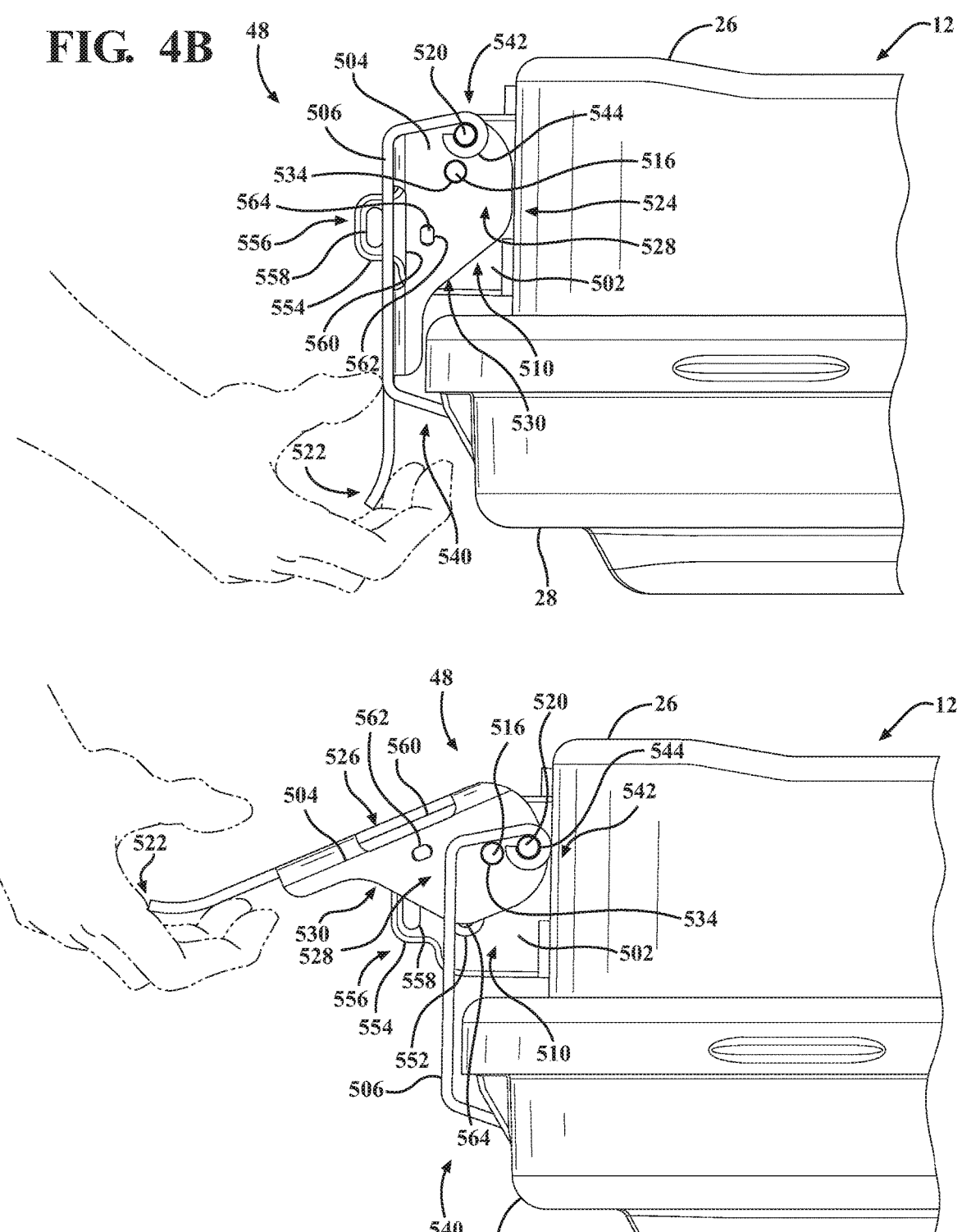
FIG. 4B is a side view of a latch assembly of FIG. 4A in the secured position.
FIG. 4C is a side view of the last assembly of FIG. 4A in an intermediate position.
Figure 4D:
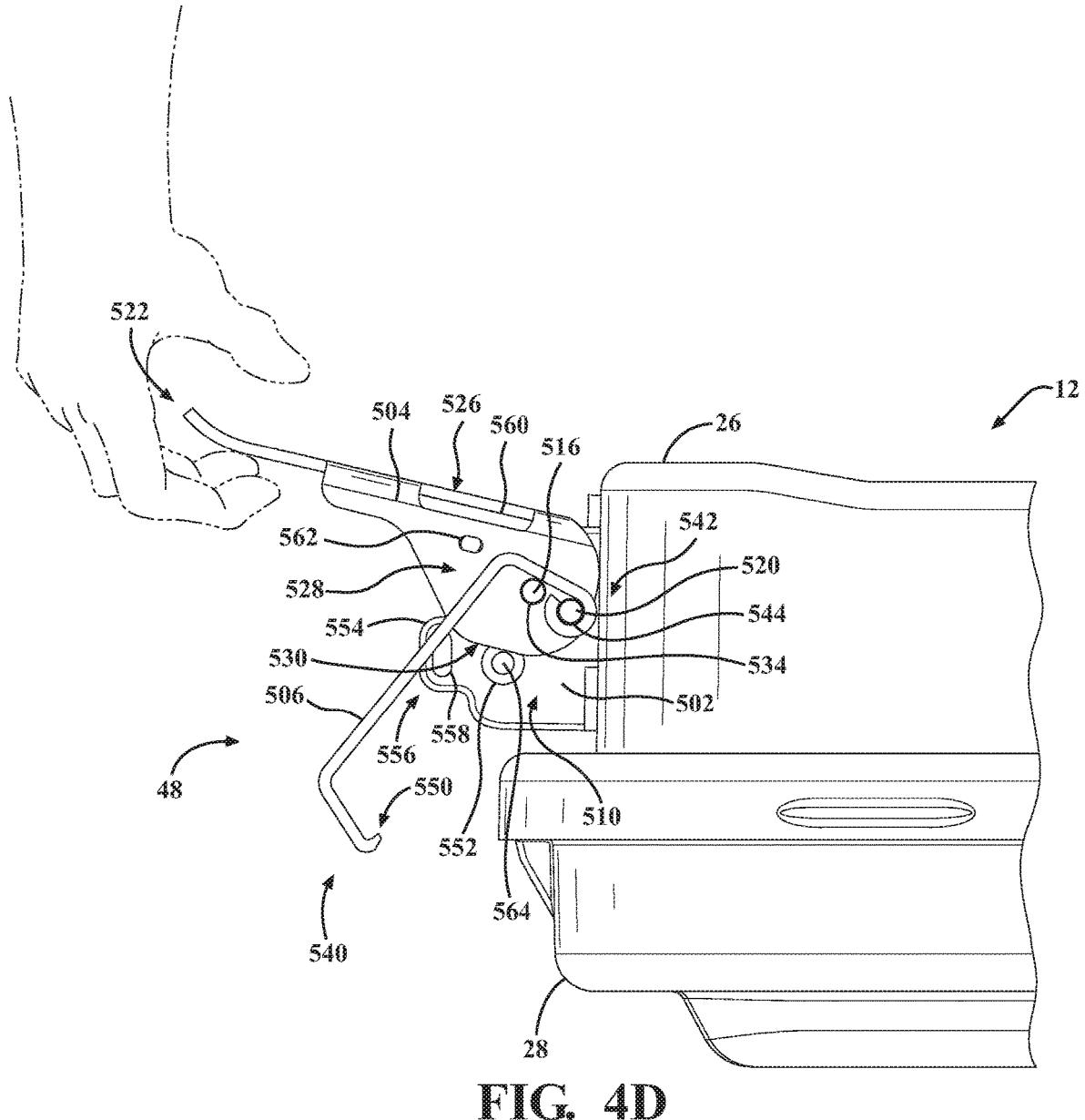
FIG. 4D is a side view of the latch assembly of FIG. 4A in an unsecured position.
Figure 4E:
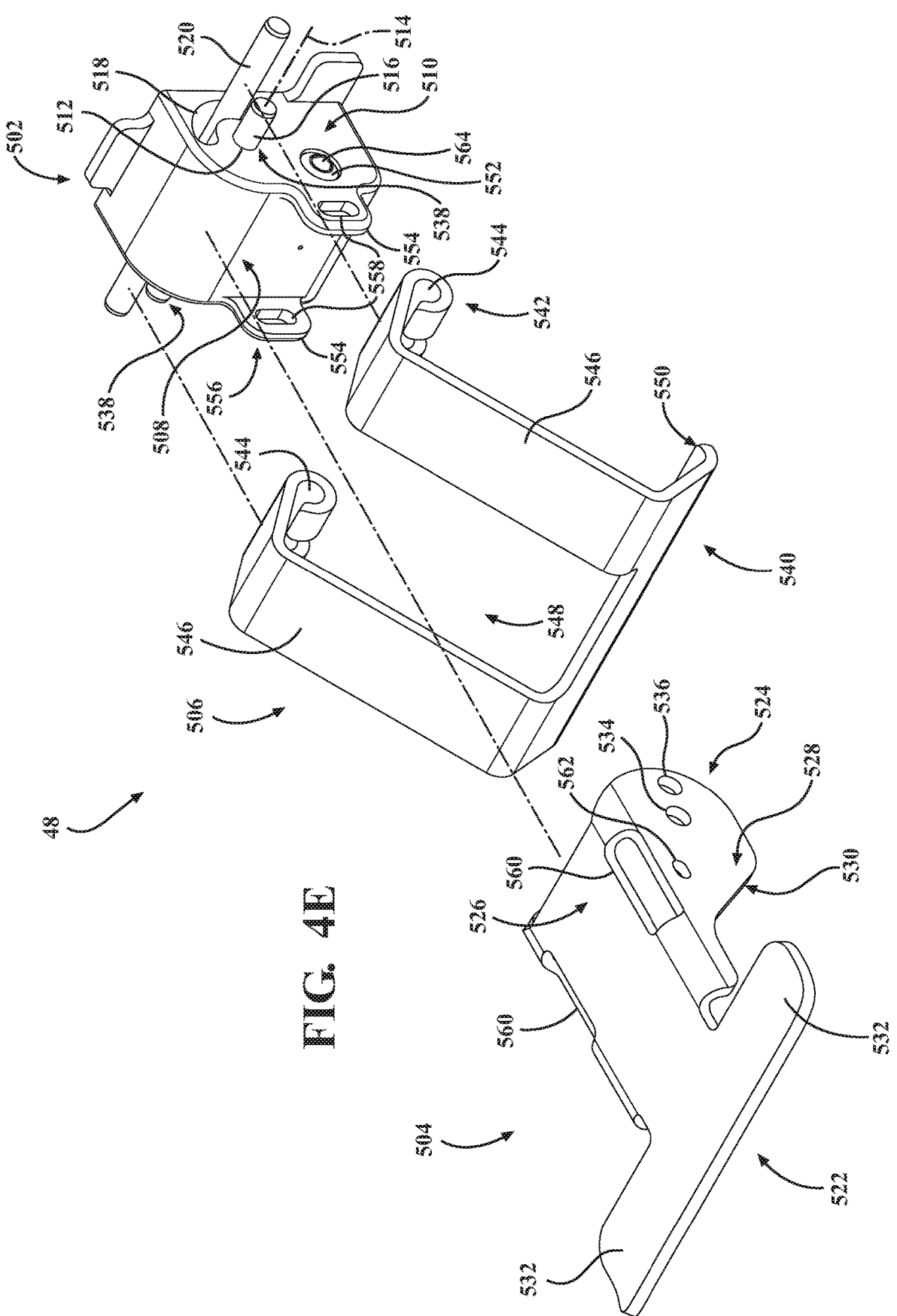
FIG. 4E is an exploded view of the latch assembly of FIG. 4D in the unsecured position.
Figure 4F:
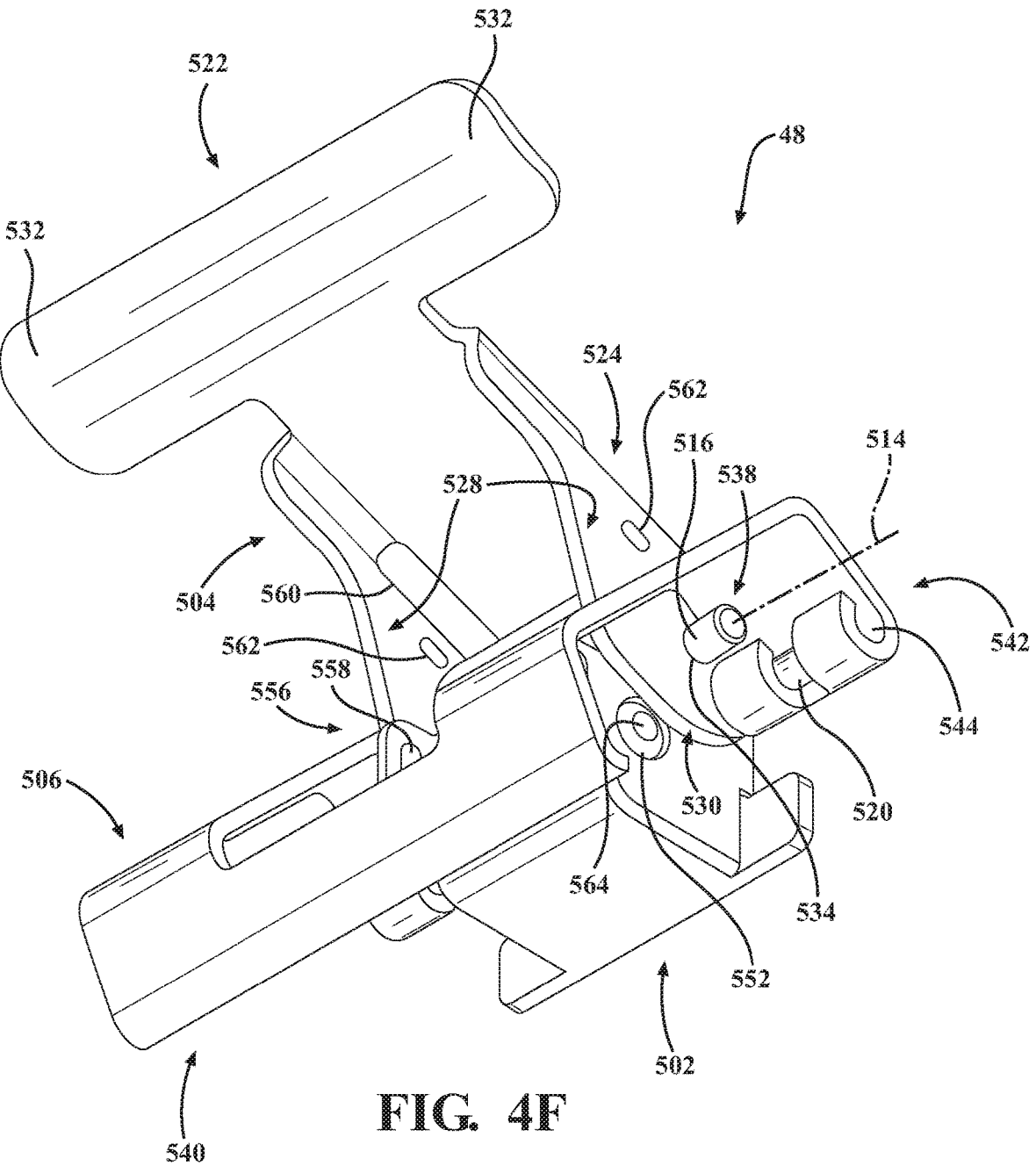
FIG. 4F is a bottom side perspective view of the latch assembly of FIG. 4D in the unsecured position.

The lever body 504, being coupled to the first body 502, is configured to move in a pivoting motion relative to the first body 502 between a secured position and an unsecured position. The lever body 504 is disposed on the first body 502 with the side walls 528 positioned adjacent to the lateral faces 510 of the first body 502 such that the pivot aperture 534 in the side walls 528 are aligned with the pivot bore 512 of the first body 502. The pivot shaft 516 is inserted through the pivot bore 512 and the pivot apertures 534, thereby pivotably coupling the lever body 504 to the first body 502. Turning now to FIGS. 4B-4D, the lever body 504 is shown in a secured position (FIG. 4B), an intermediate position (FIG. 4C), and an unsecured position (FIG. 4D). The lever body 504 is pivotable relative to the first body 502 about the pivot axis 514 between the secured position and the unsecured position. The secured position is generally defined by the lever body 504 being arranged approximately parallel to the outer face 508 of the first body 502, and the handle portion 522 spaced relatively near the base 28 of the sterilization container 12. The unsecured position is generally defined by the lever body 504 being arranged approximately perpendicular to the outer face 508 of the first body 502, and the handle portion 522 spaced relatively far from the base 28 of the sterilization container 12. Said differently, the handle portion 522 is positioned closer to the lid base 28 in the secured position than in the unsecured position. While parallel and perpendicular are used to generally describe the position the lever body 504 with respect to other features of the latch assembly 48, they are merely terms of description rather than precise measurements of the position of the specific components to which they are referencing. In this way, it is contemplated that in the secured position the front wall 526 of the lever body 504 could be at an angle that is within approximately 30° of parallel to the outer face 508 of the first body 502. Likewise, in the unsecured position the front wall 526 of the lever body 504 could be at an angle that is within approximately 30° of perpendicular to the outer face 508 of the first body 502.

In addition to being disposed in both the pivot bore 512 and the pivot aperture 534, the length of the pivot shaft 516 is such that a head portion 538 protrudes from the pivot aperture 534 away from the first body 502. The pivot shaft 516 may have two head portions 538 (only one shown) arranged on opposing sides of the pivot shaft 516 such that each head portion 538 protrudes from one of the pivot apertures 534 in a direction away from the lateral faces 510 of the first body and the side walls of the lever body 504. The pivot shaft 516 may be secured in position or to either of the lever body 504 and/or the first body 502 via several methods. For example, one exemplary method may utilize a press first between the pivot shaft 516 and the pivot bore 512 such that the lever body 504 pivots relative to the pivot shaft 516. Alternatively, a press fit between the pivot shaft 516 and the pivot aperture 534 may be utilized such that the pivot shaft 516 moves with the lever body 504 relative to the first body 502. Further methods, such as staking, fasteners, welding, and the like may also be utilized either in the alternative or in combination.

Movement of the lever body 504 is transferred to the base 28 via the clasp body 506, which is coupled to the lever body 504. The clasp body 506 has an interface end 540 and a link end 542. The interface end 540 is configured to engage the lip 68 of the base 28 for tensioning the lid 26 toward the base 28. The link end 542 defines a link bore 544, which is configured to receive the link shaft 520 such that the clasp body 506 is coupled to the lever body 504 and movable about the link shaft 520. Movement of the link end 542 of the clasp body 506 corresponds to movement of the link aperture 536 in the lever body 504, which moves along a semi-circular arc within the link slot 518 as the lever body 504 moves between the secured position and the unsecured position. As shown in FIG. 4D, the clasp body 506 further comprises two side portions 546 with a pocket 548 defined therebetween. The side portions 546 extend between the interface end 540 and the link end 542 and are spaced so as to receive a portion of the lever body 504 in the pocket 548 as the lever body 504 is moved toward the secured position.

In some configurations, the link bore 544 may be formed on the link end 542 of the clasp body 506 by bending an end of each of the side portions 546 around and back toward the interface end 540 at a radius suitable to receive the link shaft 520. The interface end 540 may be similarly bent to form a hooked profile 550 that is suitable to engage the lip 68 of the base 28 such that when the clasp body 506 is engaging the base 28 and the lever body 504 is in the secured position the interface end 540 is not readily disengaged. In other instances, such as instances wherein the interface end 540 does not include the hooked profile 550 and/or the base 28 does not include the lip 68, the interface end 540 may be configured to engage with the base 28 via alternative means.

As mentioned above, the link shaft 520 is disposed in the link slot 518, the link aperture 536, and the link bore 544. Similar to the pivot shaft 516 described above, the link shaft 520 may be secured to the link aperture 536 or the link bore 544 by various methods such as, for example, a press fit, welding, fasteners, adhesives, and the like. For example, one exemplary method may utilize a press first between the link shaft 520 and the link bore 544 such that the lever body 504 moves freely on the link shaft 520. Alternatively, a press fit between the link shaft 520 and the link aperture 536 may be utilized such that the clasp body 506 moves freely on the link shaft 520.

Referring again to the side views shown in FIGS. 4B-4D, where the latch assembly 48 is shown in the secured position, the intermediate position, and the unsecured position along with corresponding movement of the clasp body 506. Movement of the lever body 504 toward the unsecured position moves the clasp body 506 to disengage the interface end 540 from the lip 68 of the base 28. As the lever body 504 is pivoted the link shaft 520 moves in a semi-circular arc, such that the link shaft 520 moves from a position generally above the pivot shaft 516 to a position generally below the pivot shaft 516 and the link end 542 of the clasp body 506 moves in a downward direction. Movement of the clasp body 506 can be defined relative to the head portion 538 of the pivot shaft 516. Specifically, the head portion 538 of the pivot shaft 516 is spaced from the clasp body 506 when the lever body 504 is in the secured position and as the lever body 504 is pivoted away from the secured position the head portion 538 engages the clasp body 506 such that as the lever body 504 is further pivoted toward the unsecured position the head portion 538 moves the interface end 540 away from the base 28. More specifically, the intermediate position of the lever body 504 may be defined at a position where the link shaft 520 and the pivot shaft 516 are at the same height, shown in FIG. 4C. At this intermediate position the head portion 538 of the pivot shaft 516 engages one of the side portions 546 of the clasp body 506 and as the lever body 504 is further pivoted toward the unsecured position the clasp body 506 pivots around the pivot shaft 516 and the interface end 540 moves away from the base 28. Alternatively, in the intermediate position movement of the lever body 504 toward the secured position causes the head portion 538 to become spaced from the clasp body 506 such that the hooked profile 550 can engage the lip 68 of the base 28.

The latch assembly 48 may further comprise a detent assembly 552 disposed on the first body 502 and abutting the lever body 504 for limiting free movement of the lever body 504 from the unsecured position and the secured position. Specifically, the detent assembly 552 may be disposed on one of the lateral faces 510 of the first body 502 and protrude in a direction generally perpendicular to the lateral face 510. Said differently, a portion of the detent assembly 552 may be raised above the surface of the lateral face 510 at a distance such that the detent assembly contacts the lever body 504.

As mentioned above, the detent assembly 552 limits free movement of the lever body 504, which is effected via engagement between the detent assembly 552 and the lever body 504. To this end, the detent assembly 552 may comprise an outwardly oriented ball 564 or other detent element, a spring (not shown), and a housing. The ball 564 is movably supported by the housing and biased toward the lever body 504 by the spring. Contact between the ball 564 and the lever body 504 may displace the ball 564 into the housing and compresses the spring. When the lever body 504 is in the secured position the ball contacts the lever body 504 at the recess 562 and when the lever body 504 is in the unsecured position the ball 564 contacts the lever body 504 at one of the edges 520. In order to move the lever body 504 away from the secured position the ball 564, being engaged with the recess 562, must be displaced further into the housing in order to disengage from the recess 562, which generally requires a greater amount of force than is required to move the lever body 504 once the ball 564 is already compressed. Similarly, when the lever body 504 is in the unsecured position, the side wall 528 begins to uncover the detent assembly 552 such that the ball 564 moves outwardly to engage the edge 530 of the side wall 528, thereby requiring the ball 564 to be again displaced inwardly when the lever body 504 is moved out of the unsecured position and increasing the force required to an amount sufficient to limit free movement.

Attaching and detaching the lid 26 from the base 28 is advantageously performed simultaneously with actuation of the latch assembly 48 because motion of the lever body 504 shares a component direction with the direction that the lid 26 moves relative to the base 28 during attaching and detaching. Owing to the configuration of the latch assembly 48, movement of the handle portion 522 to engage the lid 26 with the base 28 is continuous with pivoting of the lever body 504 from the unsecured position to the secured position, therefore the lid 26 can be coupled to the base 28 with a single motion. Specifically, with the lever body 504 in the unsecured position a user grasps the handle portion 522 and moves the lid 26 downward to engage the base 28, upon engagement of the lid and the base 28 the user continues with the downward motion to pivot the lever body 504 from the unsecured position to the secured position, thereby moving the clasp body 506 into engagement with the base 28 and securing the lid 26 to the base 28.

The latch assembly 48 is configured to effect disengaging the lid 26 from the base 28 in a similarly continuous movement. Pivoting the lever body 504 toward the unsecured position to effect disengagement of the interface end 540 of the clasp body 506 from the lip 68 of the base 28 is continuous with movement of the handle portion 522 to disengage the lid 26 from the base 28. Specifically, with the lever body 504 in the secured position as shown in FIG. 4B, a user grasps the handle portion 522 and pivots the lever body 504 toward the unsecured position as shown in FIG. 4C, causing the interface end 540 of the clasp body 506 to move downward and disengage from the lip 68. In the intermediate position, the link end 542 of the clasp body 506 has moved downward such that one of the side portions 546 contacts the head portion 538 of the pivot shaft 516. As the user continues to move the lever body 504 toward the unsecured position the handle portion 522 moves upwardly, which causes the link end 542 to correspondingly move downward. Due to the contact between the clasp body 506 and the pivot shaft 516, the interface end 540 moves outwardly away from the lip 68, and upon reaching the unsecured position as shown in FIG. 4D the user continues with the upward movement to lift the lid 26 away from the base 28. Due to the contact between the clasp body 506 and the pivot shaft 516 which causes coordinated movement between the lever body 504 and the clasp body 506, the user is not required to perform a secondary step of disengaging the interface end 540, and as such can remove and attach the lid 26 to the base 28 by only contacting the handle portion 522 of the lever body 504.

Figure 5A:
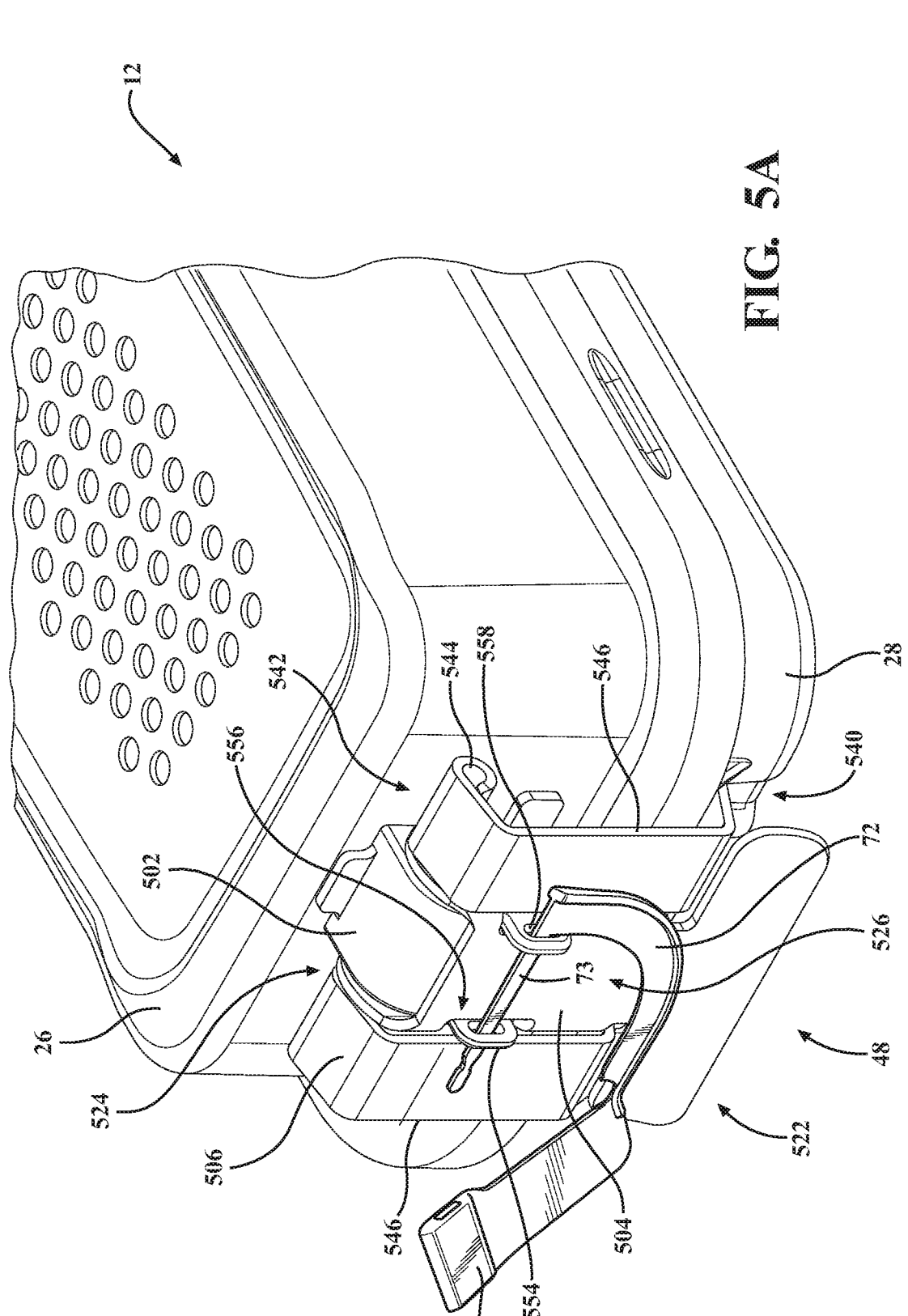
FIG. 5A and FIG. 5B are perspective views of the latch assembly in the secured position with a frangible sealing element disposed within the latch assembly.
Figure 5B:
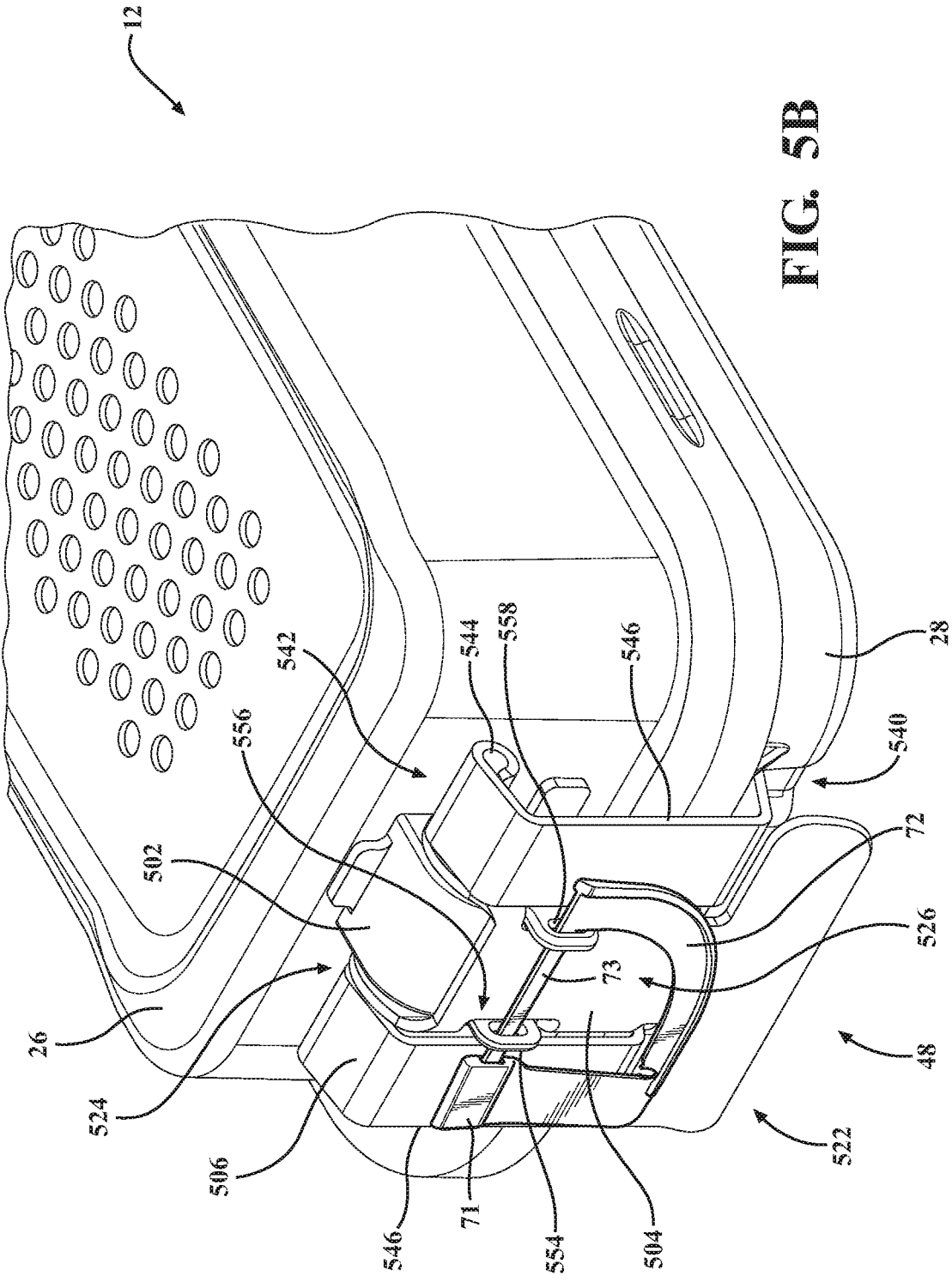
Figure 5C:
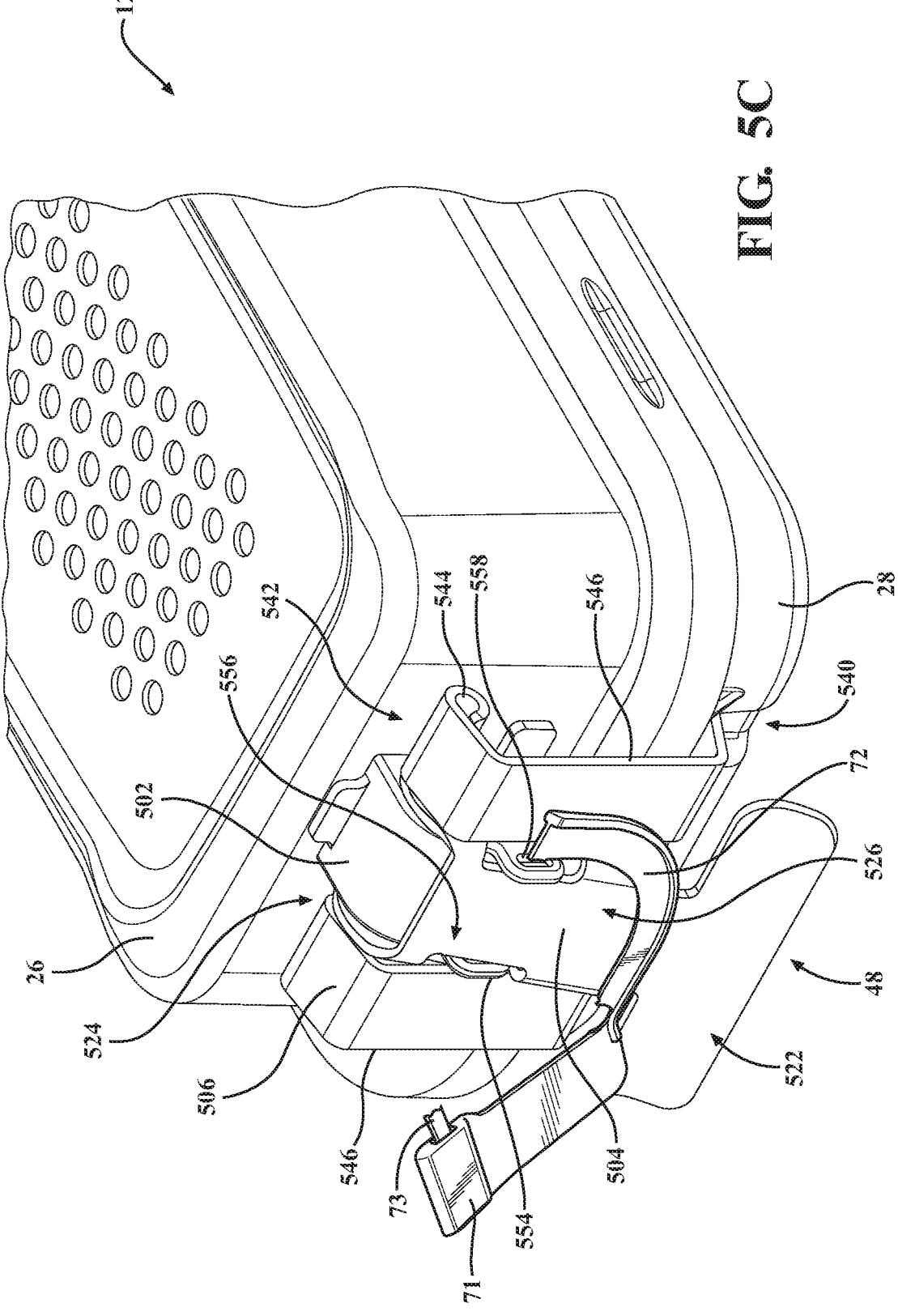
FIG. 5C is a perspective view of the latch assembly in the unsecured position and a severed frangible sealing element partially disposed within the latch assembly.

Referring now to FIGS. 5A-5C, in some instances, a frangible sealing element 72 may be coupled to the latch assembly 48. The frangible sealing element 72 may be configured to indicate whether the latch assembly 48 is in the unsecured position or the secured position. For instance, in FIGS. 5A and 5B, the latch assembly 48 is in the secured position and the frangible sealing element 72 is disposed within the latch assembly 48 and locked, indicating that the lid 26 is sealably coupled to the base 28. In FIG. 5C, the frangible sealing element 72 is sheared when the lever body 504 is moved to the unsecured position, indicating that the lid 26 is no longer sealably coupled to the base 28 and the lid 26 may be removed from the base 28.

In instances where the frangible sealing element 72 may be coupled to the latch assembly 48, such as the instances of FIGS. 5A-5C, the first body 502 may include a flange 554 extending away from the lid 26. The flange 554 may have a tab portion 556 that defines a security aperture 558. The lever body 504 may further define a shear aperture 560 arranged on the body portion 524 and extending through the front wall 526. The shear aperture 560 is arranged such that as the lever body 504 is moved toward the secured position the shear aperture 560 receives the tab portion 556 of the flange 554 and in the unsecured position the shear aperture 560 is spaced from the tab portion 556.

By moving the lever body 504 from the secured position shown in FIGS. 5A and 5B, to the unsecured position shown in FIG. 5C, the shear aperture 560 of the lever body 504 severs the frangible sealing element 72. As shown in FIGS. 5A and 5B, when the lever body 504 is moved to the secured position, the shear aperture 560 of the lever body 504 engages the tab portion 556 of the first body 502. When the lever body 504 is moved to the unsecured position, shown in FIG. 5C, the shear aperture 560 is spaced from the tab portion 556. Furthermore, the frangible sealing element 72 is disposed in the security aperture 558 of the first body 502. As such, in FIGS. 5A and 5B, the lever body 504 is moved to the secured position and the frangible sealing element 72 is disposed in the security aperture 558 and locked in place. In FIG. 5C, the frangible sealing element 72 is severed by the shear aperture 560 when the lever body 504 is moved to the unsecured position.

The frangible sealing element 72 may include any material that the shear aperture 560 can sever. For example, the frangible sealing element may include a plastic. Additionally, the frangible sealing element 72 in FIG. 5B is configured to lock. As shown, the frangible sealing element 72 may include a receiver 71 and a tab 73. As shown in FIG. 5B, the tab may be inserted into the receiver 71 and may be locked into place. However, in other instances, the frangible sealing element 72 may be disposed within the aperture 72 without locking.

FIG. 3 is a schematic diagram describing a method of removing sterile contents, such as one or more wirelessly chargeable batteries 14, housed in the autoclavable container 12 in a sterile manner. As shown, the method includes a step 80 of pivoting the handle portion 522 of the lever body 504 of the latch assembly 48 about the first body 502 fixedly coupled to the lid 26 such that the lever body 504 moves from the secured position shown in FIG. 4B to the unsecured position shown in FIG. 4D. Also during step 80, in response to pivoting the handle portion 522 of the lever body 504 from the secured position to the unsecured position, the clasp body 506 of the latch assembly 48 disengages from the base 28 of the autoclavable container 12 and moves outwardly away from the base 28. After step 80, the method then proceeds to a step 82 of lifting the lid 26 off the base 28 by lifting the lever body 504 without contacting the base 28 to provide access to the sterile contents within the volume 30 of the base 28. The method then proceeds to a step 84 of removing the sterile contents without contacting the base 28.

Figure 2B:
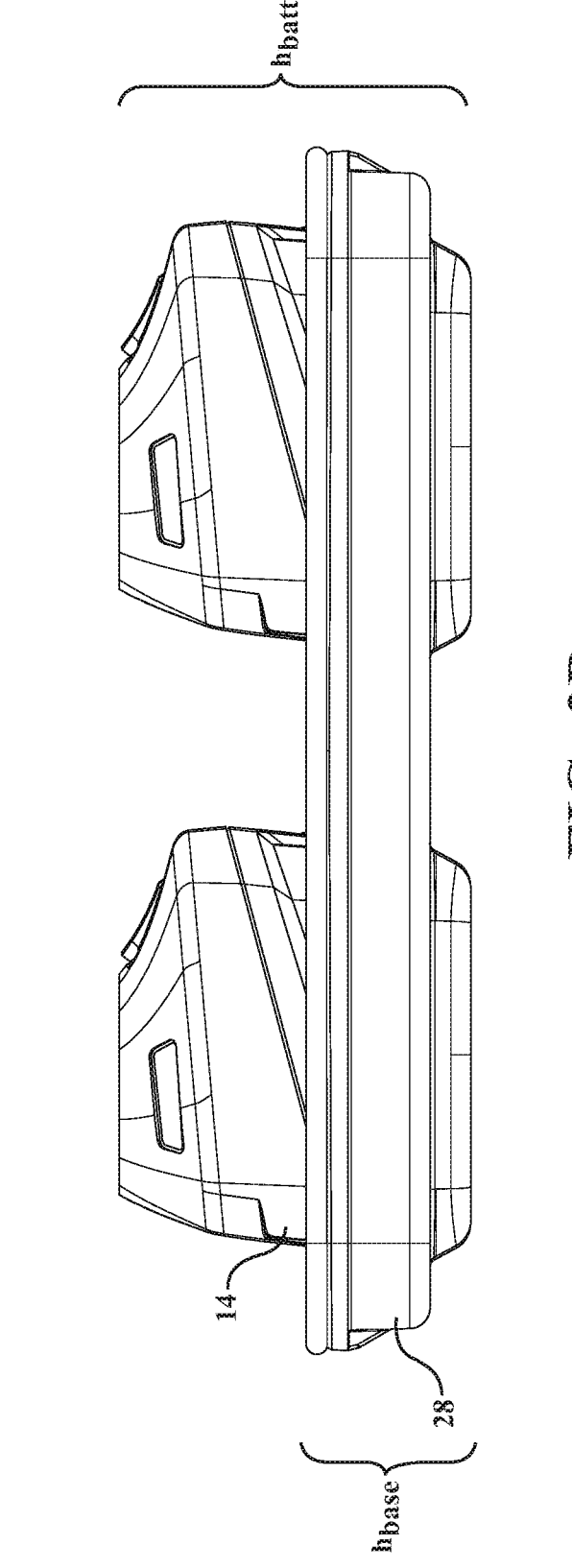
FIG. 2B is a side view of the autoclavable container wherein a lid of the autoclavable container and a base of the autoclavable container are separated and a wirelessly chargeable battery is disposed within the base.

The autoclavable container 12 may include a variety of features to aid in removing sterile contents housed in the autoclavable container 12 in a sterile manner during the above-stated method. For instance, the lever body 504 may be prevented from pivoting more than 110° from the lid 26 such that the autoclavable container 12 may be lifted by the lever body 504 during step 80. Additionally, in an instance where the sterile contents are the wirelessly chargeable battery 14, a height of the wirelessly chargeable battery 14, labelled as $h_{battery}$ in FIG. 2B, is greater than a depth of the base (which may also be referred to herein as a "height of the base"), labelled as $h_{base}$ in FIG. 2B. As such, during step 84, the wirelessly chargeable battery 14 may be removed from the autoclavable container 12 and the base 28 without contacting the base 28. In some instances, the sum of a depth of the lid 26, $h_{lid}$ in FIG. 2B, and the depth of the base 28, $h_{base}$, may be substantially equivalent to the height of the wirelessly chargeable battery 14, $h_{battery}$. In such instances, to ensure that the height of the wirelessly chargeable battery 14, $h_{battery}$, is greater than the depth of the base 28, $h_{base}$, the autoclavable container 12 is manufactured such that the depth of the lid 26, $h_{lid}$, is greater than the depth of the base 28, $h_{base}$.

In various instances, the latch assembly 48 may vary. Additionally, as previously stated, while the base 28 includes a lip 68 and the interface end 540 of the clasp body 506 includes a hooked profile 550, in other instances the interface end 540 may not include the hooked profile 550 and/or the base 28 may not include the lip 68. In such instances, the interface end 540 may be configured to engage with the base 28 via alternative means.

Figures 6A, 6B:
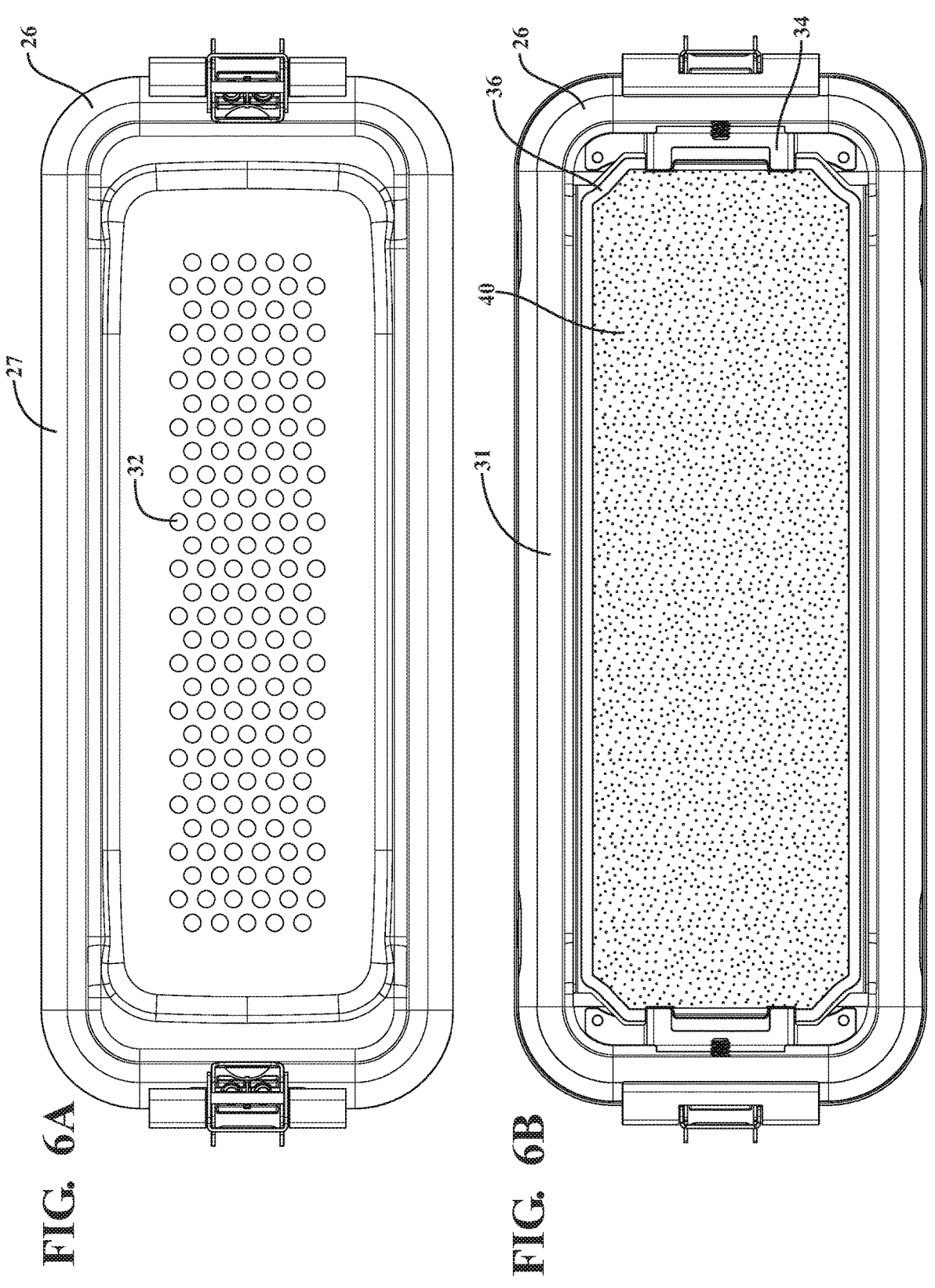
FIG. 6A is a top view of an outer surface of the lid of the autoclavable container.
FIG. 6B is a top view of an inner surface of the lid of the autoclavable container.

The autoclavable container 12 may include an aperture or a plurality of apertures 32 configured to allow a sterilant to permeate the autoclavable container 12. FIG. 6A illustrates an outer surface 27 of the lid 26 of the autoclavable container 12 and as shown, the lid 26 defines the plurality of apertures 32. Furthermore, as shown in FIG. 6B, the lid may include a mount 34 for receiving a filter 36 defining a microbial barrier 40. In FIG. 6B, the filter 36 faces an interior of the autoclavable container 12 to prevent or minimize an amount of contaminants that may otherwise enter the interior of the autoclavable container 12 through the plurality of apertures 32. For example, the filter 36 may cooperate with the lid 26 and the base 28 of the autoclavable container 12 to maintain sterility of the volume 30 after the entire autoclavable container 12 has been sterilized. Thus, the volume 30 may be maintained in a sterile state even when the autoclavable container 12 is moved to a non-sterile location, so long as the lid 26 and the base 28 remained sealed. In some instances, the base 28 may define a plurality of apertures 32 and may include a mount 34 for receiving a filter 36.

Figures 6C, 6D:
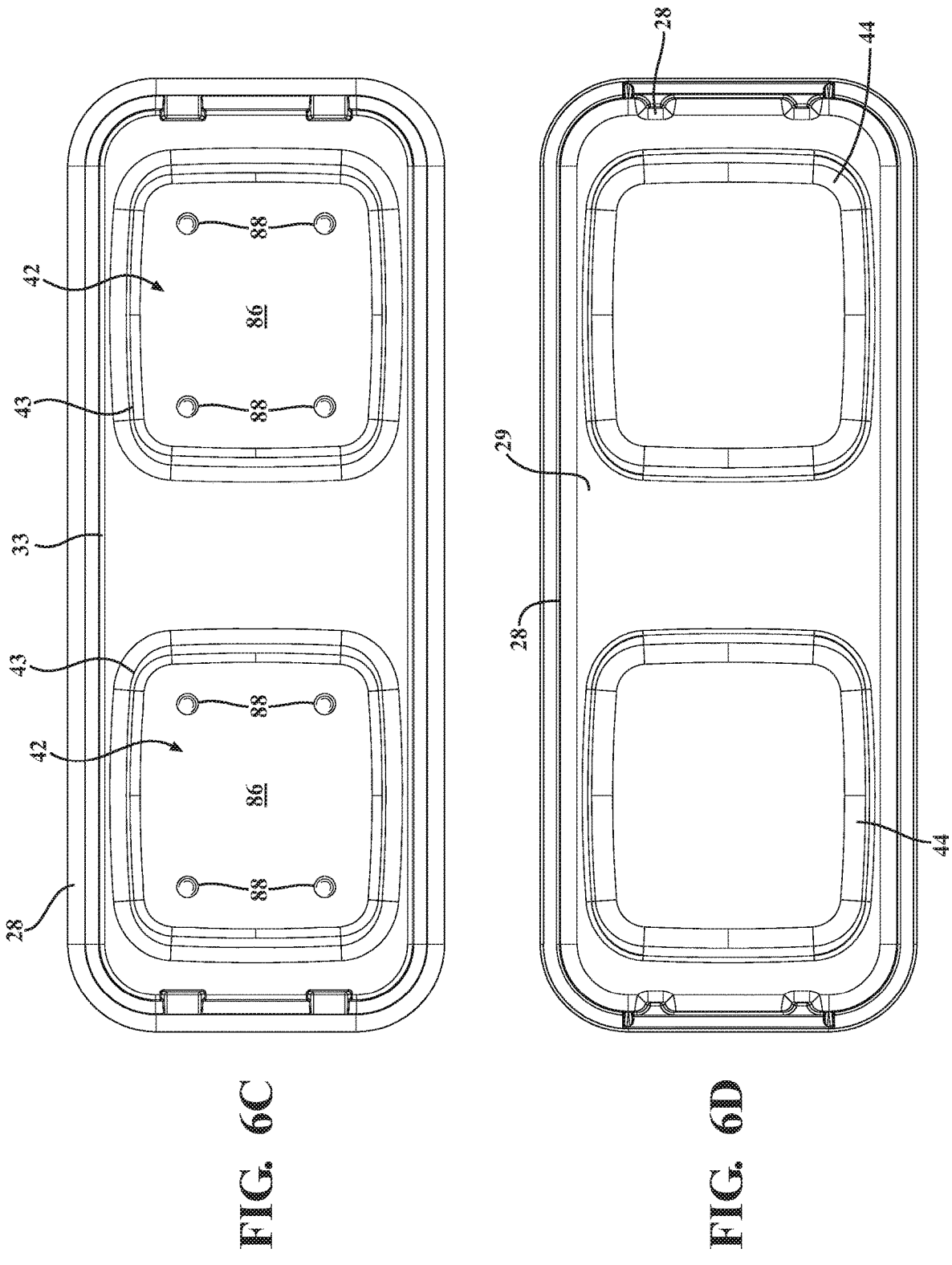
FIG. 6C is a perspective view of an inner surface of the base of the autoclavable container.
FIG. 6D is a top view of an outer surface of the base of the autoclavable container.

As shown in FIG. 6C, the base 28 of the autoclavable container 12 may include a plurality of receptacles 42 shaped to receive a wirelessly chargeable battery 14. While FIG. 6C illustrates the autoclavable container 12 having two receptacles 42, any suitable number of receptacles 42 may be provided in the autoclavable container 12 for receiving the one or more wirelessly chargeable batteries 14. For example, in one instance, the autoclavable container 12 may only include a single receptacle 42 for receiving a single wirelessly chargeable battery 14. In some instances, the autoclavable container 12 may omit the receptacles 42. Additionally, the receptacle 42 may receive a portion of the one or more wirelessly chargeable batteries 14 within walls 43 of the receptacle.

As shown in FIG. 6D, the base 28 of the autoclavable container 12 may include a plurality of protrusions 44, which may be aligned with a corresponding receptacle 42. A protrusion 44 is defined by an outer surface 27 of the autoclavable container 12 and may be aligned with a corresponding receptacle 42. For instance, the protrusions 44 in FIG. 6D are defined by an outer surface 29 of the base 28 and are aligned with a receptacle 42. As such, in an instance where a wirelessly chargeable battery 14 is inserted within a receptacle 42, the wirelessly chargeable battery 14 also becomes aligned with a corresponding protrusion 44. In some instances, the autoclavable container 12 may omit the protrusions 44.

The protrusions 44 of the base 28 allow the autoclavable container 12 to be placed on the charging module 16. As will be described further herein, the charging module 16 may include charging bays 46 (shown in FIG. 11A) shaped, i.e., inset, to receive a protrusion 44 of the autoclavable container 12. As such, each protrusion 44 is sized and shaped such that each protrusion 44 may be placed onto a corresponding charging bay 46 of the charging module 16 to align the autoclavable container 12 and contents therein on the charging module 16. As previously stated, in an instance where a wirelessly chargeable battery 14 is inserted within a receptacle 42, the wirelessly chargeable battery 14 becomes aligned with a corresponding protrusion 44. Therefore, by positioning the protrusions 44 of the autoclavable container 12 within charging bays 46 of the charging module 16, the wirelessly chargeable battery 14 is aligned with a charging bay 46, such that charging power may be transferred from the charging module 16 to the wirelessly chargeable battery 14. In some instances, the autoclavable container 12 may include a protrusion 44 even if the autoclavable container 12 does not include a receptacle 42, such that the autoclavable container 12 may be placed on the charging module 16 and aligned accordingly.

Additionally, while FIG. 6D illustrates the autoclavable container 12 having two protrusions 44 corresponding to the two receptacles 42, any suitable number of protrusions 44 may be provided on the autoclavable container 12 for placing the autoclavable container 12 on the charging module 16. For example, in one instance, the autoclavable container 12 may only include a single protrusion 44 for placing the autoclavable container 12 on the charging module 16 and for aligning a single wirelessly chargeable battery 14 with a charging bay 46. In some instances, the autoclavable container 12 may omit the protrusions 44.

Referring back to FIG. 6C, the plurality of receptacles 42 include a floor 86. Additionally, each receptacle 42 may include a plurality of standoffs 88 extending from the floor 86. For instance, in FIG. 6C, each receptacle 42 includes four standoffs 88. The standoffs 88 are configured such that a wirelessly chargeable battery 14 received by a receptacle 42 contact the standoffs 88 such that the wirelessly chargeable battery 14 is spaced from the floor 86. In this way, sterilant can be circulated underneath the wirelessly chargeable battery 14 when the autoclavable container 12 is placed in an autoclave and sterilized. This may also enable improved drying of the wireless chargeable battery 14 after the autoclave cycle is complete.

As such, in instances where the autoclavable container 12 includes a plurality of receptacles 42 including the plurality of standoffs 88, a method of sterilizing the wirelessly chargeable battery 14 may be executed. The method includes a step of positioning the wirelessly chargeable battery 14 on the plurality of standoffs 88 such that a bottom surface of the wirelessly chargeable battery 14 is spaced from the floor 86 of the receptacle; a step of placing the autoclavable container 12 in an autoclave; and a step of sterilizing the autoclavable container 12 such that a sterilant contacts the bottom surface of the wirelessly chargeable battery 14.

In various instances, a number, an arrangement, a shape, and a size of standoffs 88 may vary. For example, each receptacle 42 may include any suitable number of standoffs 88. In FIG. 6C, each receptacle 42 includes four standoffs 88, however in other instances, each receptacle 42 may include greater or lesser number of standoffs 88. Additionally, the standoffs 88 may be arranged in any suitable fashion, e.g. in a rectangular fashion as shown in FIG. 6C, a triangular fashion, a circular fashion, or any other suitable fashion. The standoffs 88 may have any shape, e.g. a spherical shape as shown in FIG. 6C, a pyramidal shape, a cuboid shape, or any other suitable shape. Additionally, the standoffs 88 may be of any suitable size. For example, the standoffs 88 may have a different size and height in comparison to the receptacle 42 than the standoffs 88 shown in FIG. 6C. Furthermore, each standoff 88 of a receptacle 42 may be of a different size, height, and may be spaced from one another such that sterilant can move between the standoffs 88. The standoffs 88 may also extend from or be disposed on a bottom surface of the wirelessly chargeable battery 14 such that the standoffs 88 contact the floor 86 of the receptacle 42 when the wirelessly chargeable battery 14 is received by a receptacle 42. Finally, the autoclavable container 12 may omit the standoffs 88.

A size of the standoffs 88 may be selected in view of sterilizing the wirelessly chargeable battery 12. For instance, a shape or a size of the standoffs 88 may be selected based on an area on a bottom surface of the wirelessly chargeable battery 14 contacted by the standoffs 88 such that the sterilant is able to contact most of the bottom surface of the wirelessly chargeable battery 14. For example, the area on the bottom surface of the wirelessly chargeable battery 14 contacted by the standoffs 88 may be less than 25%, 20%, 15%, 10%, or 5% of the area of the bottom surface of the wirelessly chargeable battery 14. As such, a majority of a bottom surface of the battery is exposed to the sterilant during the autoclave process. Specifically, greater than 75%, 80%, 85%, 90%, or 95% of the area of the bottom surface may be exposed to the sterilant.

A height of the standoffs 88 may be selected in view of charging the wirelessly chargeable battery 12. As previously stated, the power antenna 194 of the wirelessly chargeable battery 14 is placed within a proximity of the induction coil 130 of the charging module 16. In some instances, the smaller the distance between the power antenna 194 and the induction coil 130, the more efficiently the induction coil 130 is able to transfer charging power to the power antenna 194. In other instances, there is a threshold distance between the power antenna 194 and the induction coil 130 such that the induction coil 194 less efficiently transfers charging power to the power antenna 194 at distances greater than the threshold distance. In both instances, the height of the standoffs 88 may be selected accordingly. For example, the height of the standoffs 88 may be minimized in order to maximize efficiency of the charging power transfer between the power antenna 194 and the induction coil 130, while still allowing sterilant to contact the bottom surface of the wirelessly chargeable battery 14. As another example, the height of the standoffs 88 may be selected based on the threshold distance in order to preserve an efficiency of the charging power transfer between the power antenna 194 and the induction coil 130, while still allowing sterilant to contact the bottom surface of the wirelessly chargeable battery 14. For instance, the height of the standoffs 88 may be no greater than 4 millimeters to allow sterilant to contact the bottom surface of the wirelessly chargeable battery 14 and preserve an efficiency of charging power transfer of greater than 10%, 25%, 50%, 75%, or 90%.

Figures 6E, 6F:
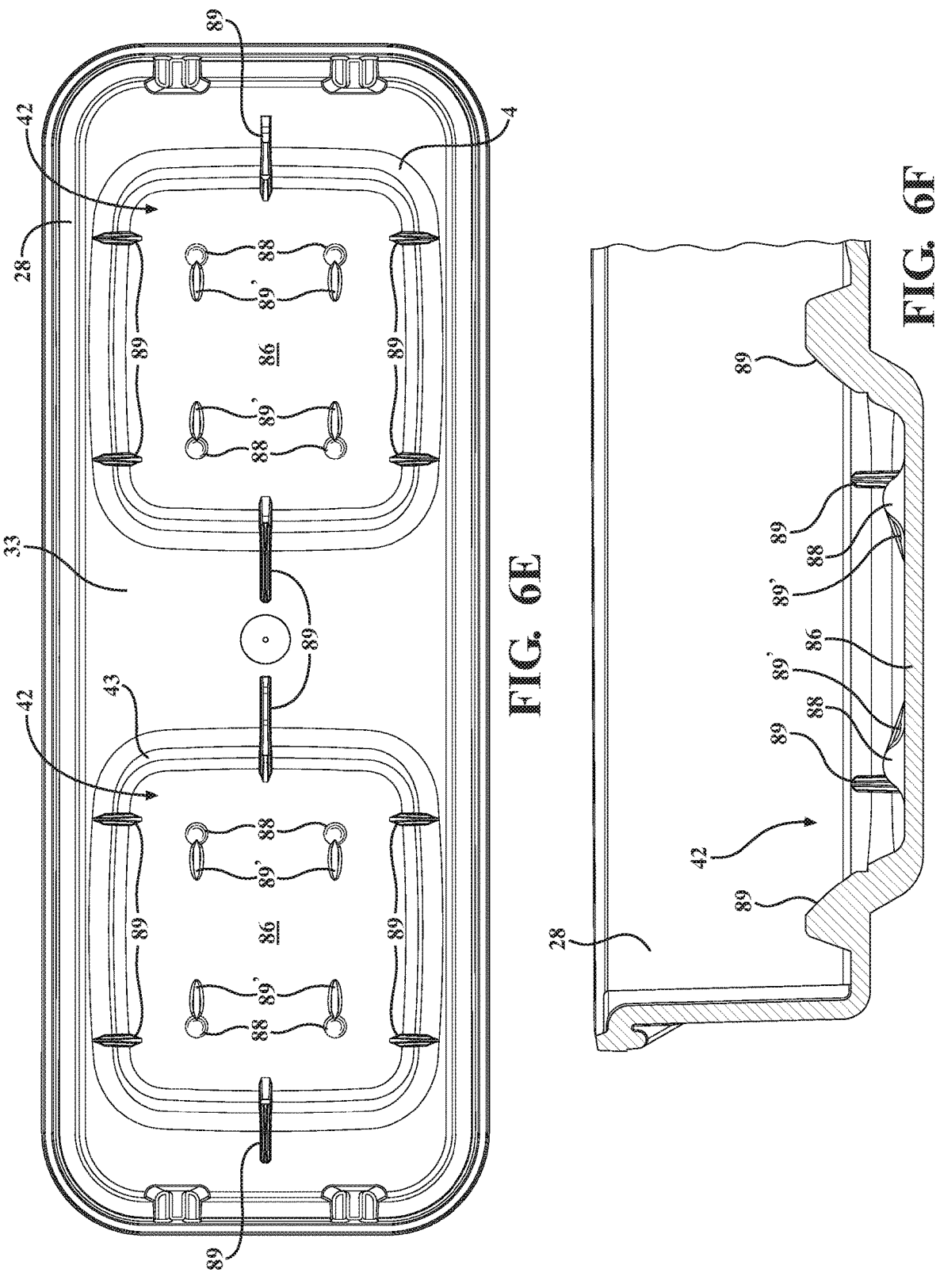
FIG. 6E is a perspective view of an inner surface of the base of the autoclavable container including alignment features.
FIG. 6F is a partial side view of the inner surface of the base of the autoclavable container including alignment features.

The autoclavable container 12 may also include alignment features, such as a web 89, shown in FIGS. 6E-6F. The web 89 is configured to align the wirelessly chargeable battery 14 within a receptacle 42 such that the power antenna 194 and the induction coil 130 are aligned when the receptacle 42 receives the wirelessly chargeable battery 14 and the autoclavable container 12 is disposed on the wireless charging device 16.

In FIG. 6E, the base 28 includes the web 89 extending between the floor 86 and the inner surface 33. When the receptacle 42 receives the wirelessly chargeable battery 14 and the autoclavable container 12 is disposed on the wireless charging device 14, the housing of the wirelessly chargeable battery 14 contacts the web 89 such that power antenna 194 and the induction coil 130 are aligned. In FIG. 6E, the web 89 is sloped downward from the inner surface 33 to the floor 86.

In FIGS. 6E and 6F, the base 28 also includes additional alignment features, such as ramps 89' that extend between the floor 86 and the standoffs 88. As shown, the receptacle 42 comprises a plurality of standoffs 88 corresponding to a plurality of ramps 89'. Each ramp 89' extends between the floor 86 and a corresponding standoff 88. As shown, the ramps 89' of FIG. 6F are sloped downward from a peak of the standoff 88 to the floor 86. In some instances, the base 28 may include the ramps 89' and omit the web 89 that extends between the floor 86 and the inner surface 33

The ramps 89' are configured to align the wirelessly chargeable battery 14 within the receptacle 42 such that the power antenna 194 and the induction coil 130 are aligned when the receptacle 42 receives the wirelessly chargeable battery 14 and the autoclavable container 12 is disposed on the wireless charging device 16. In some instances, the ramps 89' align a wirelessly chargeable battery 14 that is disposed within the receptacle 42 but is not aligned properly (the power antenna 194 and the induction coil 130 are not aligned). For example, the wirelessly chargeable battery 14 may be disposed in the receptacle 42 such that a corner of the wirelessly chargeable battery 14 is disposed between the standoffs 88 and the wirelessly chargeable battery 14. In such an instance, the wireless chargeable battery 14 contacts at least one of the ramps 89' and, when the autoclavable container 12 is moved, the wirelessly chargeable battery 14 may slide along the at least one ramp 89' until the wirelessly chargeable battery 14 is no longer contacting the ramps 89'. When the wirelessly chargeable battery 14 is no longer contacting the ramps 89', the power antenna 194 and the induction coil 130 are aligned.

Figure 6G:
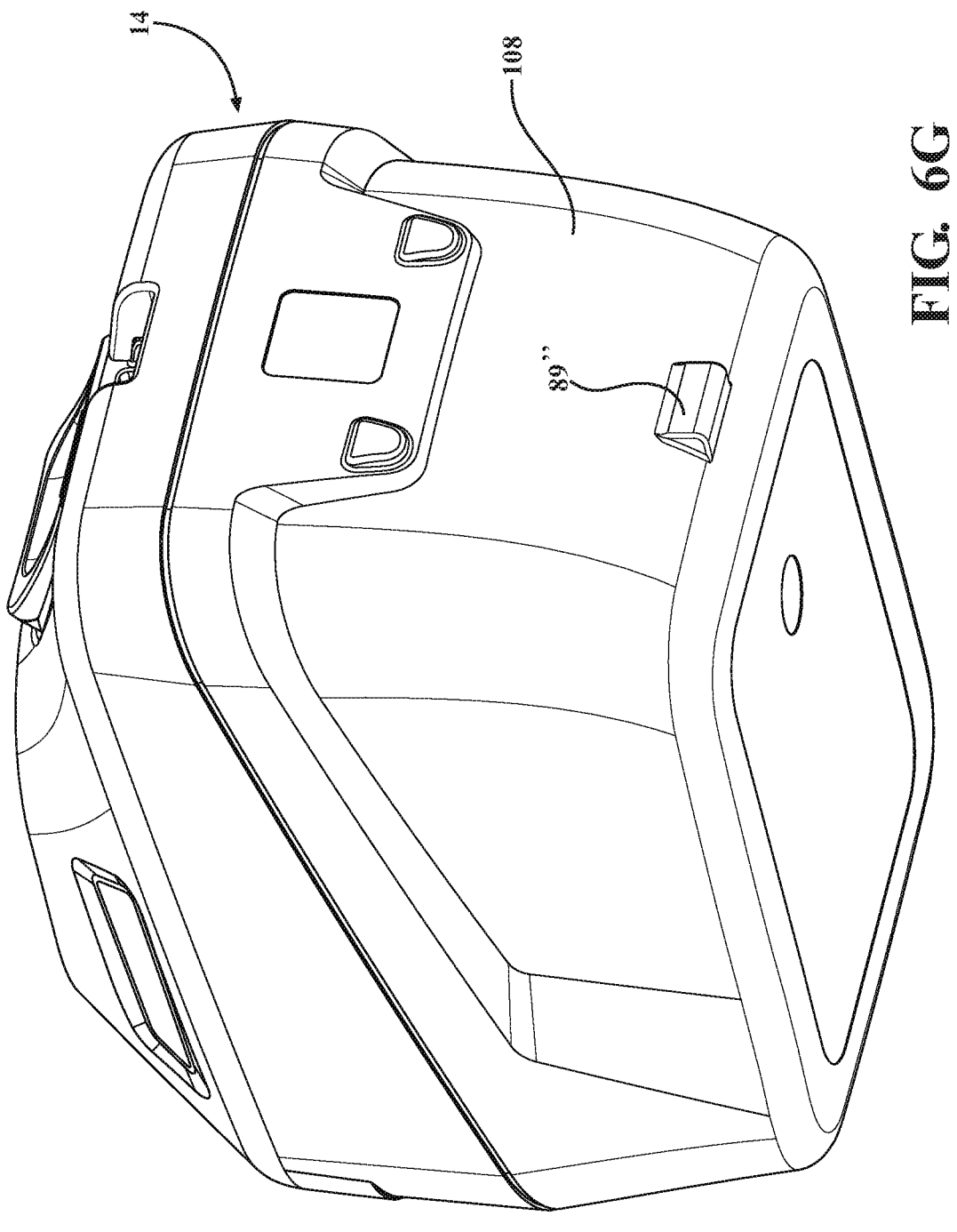
FIG. 6G is a perspective view of the wirelessly chargeable battery including an alignment feature.

In FIG. 6G, the wirelessly chargeable battery 12 includes an alignment feature, such as the rib 89" protruding from a housing 108 of the wirelessly chargeable battery 12. In instances where the base 28 does not include the web 89, the rib 89" of the wirelessly chargeable battery 12 contacts the receptacle 42 and aligns the wirelessly chargeable battery 14 within the receptacle 42. In instances where the base 28 also includes the web 89, the rib 89" of the wirelessly chargeable battery 12 and the web 89 of the base 28 cooperate to align the wirelessly chargeable battery 12 within the receptacle 42.

It should be noted that the base 28 may include any number of alignment features. In other instances, other components of the autoclavable container 12 may also include alignment features. For example, the lid 26 may additionally or alternatively include a web such that the power antenna 194 and the induction coil 130 are aligned when the lid 26 is coupled to the base 28 and the autoclavable container 12 is disposed on the wireless charging device 14.

In some instances, a removable tray may be disposed within the autoclavable container 12. For example, in the instance of FIGS. 7A and 7B, a removable tray 90 is disposed within the base 28. In such instances, one or more wirelessly chargeable batteries 14 may be placed on the removable tray 90 such that the removable tray 90 receives the wirelessly chargeable batteries 14, and the removable tray 90 may be disposed within the autoclavable container 12 to dispose the wirelessly chargeable batteries 14 within the base 28. The removable tray 90 may be removed from autoclavable container 12, as shown in FIG. 7C, to remove the wirelessly chargeable batteries 14 from the base 28. As such, the removable tray 90 allows the one or more wirelessly chargeable batteries 14 to be disposed within the autoclavable container 12 prior to being sterilized and for the one or more wirelessly chargeable batteries 14 to be removed from the autoclavable container 12 after the one or more wirelessly chargeable batteries 14 are sterilized.

Figure 7A:
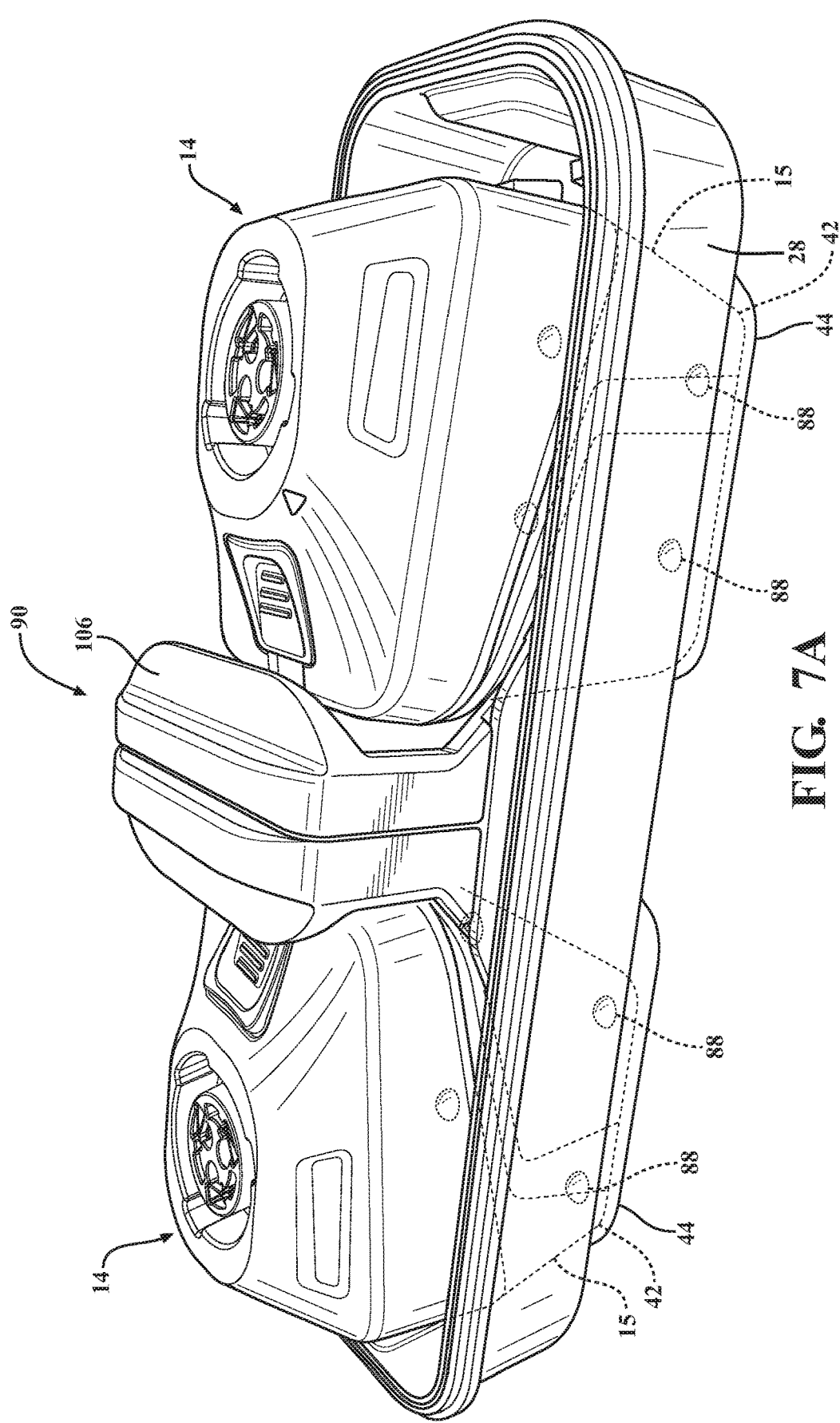
FIG. 7A is a perspective view of a removable tray and wirelessly chargeable batteries disposed within the base of the autoclavable container.
Figure 7B:
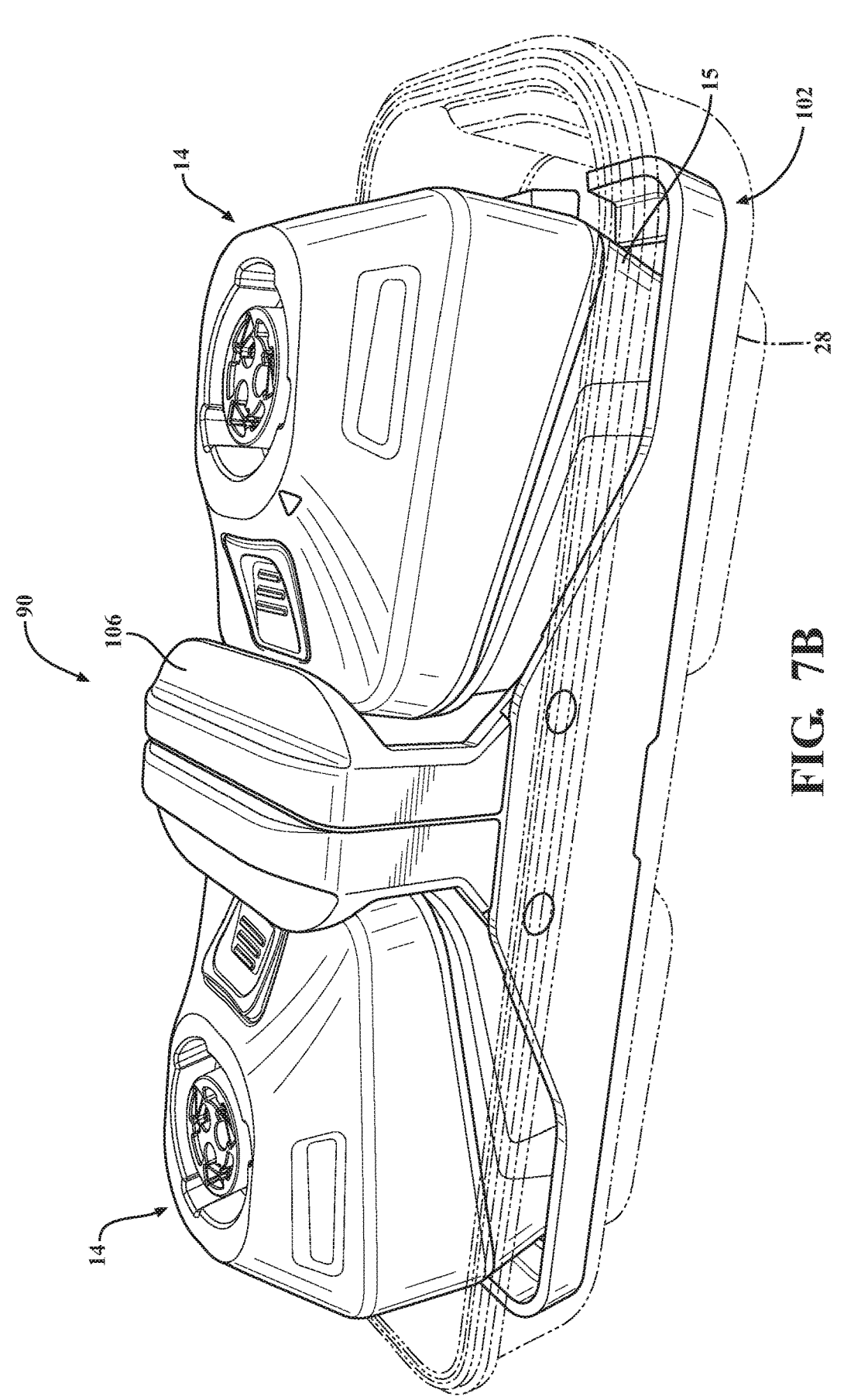
FIG. 7B is a perspective view of the removable tray and wirelessly chargeable batteries disposed within the base of the autoclavable container, the base of the autoclavable container shown in phantom.
Figure 7C:
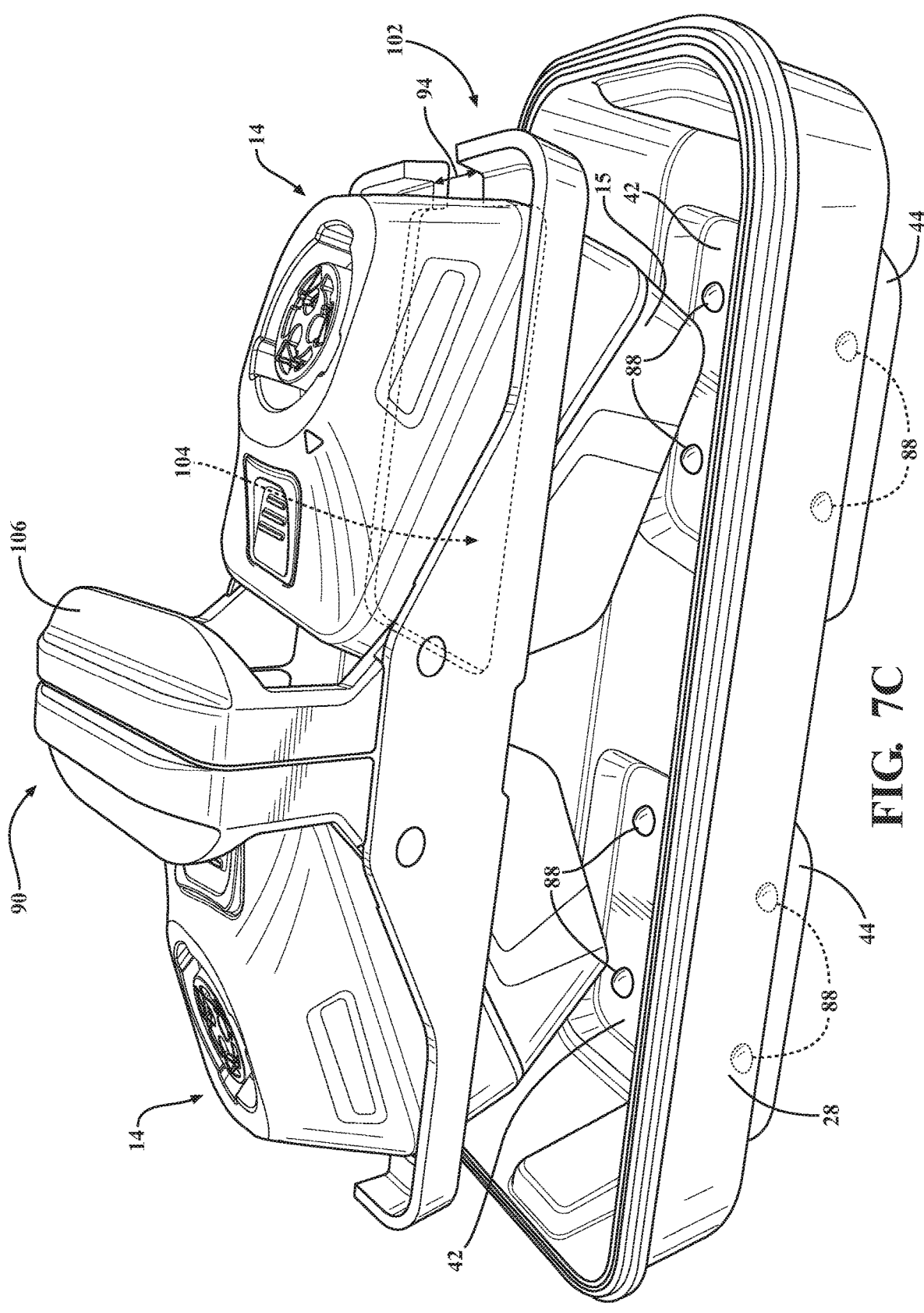
FIG. 7C is a perspective view of the removable tray and wirelessly chargeable batteries being removed from the base of the autoclavable container.
Figure 7D:
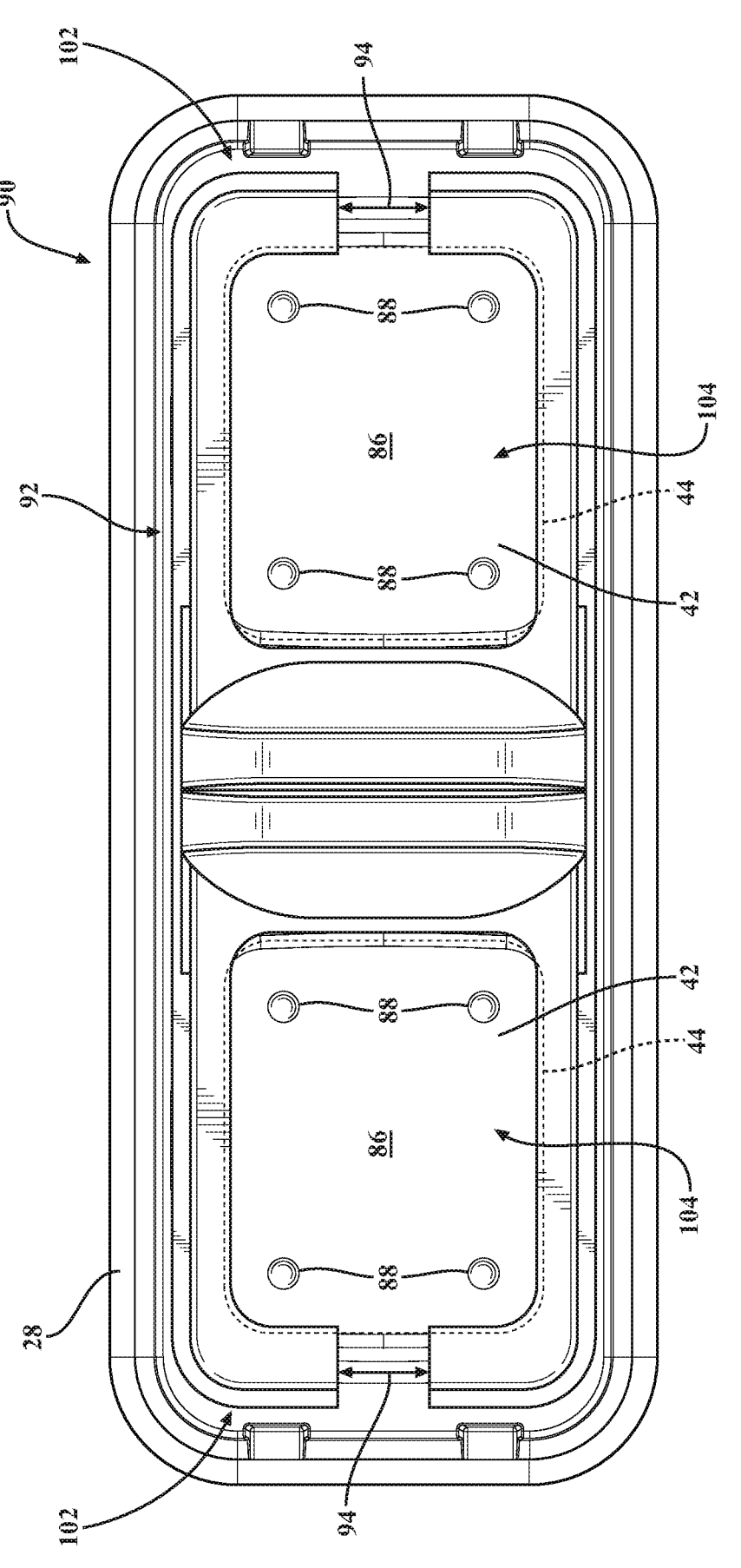
FIG. 7D is a top view of the removable tray disposed with the base of the autoclavable container.

As shown in FIG. 7D, the removable tray 90 includes a periphery 92, which includes an opening 94. As such, the periphery 92 of the removable tray 90 may be referred to as an open periphery 92. The removable tray 90 may include any suitable number of openings 94. As shown in FIG. 7D, the removable tray 90 includes two openings 94. The opening 94 permits transmission of electromagnetic waves, even if the removable tray 90 includes a material that may inhibit transmission of electromagnetic waves, such as a metal. The opening 94 may be of any size suitable for permitting the transmission of electromagnetic waves.

Figures 7E, 7F:
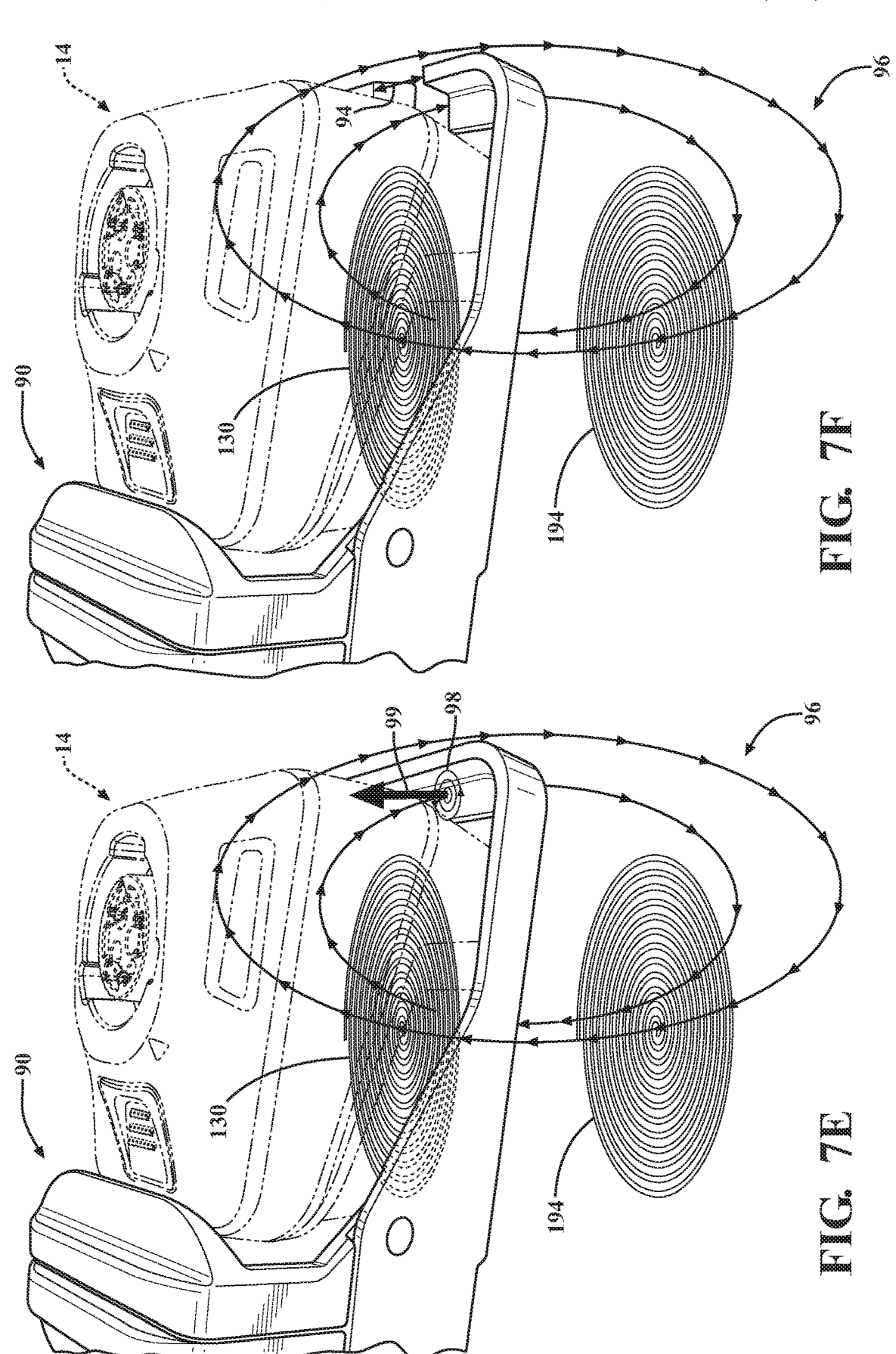
FIG. 7E is a diagrammatic view of a magnetic field generated by the charging module and a removable tray that does not include an opening.
FIG. 7F is a diagrammatic view of a magnetic field generated by the charging module and a removable tray including an opening.

FIGS. 7E and 7F illustrate how the opening 94 permits the transmission of electromagnetic waves in instances where the removable tray 90 includes a material that may inhibit transmission of electromagnetic waves. To illustrate how the opening 94 permits the transmission of electromagnetic waves, an induction coil 130 of the wirelessly chargeable battery 14 is shown, the induction coil 130 being configured to receive charging power. Additionally, a power antenna 194 of a charging bay 46 of the charging module 16 is shown, the power antenna 194 being configured to transmit charging power to the wirelessly chargeable battery 14 when the induction coil 130 is within a proximity of the power antenna 194. In FIGS. 7E and 7F, the power antenna is illustrated as a charging coil. Furthermore, the removable tray 90 in FIG. 7E does not include the opening 94 and, as such, the periphery 92 is not an open periphery. In contrast, the removable tray 90 in FIG. 7F includes the opening 94 and the open periphery 92.

Additionally, magnetic field lines are shown in FIGS. 7E and 7F to illustrate a magnetic field 96 generated by the power antenna 194. The power antenna 194 generates the magnetic field 96, which induces a current in the induction coil 130 of the wirelessly chargeable battery 14, providing charging power to the wirelessly chargeable battery 14. The relationship between the magnetic field 96 and the induced current in the induction coil 130 being that the greater an intensity of the magnetic field 96, the greater a magnitude of the induced current in the induction coil 130. When the magnetic field 96 flows through a material that inhibits transmission of electromagnetic waves, the magnetic field 96 induces eddy currents, such as the eddy currents 98 shown in FIG. 7E. In response, the eddy currents 98 generate a magnetic field 100, which opposes the direction of the magnetic field 96, attenuating an intensity of an overall magnetic field flowing through the indicative coil 130.

Accordingly, because the intensity of an overall magnetic field flowing through the induction coil 130 is attenuated, the magnitude of the induced current in the induction coil 130 decreases, providing less charging power to the wirelessly chargeable battery 14.

In FIGS. 7E and 7F, the magnetic field 96 flows through the removable tray 90, which, as previously stated, may include a material that inhibits transmission of electromagnetic waves. However, because the periphery 92 of the removable tray 90 in FIG. 7E does not include the opening 94 and the periphery 92 of the removable tray 90 in FIG. 7F does include the opening 94, more of the magnetic field 96 flows through the removable tray 90 and the wirelessly chargeable battery 14 receives more charging power. To explain, when the magnetic field 96 flows through the removable tray 90 of FIG. 7E, more eddy currents, such as the eddy currents 98 shown in FIG. 7E, are induced by the magnetic field 96 and less charging power is provided to the wirelessly chargeable battery 14. This is because the eddy currents 98 generate an induced magnetic field 99 that opposes the direction of the magnetic field 96. Therefore, because the opening 94 of the periphery 92 permits the transmission of electromagnetic waves, such as the magnetic field 96 generated by the power antenna 194, fewer eddy currents 98 are generated and more charging power is provided to the wirelessly chargeable battery 14 (in comparison to an instance where the removable tray 90 does not include the opening 94, such as FIG. 7E).

In FIG. 7D, the removable tray 90 includes a support member 102 defining a void 104 adjacent the opening 94. Referring to FIG. 7C, the void 104 may be sized to receive a portion of the wirelessly chargeable battery 14. As shown, the void 104 is sized such that the portion 15 of the chargeable battery 14 received by the removable tray 90 is below the support member 102 when the removable tray 90 is removed from the autoclavable container 12. The removable tray 90 may include any suitable number of support members 102 and corresponding voids 104. For example, in FIG. 7D, the removable tray 90 includes two support members 102 and two corresponding voids 104 configured to receive two wirelessly chargeable batteries 14.

In instances where the base 28 includes a protrusion 44, the void 104 may be positioned directly above the protrusion 44 when the removable tray 90 is disposed within the base 28. In FIG. 7D, an outline of the protrusion 44 is shown in phantom and the void 104 is illustrated as being positioned directly above the protrusion 44. In this way, the wirelessly chargeable battery 14 received by the void 104 is positioned directly above the protrusion 44 when the removable tray 90 is disposed within the base 28. As previously stated, the protrusions 44 are positioned within charging bays 46 of the charging module 16. As such, the wirelessly chargeable battery 14 received by the removable tray 90 is aligned with a charging bay 46 when the removable tray 90 is disposed within the base 28 such that charging power may be transferred from the charging module 16 to the wirelessly chargeable battery 14.

In instances where the base 28 defines a receptacle 42 shaped to receive a wirelessly chargeable battery 14, the void 104 may be positioned directly above the receptacle 42 when the removable tray 90 is disposed within the base 28, as shown in FIG. 7D. In this way, the wirelessly chargeable battery 14 received by the void 104 is received by the receptacle 42 when the removable tray 90 is disposed within the base 28. For example, in FIG. 7A, the wirelessly chargeable batteries 14 are received by the receptacles 42 when the removable tray 90 is disposed within the base 28.

As previously stated, the receptacles 42 are aligned with the protrusions 44 such that a wirelessly chargeable battery 14 inserted within a receptacle 42 also becomes aligned with a corresponding protrusion 44. As such, the wirelessly chargeable battery 14 received by the removable tray 90 is received by a receptacle 42, aligned with a corresponding protrusion 44, and aligned with a charging bay 46 when the removable tray 90 is disposed within the base 28 such that charging power may be transferred from the charging module 16 to the wirelessly chargeable battery 14.

In instances where the base 28 defines a receptacle 42, the receptacle 42 may also include the previously-described floor 86 and the previously-described standoff 88, as shown in FIGS. 7A, 7C, and 7D. In such instances, the void 104 may be positioned directly above the receptacle 42 when the removable tray 90 is disposed the base 28, as shown in FIG. 7D. In this way, the wirelessly chargeable battery 14 received by the void 104 is received by the receptacle 42 and contacts a standoff 88 when the removable tray 90 is disposed within the base 28, as shown in FIG. 7A. As such, when the removable tray 90 is disposed within the base 28, the wirelessly chargeable battery 14 is received by a receptacle 42 and charging power may be transferred from the charging module 16 to the wirelessly chargeable battery 14. Furthermore, the wirelessly chargeable battery 14 is spaced from the floor 86 of the receptacle 42 to allow circulation of a sterilant underneath the wirelessly chargeable battery 14.

As previously stated, the void 104 may be sized such that a portion of a wirelessly chargeable battery 14 may be disposed within the void 104. For example, in FIG. 7C, the portion 15 of a wirelessly chargeable battery 14 is disposed within the void 104 of the removable tray 90. In such an instance, the receptacle 42 receives the portion 15 of the wirelessly chargeable battery 14, as shown in FIG. 7A, and the wirelessly chargeable battery 14 is disposed on the plurality of standoffs 88 when the removable tray 90 is disposed in the base 28. In instances where the base 28 does not include the plurality of standoffs 88 and a wirelessly chargeable battery 14 may be disposed within the void 104, the void 104 may be sized such that the portion 15 of the wirelessly chargeable battery 14 received by the removable tray 90 is received by a receptacle 42 and spaced from the floor 86 of the receptacle 42. As such, in instances where the base 28 does not include the plurality of standoffs 88, a size of the void 104 may still allow circulation of a sterilant underneath the wirelessly chargeable battery 14.

FIG. 7C illustrates an instance where the removable tray 90 is removed from the base 28 and the removable tray 90 removes a wirelessly chargeable battery 14 received by the removable tray 90 from the base 28. As shown in FIG. 7C, the support member 102 of the removable tray 90 contacts the wirelessly chargeable battery 14 when the removable tray 90 is removed from the base 28. In this way, the wirelessly chargeable battery 14 is removed from the base 28 when the removable tray 90 is removed from the base 28.

It should be noted that FIG. 7C also illustrates an instance where the removable tray 90 is being disposed within the base 28. As such, the support member 102 of the removable tray 90 also contacts the wirelessly chargeable battery 14 when the removable tray 90 is being disposed within the base 28.

In some instances, such as the instance of FIG. 7B, when the removable tray 90 and the wirelessly chargeable battery 14 received by the removable tray 90 are disposed within the base 28, the wirelessly chargeable battery 14 are received by the receptacle 42 and the removable tray 90 contacts the base 28 and no longer contacts the wirelessly chargeable batteries 14. For example, as shown in FIG. 7B, the support member 92 no longer contacts the wirelessly chargeable battery 14 when the removable tray 90 is disposed within the base 28. Additionally, the portion 15 of the wirelessly chargeable battery 14 is no longer below the support member 92. As such, when the removable tray 90 is removed from the base 28, the removable tray 90 contacts the wirelessly chargeable battery 14 to remove the wirelessly chargeable batteries 14 from the base 28.

Advantageously, because the removable tray 90 contacts the wirelessly chargeable battery 14 when the removable tray 90 is removed from or being disposed within the base 28, a user need not physically contact the wirelessly chargeable battery 14. Therefore, a user does not risk compromising a sterile state of the wirelessly chargeable battery 14 when the wirelessly chargeable battery 14 is removed from or being disposed within the base 28.

The removable tray 90 may also include a variety of features. For example, as shown in FIGS. 7A-7D, the removable tray 90 may include one or more handles 106 that enable the removable tray 90 to be easily grasped and disposed within and removed from the autoclavable container 12. In some instances, the removable tray 90 may define a plurality of apertures, which allow a sterilant to circulate within the autoclavable container 12. In this way, the removable tray 90 does not inhibit circulation of a sterilant when the autoclavable container 12 is placed in an autoclave and sterilized.

In some instances, at least a portion of the autoclavable container 12 is at least partially transparent, translucent, and/or non-opaque to enable a user to view the wirelessly chargeable batteries 14 within receptacles 42 and/or a status of batteries 14. For example, in some instances, the wirelessly chargeable batteries 14 may include a battery status indicator, such as an LED, that indicates a state of charge and/or a state of health of battery. In such instances, the autoclavable container 12 may include a transparent portion or the autoclavable container 12 may be at least partially transparent, such that the battery status indicator may be viewable through the transparent portion when the wirelessly chargeable battery 14 is placed within a receptacle 42.

An example wirelessly chargeable battery 14 is shown in FIGS. 8A-8E. As shown, in FIG. 8A, the wirelessly chargeable battery 14 includes a housing 108. The housing 108 includes a top portion 110 and a bottom portion 112. The top portion 110 and the bottom portion 112 may be sealably coupled such that the top portion 110 and the bottom portion 112 form an autoclavable housing.

Figure 8A:
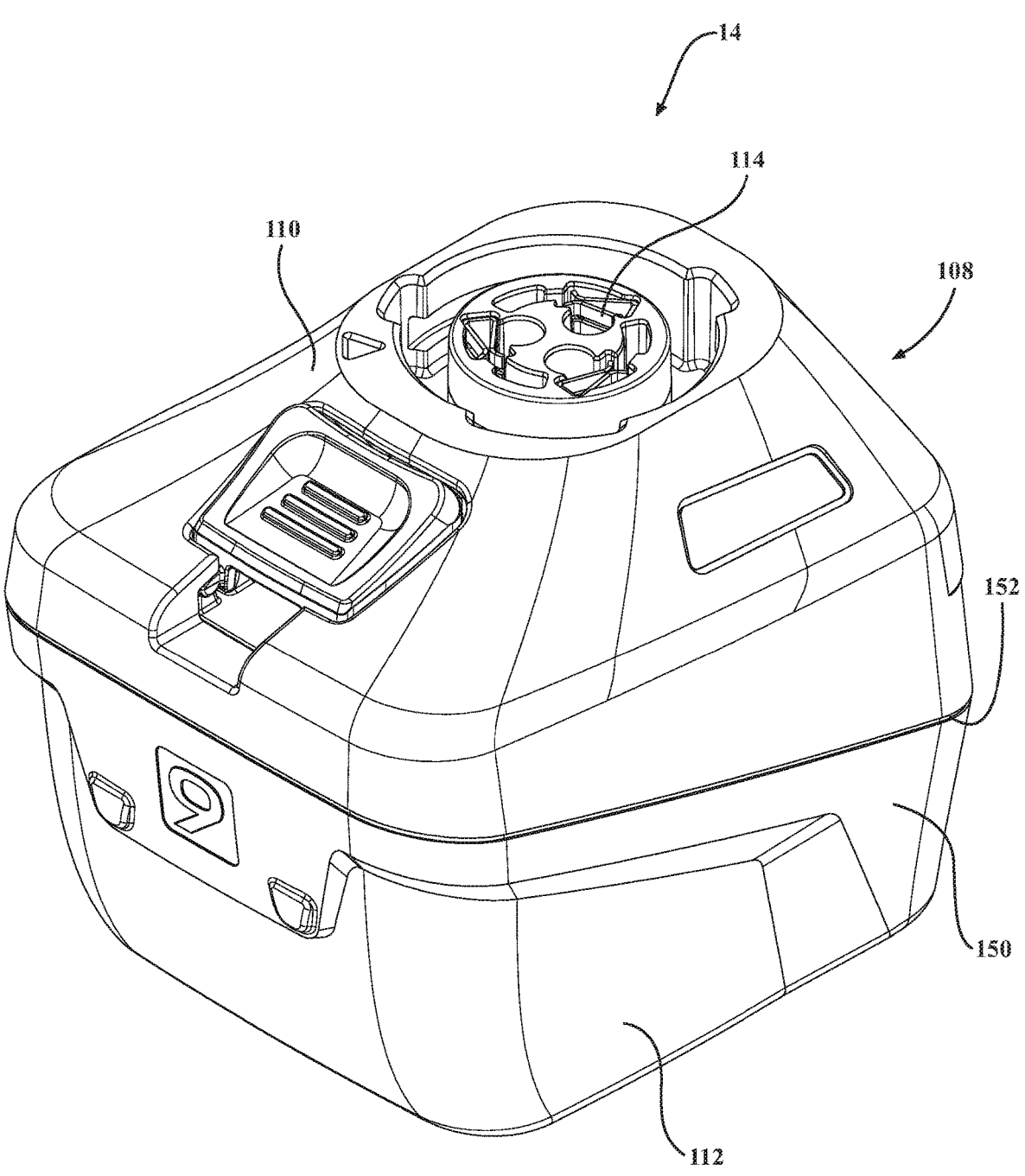
FIG. 8A is a perspective view of the wirelessly chargeable battery.
Figure 8B:
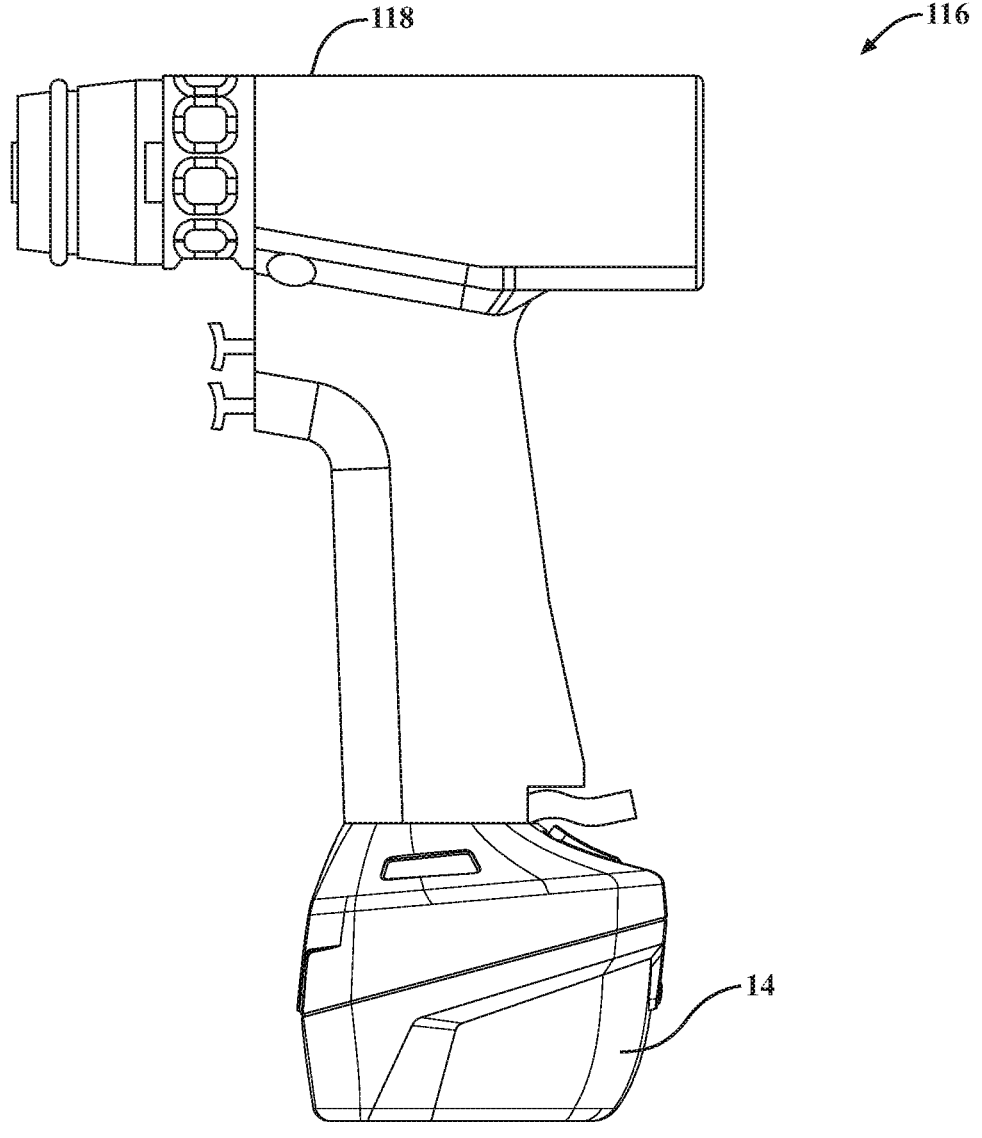
FIG. 8B is a side view of a tool coupled to the wirelessly chargeable battery.

The top portion 110 may be formed with a battery head 114. The battery head 114 may be dimensioned to fit in the aft end of a tool housing 118 of a surgical tool 116, as shown in FIG. 8B. The surgical tool 116 is further described in PCT International Application No. PCT/US2018/052854, entitled "SYSTEM AND METHOD FOR WIRELESSLY CHARGING A MEDICAL DEVICE BATTERY", the disclosure of which is incorporated herein by reference.

Figure 8C:
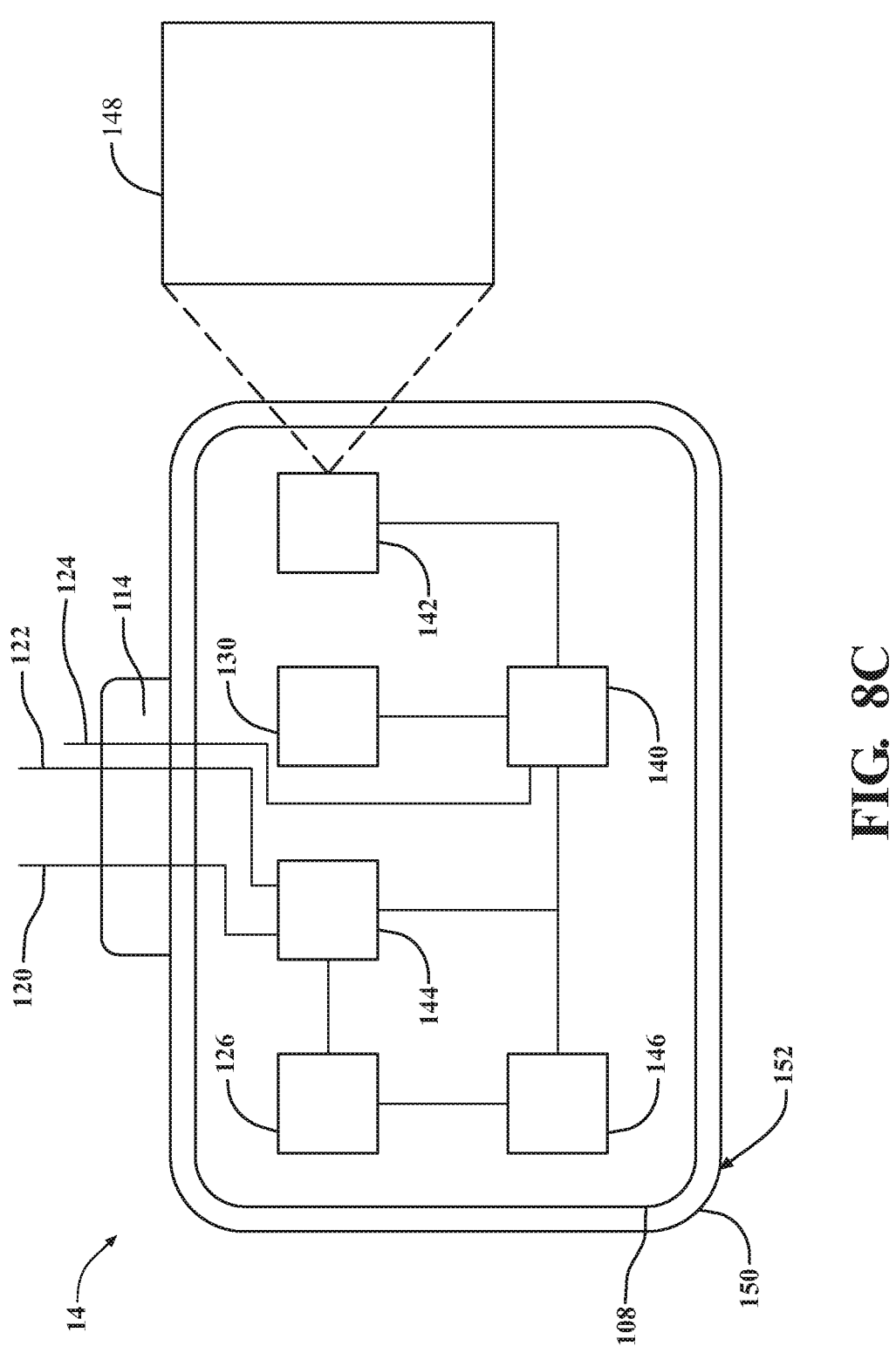
FIG. 8C is a block diagram view of the wirelessly chargeable battery.

The components of the wirelessly chargeable battery 14 described herein may be positioned within the housing 108. As shown in FIGS. 8A and 8C, the housing 108 may include a cover 150, that may be welded to the housing 108 to form a unitary structure to form a seamless bond. In addition, a seal 152, also shown in FIGS. 8A and 8C, may be positioned between housing 108 and cover 150 to form a hermetic barrier between cover 150 and housing 108. The seal 152 may be formed of a material that is autoclavable and, optionally, compressible. For example, seal 152 may include EPDM rubber or silicon rubber.

The housing 108 of the wirelessly chargeable battery 14 may include a material suitable for autoclave cycles. The wirelessly chargeable battery 14, including components of the wirelessly chargeable battery 14 positioned within the housing 108, the housing 108, the power contacts 120, 122, and the cover 150, is configured to be sterilized together with or separately from the tool 116, via steam sterilization, hydrogen peroxide sterilization, or other suitable sterilization techniques. By "sterile," it is meant that, once the process is complete, the housing 108 or the cover 150 has a sterilization assurance level (SAL) of at least $10^{-6}$. This means that there is equal to or less than one chance in a million that a single viable microorganism is present on the sterilized item. This definition of sterile is the definition set forth in the ANSI/AAMI ST35-1966, entitled "Safe Handling and Biological Decontamination of Medical Devices in Health Care Facilities and Nonclinical Settings". For alternative applications, the "sterilization" process is sufficient if, once the process is complete, the housing 108 or the cover 150 has an SAL of at least $10^{-4}$.

Also, while many versions of the wirelessly chargeable battery 14 include a housing 108 or a cover 150 that is autoclavable, that need not always be the case. This feature is often not part of the design of a battery that is not designed for medical/surgical use. Likewise, the features of this wirelessly chargeable battery 14 may be incorporated into what is often referred to as a non-sterile battery in an aseptic housing. A non-sterile battery in an aseptic housing includes a cell cluster and a circuit board to which the electrical components such as the cell regulator (voltage regulator), the transistors (e.g., FETS), the resistors, capacitors, and microprocessor or battery controller are monitored. This cell cluster is not autoclavable. Instead, the cell cluster can be removably fitted into a housing that is autoclavable. Once the cell is fitted in the housing, the housing is sealed. The cells and other cluster-forming components are thus encapsulated in a sterilized enclosure. Contacts integral with both the cell cluster and the housing provide the contact path over which current is sourced from the battery. A further understanding of the structure of a non-sterile battery assembly in an aseptic housing can be obtained from U.S. Pat. No. 7,705,559 B2, entitled "ASEPTIC BATTERY WITH A REMOVAL CELL CLUSTER, THE CELL CLUSTER CONFIGURED FOR CHARGING IN A SOCKET THAT RECEIVES A STERILIZABLE BATTERY" and PCT Pub. No. WO 2007/090025 A1, entitled "ASEPTIC BATTERY ASSEMBLY WITH REMOVABLE, RECHARGEABLE BATTERY PACK, THE BATTERY PACK ADAPTED TO BE USED WITH A CONVENTIONAL CHARGER", the disclosures of which are incorporated herein by reference.

Some wirelessly chargeable batteries 14 are also provided with supplemental components. These components may include internal sensors, data collection circuits, memories or control processors. These components may monitor the environment to which the battery is exposed, store data regarding the use of the battery, and/or store data regarding the medical device to which the battery is attached. The supplemental components may include or be similar to the supplemental components described in U.S. Pat. No. 6,018, 227 A, entitled "BATTERY CHARGER ESPECIALLY USEFUL WITH STERILIZABLE RECHARGEABLE BATTERY PACKS", and U.S. Pat. Pub. No. 2007/0090788 A1/PCT Pub. No. WO 2007/015639 A2, entitled "SYSTEM AND METHOD FOR RECHARGING A BATTERY EXPOSED TO A HARSH ENVIRONMENT", the disclosures of which are incorporated herein by reference. When a battery is provided with one or more of these supplemental components, the housing 108 may include a supplemental contact (e.g., data contact 124). This supplemental contact may be the contact through which signals are received from and/or transmitted to the supplemental components.

The battery head 114 may be provided with the power contacts 120, 122. The power contacts 120, 122 are conductive members through which the tool 116 draws an energizing current. In some instances, the power contact 120 is the cathode and the power contact 122 is the anode of the wirelessly chargeable battery 14. The power contacts 120, 122 may be shaped and physically adapted to enable the wirelessly chargeable battery 14 to removably couple to the tool 116. More specifically, the power contacts 120, 122 are physically adapted to be inserted into a corresponding portion of the tool 116 to establish physical and electrical connection with the tool 116. Thus, when the power contacts 120, 122 are inserted into the tool 116 and the power contacts 120, 122 are activated such that a voltage is applied across the power contacts 120, 122, the wirelessly chargeable battery 14 provides power to the tool 116.

The battery head 114 may also be provided with a data contact 124. In an instance wherein one or more data contacts 124 are included, data and instruction signals are written into and read out from the wirelessly chargeable battery 14 through data contact 124. The wirelessly chargeable battery 14 may thus use the data contact 124 to exchange data and instructions with a tool processor of the surgical tool 116. These signals may be exchanged using a suitable wired communication protocol. In other instances wherein the data contact 124 may be omitted, data and instructions may be written into and read out from the wirelessly chargeable battery 14 wirelessly.

The physical structure of the wirelessly chargeable battery 14 may vary from what is described and illustrated herein. For example, the battery head 114, power contacts 120, 122, and data contact 124 may be omitted from the top portion 110 and/or from the wirelessly chargeable battery 14. For instance, one or more of the power contacts 120, 122 may be mounted directly to the tool housing 118 as opposed to the wirelessly chargeable battery 14. In another instance, the power contacts 120, 122 may be mounted to cover 150. While the power contacts 120, 122 are illustrated in FIG. 8C as extending from battery head 114, the power contacts 120, 122 may be partially or completely housed within the cover 150 and/or housing 108 such that a corresponding contact from tool 116 inserts into the cover 150 and/or housing 108 to connect to the power contacts 120, 122.

As illustrated in FIG. 8C, the wirelessly chargeable battery 14 includes a plurality of components that will be further discussed herein. For example, as shown in FIG. 8C, the wirelessly chargeable battery 14 includes one or more cells 126, an induction coil 130, a battery microcontroller 140, a battery communication device 142, a gate 144, and a charging circuit 146. The wirelessly chargeable battery 14 may also include a tag 148 having a communication antenna, such as an NFC or RFID tag, that may be used to communicate with charging module 16. The battery components described herein may be included within a circuit board, such as circuit board 136 (shown in FIG. 8D).

Figure 8D:
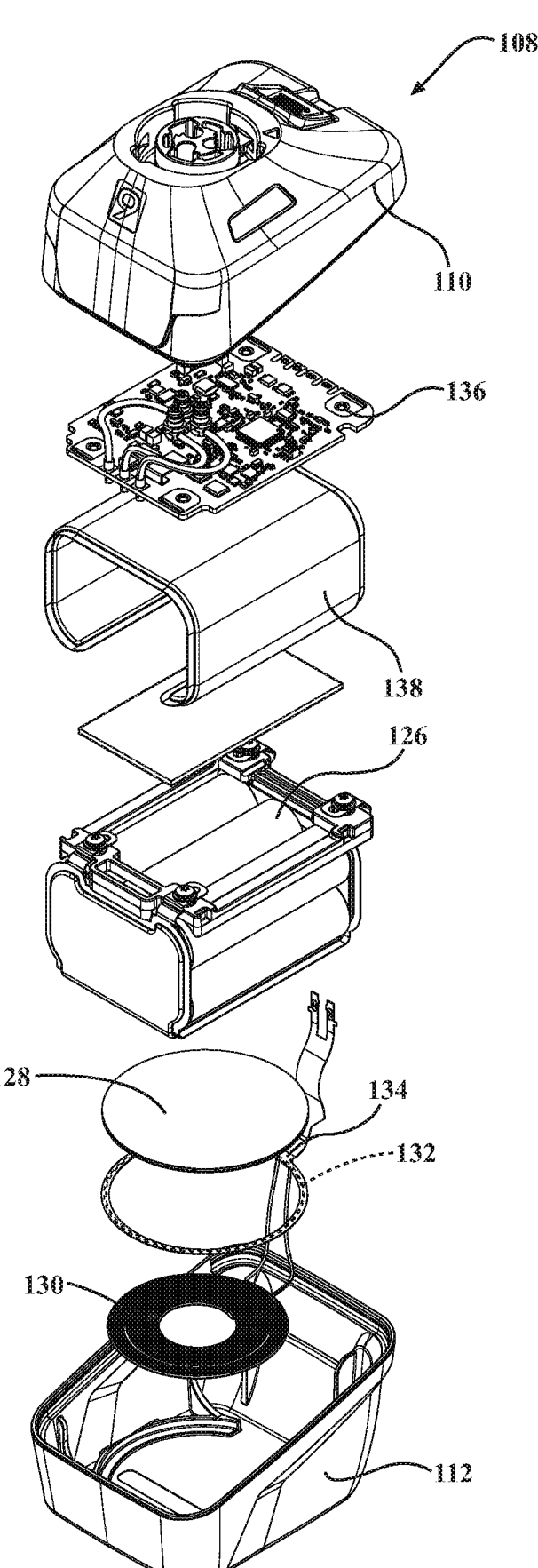
FIG. 8D is an exploded view of the wirelessly chargeable battery.
Figure 8E:
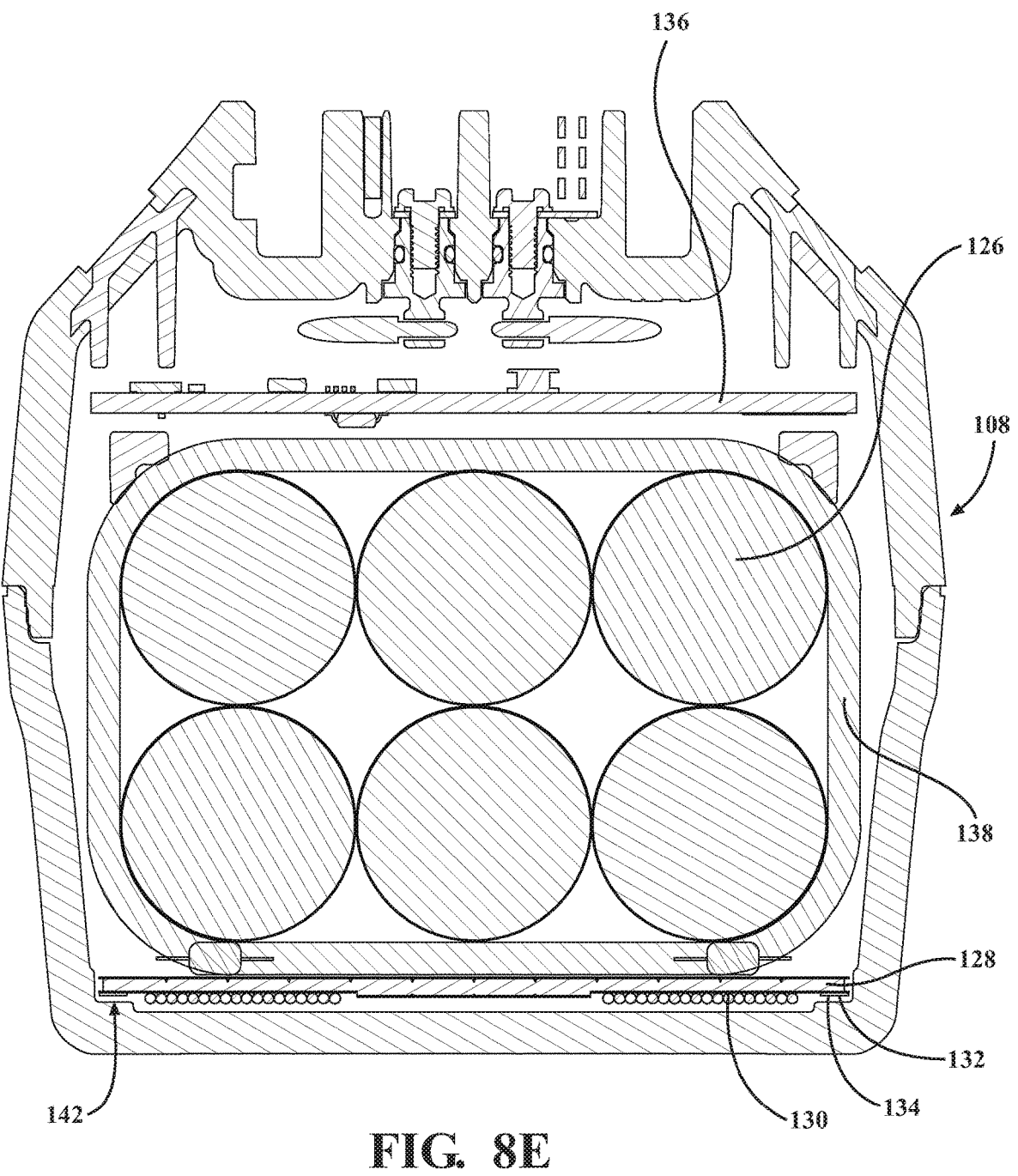
FIG. 8E is a section view of the wirelessly chargeable battery from FIG. 8A.

Referring to FIG. 8D, one or more cells 126 may be disposed within the housing 108. The cells 126 are used for storing charge within the wirelessly chargeable battery 14. As shown in FIGS. 8B and 7C, the wirelessly chargeable battery 14 includes six cells 126. However, in other instances, the wirelessly chargeable battery 14 may include a fewer or greater number of cells 110.

In some instances, the cells 126 are lithium ion cells. For example, the cells 126 may include any suitable nickel or lithium chemistry cell, including but not limited to, lithium ion ceramic cells, lithium iron phosphate, lithium iron phosphorous oxynitride cells, lithium ion nickel magnesium cobalt, or lithium tin phosphorous sulfide cells. In one instance, the cells 126 may be high-temperature cells configured to sustain functionality without damage or with reduced damage during sterilization (e.g., during an autoclave process). In another instance, the cells 126 may be lead acid, or any other suitable type of cell.

In some instances, each cell 126, when properly charged, has a nominal cell voltage of 3.3 VDC for lithium iron phosphate. Additionally, the cells 126 may be connected together in a series to form a cell cluster. In the illustrated instance, the wirelessly chargeable battery 14 includes six series connected cells 126. This instance of the wirelessly chargeable battery 14 is therefore configured to output a potential of around 19.8 VDC. Alternatively, in some instances, at least some of the cells 126 may be connected together in parallel. The number and type of cells 126 internal to the battery may of course be different from what is described.

As shown in FIG. 8D, a ferrite base 128 may be disposed between the housing 118 and the cells 126. Also shown, the induction coil 130 and a radiofrequency coil 132 may be disposed on the ferrite base 128 and attached with suitable techniques, such as with adhesive. The induction coil 130, the radiofrequency coil 132, and the ferrite base 128 are further shown in FIGS. 8D and 8E. In the instance shown in FIGS. 8D-8G, the ferrite base 128 is a monolithic component and the induction coil 130 and the radiofrequency coil 132 share the same ferrite base 128. For example, as shown, the induction coil 130 and the radiofrequency coil 132 are concentrically disposed on the ferrite base 128 such that the induction coil 130 is disposed within the radiofrequency coil 132. In other instances, the induction coil 130 and the radiofrequency coil 132 may be disposed differently on the ferrite base 128. For example, the induction coil 130 and the radiofrequency coil 132 may be disposed on the ferrite base 128 such that the induction coil 130 and the radiofrequency coil 132 are coplanar.

The ferrite base 128 may be used to reduce an amount of electromagnetic interference received from a powered wireless signal, such as an electromagnetic wave or a radiofrequency signal, and to increase a wireless range of the powered wireless signal. In the instance shown in FIGS. 8D-8G, the induction coil 130 is configured to receive electromagnetic waves for power transmission and the radiofrequency coil 132 is configured to receive radiofrequency signals for communication. The ferrite base 128 is used to prevent electromagnetic interference from the electromagnetic waves received by the induction coil 130 and from the radiofrequency signals transmitted/received by the radiofrequency coil 132.

In the instance shown in FIGS. 8D-8G, the induction coil 130 and the radiofrequency coil 132 are advantageously disposed on a single ferrite base 128, allowing the wirelessly chargeable battery 14 to be constructed in a more compact manner. In some instances, the induction coil 130 and the radiofrequency coil 132 may be disposed on separate ferrite bases. In such instances, the individual ferrite bases 128 may be chosen such that a wireless range of electromagnetic waves received by the induction coil 130 and a wireless range of radiofrequency signals transmitted/received by the radiofrequency coil 132 is maximized.

However, in the illustrated configuration, the induction coil 130 and the radiofrequency coil 132 are able to both be disposed on the same ferrite base 128 because the wireless range of electromagnetic waves received by the induction coil 130 is lesser than the wireless range of radiofrequency signals transmitted/received by the radiofrequency coil 132. As such, the ferrite base 128 may be chosen to maximize the wireless range of the electromagnetic waves received by the induction coil 130, while the wireless range of the radiofrequency signals transmitted/received by the radiofrequency coil 132 remains within an acceptable range.

The ferrite base 128 may be chosen based on their permeability and their Q factor. For example, ferrite bases with a higher permeability may increase a wireless range of signals transmitted and/or received by the ferrite base. Ferrite bases with a higher Q factor may more effectively reduce an amount of electromagnetic interference from a powered wireless signal transmitted and/or received from the ferrite base. For example, the ferrite base 128 may have a permeability of at least 700 and a Q factor of at least 20.

The induction coil 130 may include a material having a suitable temperature rating. As previously stated, temperatures inside an autoclave can exceed 120 degrees Celsius. As such, to ensure proper functionality of the induction coil 130, the induction coil may include a material having a temperature rating greater than 120 degrees Celsius. For example, the induction coil 130 may include Litz wire, which has a temperature rating of at least 155 degrees Celsius.

As shown in FIGS. 8D-8G, the radiofrequency coil 132 may be embedded in a medium of a flexible printed circuit board 134. As such, adjacent windings of the radiofrequency coil 132 are fixed relative to one another by the medium of the flexible printed circuit board 134. By fixing adjacent windings of the radiofrequency coil 132 relative to one another within the medium of the flexible printed circuit board 134, the radio frequency coil 132 is protected against degradation through use, i.e., temperature cycling and mechanical disruptions. In other words, setting the radiofrequency coil 132 within the medium of the flexible printed circuit board 134 provides a robust construction that minimizes a likelihood that windings of the radiofrequency coil 132 be displaced. In some instances, the medium of the flexible printed circuit board 134 includes a resin.

A frequency of radiofrequency signals transmitted and received by a radiofrequency coil may be defined by a number of windings of the radiofrequency coil and a space between windings of the radiofrequency coil. As such, by fixing the windings of the radiofrequency coil 132 relative to one another, the radiofrequency coil 132 is protected against slight movements of the windings, which may affect a frequency of radio frequency signals transmitted/received by the radio frequency coil 132. Such slight movements of the windings may occur through use of the wirelessly chargeable battery 14 if the windings of the radiofrequency coil 132 were not fixed relative to one another by the medium of the flexible printed circuit board 134.

The wirelessly chargeable battery 14 may also include a circuit board 136 disposed between the housing 108 and the cells. The circuit board 136 holds the below described components that selectively connect cells 126 to the power contacts 120, 122. For instance, the circuit board 136 includes, or is coupled to, a battery microcontroller 140 that controls the operation of the wirelessly chargeable battery 14 as described more fully herein.

The battery microcontroller 140 may be, or may include, any suitable controller, microcontroller, or microprocessor.

Figure 9:
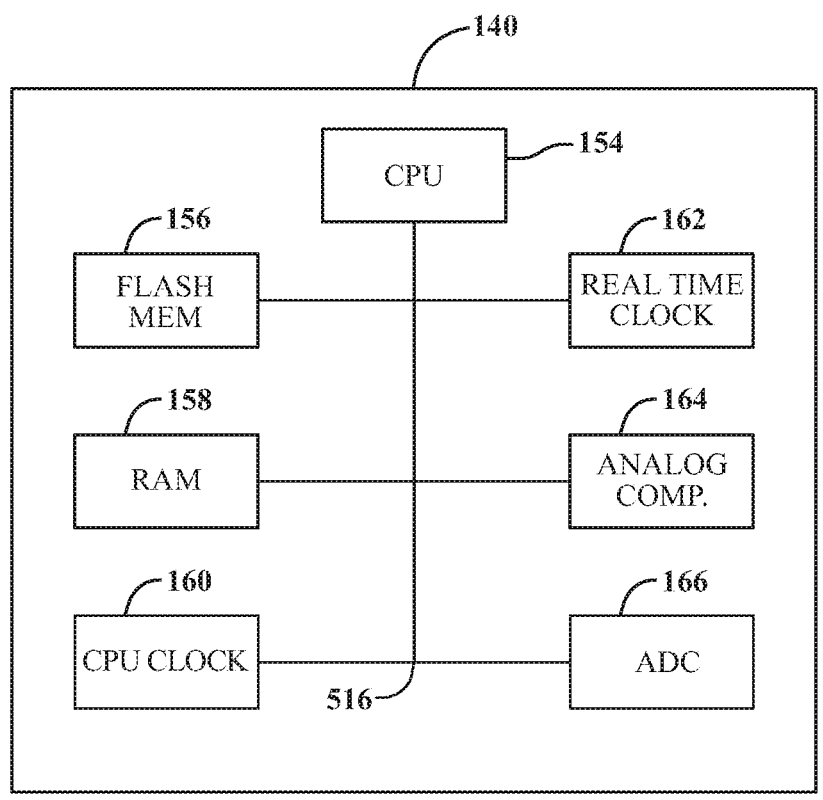
FIG. 9 is a block diagram of various sub-circuits internal to a battery controller of the wirelessly chargeable battery.

The battery microcontroller 140 includes a plurality of different sub-circuits which are described in FIG. 9. For example, in one instance, the battery microcontroller 140 may control when the wirelessly chargeable battery 14 is placed into a low power state and when the wirelessly chargeable battery 14 exits the low power state, as described herein.

As previously stated, the induction coil 130 is configured to receive charging power from charging module 16 via an electromagnetic charging signal. Additionally, as shown in FIG. 8C, the battery microcontroller 140 may be coupled to the induction coil 130 and to the charging circuit 146. The charging circuit 146 includes one or more circuit components that facilitate charging, or providing charge or current to, the cells 126. As such, the induction coil 130 is configured to receive the charging signal from the charging module 16 and is configured to convert the signal to a current that is transmitted to the charging circuit 146 for use in charging the cells 126. The charging circuit 146 may receive the current and may adjust the current and/or voltage to conform to a desired current or voltage of cells 126. When the cells 126 have been charged to a maximum or predefined state of charge, the battery microcontroller 140 may control the charging circuit 146 to prevent further current from being provided to cells 126.

Also shown in FIG. 8C, the wirelessly chargeable battery 14 may also include a gate 144, which includes one or more circuit components that selectably couple the cells 126 to the power contacts 120, 122. The gate 144 may include one or more transistors, such as field effect transistors, that are activatable by the battery microcontroller 140 to electrically couple the cells 126 to power contacts 120, 122 such that the cells 126 are selectively in communication with the power contacts 120, 122.

Figures 8F, 8G:
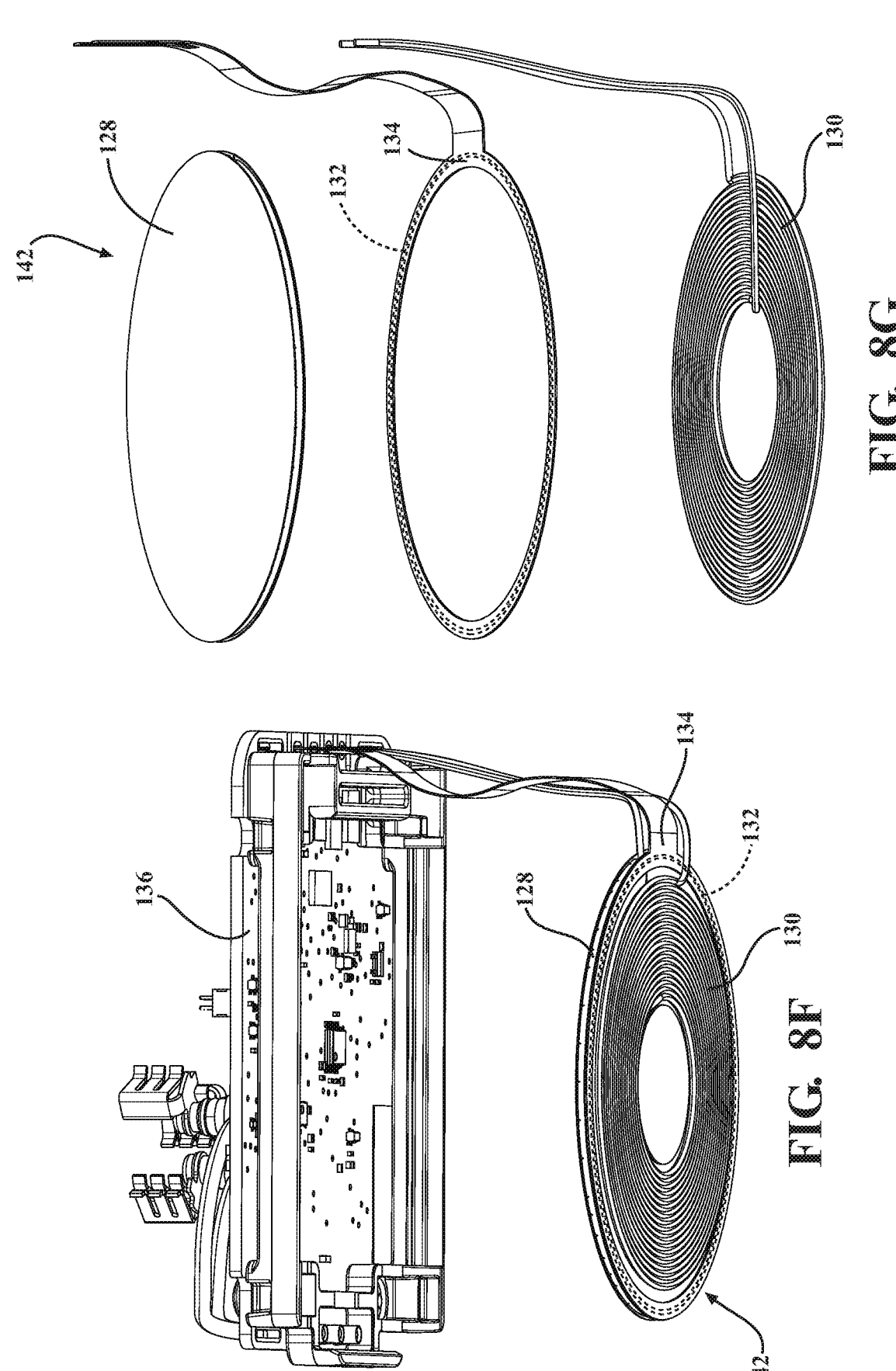
FIG. 8F is a view of a flexible printed circuit board, a ferrite base, an induction coil, and a radiofrequency coil of the wirelessly chargeable battery.
FIG. 8G is an exploded view of the ferrite base, the induction coil, and the radiofrequency coil of the wirelessly chargeable battery.

In the instance shown in FIG. 8D-8G, the battery communication device 142 includes the radiofrequency coil 132. Furthermore, as shown in FIG. 8F, the battery communication device 142 may be a coupled to the battery microcontroller 140, allowing the battery microcontroller 140 to communicate with the tool 116, the charging module 16, and/or a computing device, such as a tablet or server via radiofrequency signals of the radiofrequency coil 132. In other instances, the battery communication device 142 may be an infrared (IR) transceiver or a Bluetooth transceiver and may wirelessly transmit and receive data using any wireless protocol and/or technology, including but not limited to ZigBee, Bluetooth, Wi-Fi, etc.

When the wirelessly chargeable battery 14 is connected to the tool 116 or the charging module 16, the battery communication device 142 exchanges signals with a complementary transceiver within the tool 116 (or within another suitable medical device) or within the charging module 16. For example, the battery communication device 142 may transmit authentication data to a medical device communication module (not shown) and/or may receive authentication data from the medical device communication module to authenticate the tool 116 and/or the wirelessly chargeable battery 14. In a similar manner, the battery communication device 142 may transmit authentication data to the charging module 16 to enable the charging module 16 to authenticate wirelessly chargeable battery 14. Accordingly, the wirelessly chargeable battery 14, the charging module 16, and/or the tool 116 may ensure that only authorized and/or compatible components are being used with each other.

Alternatively, in some instances, the battery communication device 142 may be a wired transceiver that transmits data to and from tool 116 and/or a computing device using a suitable wired protocol. In such instances, a user may send and/or receive data from the wirelessly chargeable battery 14, the charging module 16, and/or the tool 116 using battery communication device 142.

The battery communication device 142 may also include the tag 148, shown in FIG. 8C. Alternatively, the battery communication device 142 and the tag 148 may be separate devices. In some instances, the tag 148 may include an integrated antenna (not shown) for use in communicating with the charging module 16. Alternatively, the tag 148 may be coupled to the battery communication device 142 or may be a standalone component with an integrated antenna. In some instances, battery data, such as a state of health, a state of charge, and/or battery operational data of the wirelessly chargeable battery 14, may be stored in the tag 148 and may be transmitted to the charging module 16 via NFC, RFID, or any other suitable communication protocol. In some instances, tag 148 is a passive tag that is inductively powered via an electromagnetic field, such as a field generated by the charging module 16.

The wirelessly chargeable battery 14 may also include a thermally insulative material 138. As shown in FIGS. 8D and 7E, the thermally insulative material 138 may be at least partially disposed between the cells 126 and the ferrite base 128. The thermally insulative material 138 may also be at least partially disposed between the cells 126 and the housing 108. The thermally insulative material 138 is configured to insulate the cells 126 from the high temperatures. As such, in instances where the cells 126 may suffer degradation when exposed to high temperatures of an autoclave, the thermally insulative material 138 minimizes damage incurred during sterilization or autoclave cycles. By placing the thermally insulative material 138 between the cells 126 and the induction coil 130, the induction coil 130 can be positioned as close to a bottom of the housing 108 of the wirelessly chargeable batter 14 as possible. This ensures optimal charging characteristics, while maintaining protection of the cells 126 from high temperature environments.

In some instances, the thermally insulative material 138 may include an aerogel, such as polyimide, silica, or carbon aerogel. For example, the thermally insulative material 138 may be an aerogel with a thermal conductivity of approximately 32.5 mW/(m*K) at 298 Kelvin. The thermally insulative material 138 may also be compressed without affecting its thermal conductivity. This is because compressing the thermally insulative material 138 does not reduce an amount of insulative material (e.g. an aerogel, such as polyimide, silica, or carbon aerogel) included in the thermally insulative material 138. In one instance, the thermally insulative material 138 may be compressed approximately 50% when disposed within the housing 108.

FIG. 9 is a block diagram illustrating various subcircuits or components of the battery microcontroller 140. While the following subcircuits or components are illustrated in FIG. 5 as being included within the battery microcontroller 140, it should be recognized that one or more of the subcircuits or components may be included within any suitable device, module, or portion of the wirelessly chargeable battery 14.

In some instances, a central processing unit (CPU) 154 controls the operation of the battery microcontroller 140 and the components connected to the battery controller. A non-volatile flash memory 156 stores instructions executed by the CPU 154. As described more fully herein, flash memory 156 also stores the instructions used to regulate the charging of the wirelessly chargeable battery 14, data describing the use history of the wirelessly chargeable battery 14, and data describing the use history of the tool 116 to which the wirelessly chargeable battery 14 is attached.

A random access memory 158 functions as a temporary buffer for data read and generated by battery microcontroller 140. A CPU clock 160 supplies the clock signal used to regulate the operation of the CPU 154. While shown as single block for purposes of simplicity, it should be appreciated that the CPU clock 160 includes an on-chip oscillator as well as sub-circuits that convert the output signal from the oscillator into a CPU clock signal. A real time clock 162 generates a clock signal at fixed intervals.

An analog comparator 164 and an analog to digital converter (ADC) 166 are used to process output signals of one or more sensors or other components of the wirelessly chargeable battery 14, such as a temperature sensor (not shown). In FIG. 5, the above sub-circuits are shown interconnected by a single bus 516. It should be appreciated that this is for simplicity. In practice, dedicated lines may connect certain of the sub circuits together. Likewise, it should be understood that the battery microcontroller 140 may have other sub-circuits. These sub-circuits are not specifically relevant to this disclosure and so are not described in detail.

Figure 10:
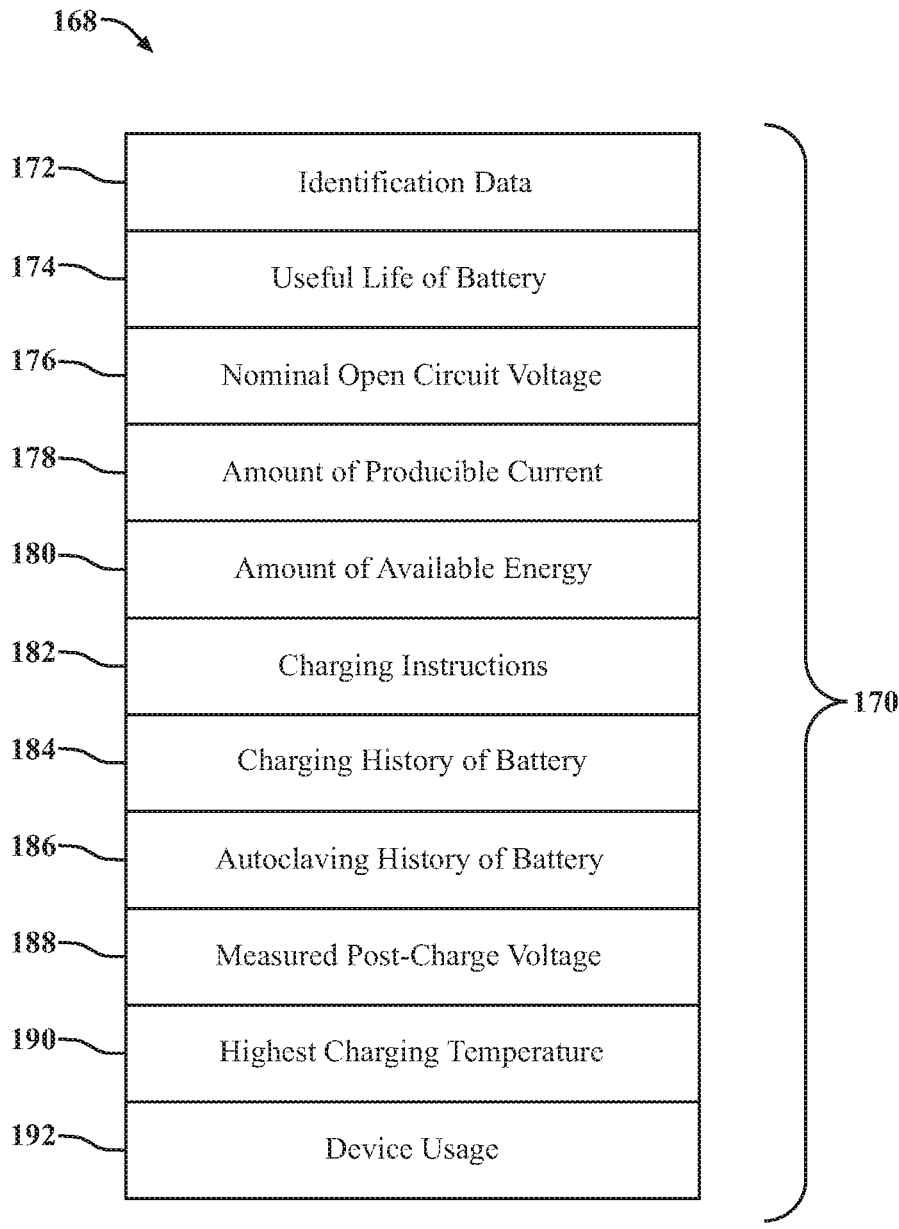
FIG. 10 is a block diagram of an exemplary data structure that may be stored in a memory of the battery controller.

FIG. 10 is a block diagram of a data structure 168 that may be stored in flash memory 156 (shown in FIG. 5), in addition to the instructions executed by the battery microcontroller 140. The data structure 168 may store data, such as battery operational data, as one or more fields 170 in one or more records or files. As one example, identification data 172 may be stored in the file and may be used to identify the wirelessly chargeable battery 14. The identification data 172, may include, for example, a serial number, a lot number, a manufacturer identification, and/or an authorization code. The authorization code or other identification information may be read by the tool 116 or charging module 16 to which the wirelessly chargeable battery 14 is connected to authenticate the wirelessly chargeable battery 14 (e.g., to determine if, respectively, the wirelessly chargeable battery 14 can power the tool 116 or be recharged by the charging module 16). The flash memory 156 may also include a field indicating the useful life 174 of the wirelessly chargeable battery 14 (sometimes referred to as "useful life data"). Useful life data 174 may include one or more of the following data types: battery expiration data, a number of charging cycles that the wirelessly chargeable battery 14 has undergone, and a number of autoclaving procedures or cycles the wirelessly chargeable battery 14 has been subjected to. Other fields may indicate the nominal open circuit voltage 176 of the signal produced by the wirelessly chargeable battery 14, the current 178 the wirelessly chargeable battery 14 can produce, and the amount of available energy 180 (represented in joules, for example).

Charging instructions 182 for the wirelessly chargeable battery 14 may be stored in a field 170. This data can include the types of data described in the memories of the batteries disclosed in U.S. Pat. Nos. 6,018,227 A and 6,184,655 B1, the disclosures of which are hereby incorporated by reference.

Flash memory 156 also contains data describing a charging history 184 and autoclave history 186 of the wirelessly chargeable battery 14. For example, as part of the charging history 184 of the wirelessly chargeable battery 14, data may be stored indicating the number of times the wirelessly chargeable battery 14 was charged, as well as a timestamp indicating the time each charging cycle was initiated and/or ended.

As part of the autoclaving history 186 of the wirelessly chargeable battery 14, flash memory 156 may store data indicating the total number of times the wirelessly chargeable battery 14 has been autoclaved, and/or a cumulative amount of time the wirelessly chargeable battery 14 has been subjected to temperatures at or above a threshold considered to be the autoclave temperature. In one non-limiting instance, the threshold temperature is about 130 degrees Celsius. In a more specific instance, the threshold temperature is about 134 degrees Celsius. However, it should be recognized that the threshold temperature may be any suitable temperature. The autoclaving history 186 field 170 may also include data indicating the number of times and/or the cumulative amount of time the wirelessly chargeable battery 14 has been exposed to potentially excessive autoclaving cycles. The autoclaving history 186 may also include peak autoclave temperature data indicating the highest autoclave temperature to which the wirelessly chargeable battery 14 has been exposed and an amount of time the wirelessly chargeable battery 14 has been in an autoclave for each of its autoclaving cycles, as well as a period of the longest single time the wirelessly chargeable battery 14 was subjected to autoclaving.

A measured post-charge voltages field 188 contains data indicating the measured voltages-at-load of the wirelessly chargeable battery 14 after each charging. In some instances, field 188 only contains these measurements for the last 1 to 10 charging cycles. In another field 190, data is stored indicating the highest battery temperature measured during its previous charging cycles. Again, field 190 may only contain data indicating the highest temperatures measured during the last 1 to 10 charging cycles of the battery.

The flash memory 156 also contains a device usage field 192. As discussed below, the device usage field 192 stores data obtained from the tool 116 or other medical device that the wirelessly chargeable battery 14 is employed to power. For example, in one instance, the device usage field 192 may store data indicating a number of times that the wirelessly chargeable battery 14 has been connected to tool 116, a number of trigger pulls of tool 116, a total amount of time that the wirelessly chargeable battery 14 has provided power to tool 116 during an operation of tool 116 (i.e., a runtime of tool 116), a number of power cycles that tool 116 has undergone, a maximum temperature tool 116 has been exposed to, a current consumption of tool 116, a speed histogram of tool 116, a list of serial numbers or other identifiers of the devices that the wirelessly chargeable battery 14 has interacted with, and/or any other suitable data of tool 116. It should be understood, however, that the device usage field 192 does not include patient data. The data stored in the device usage field 192 may be transmitted by a communication module of medical device 150 and received by battery communication device 142.

Figure 11A:
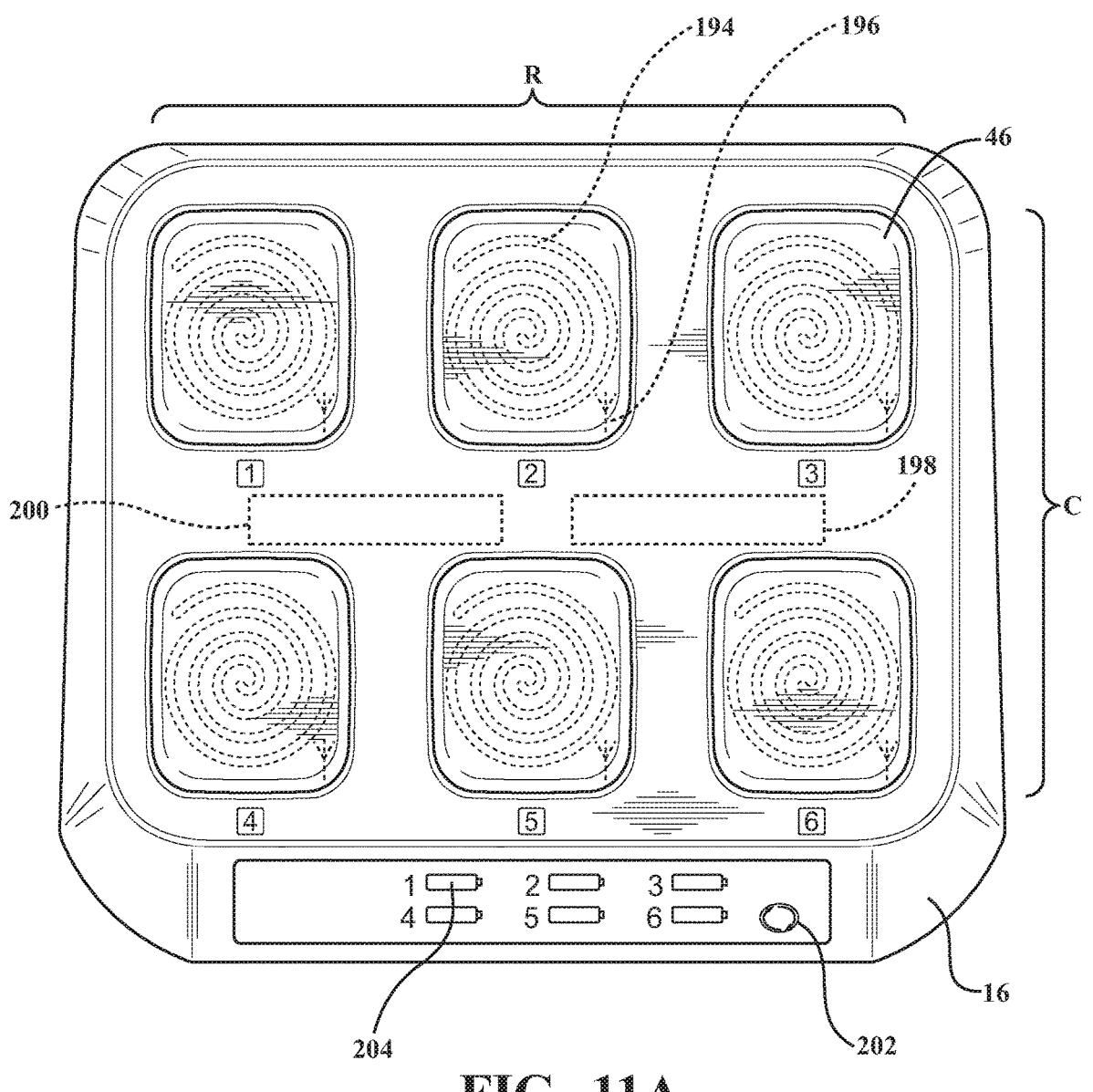
FIG. 11A is a top view of the charging module.
Figure 11B:
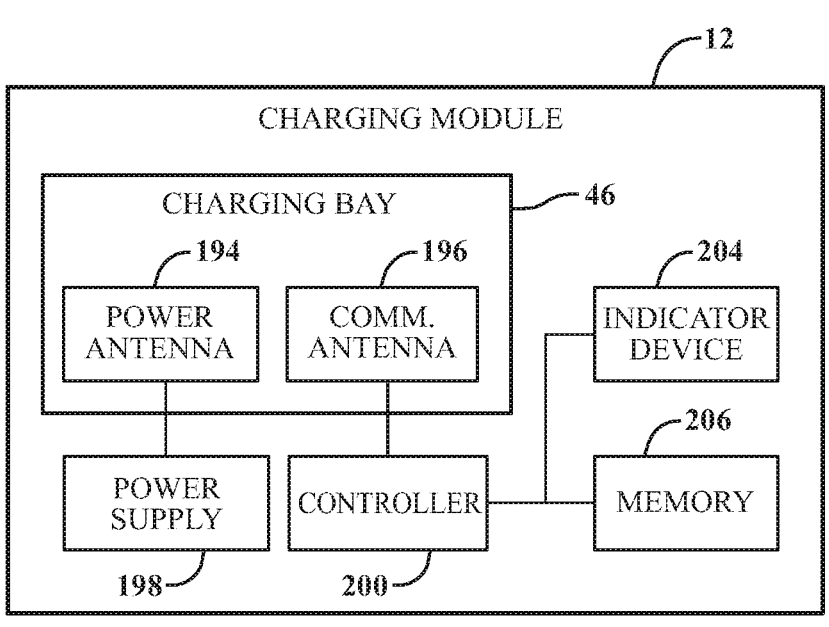
FIGS. 11B and 11C are block diagram views of two instances of the charging module.
Figure 11C:
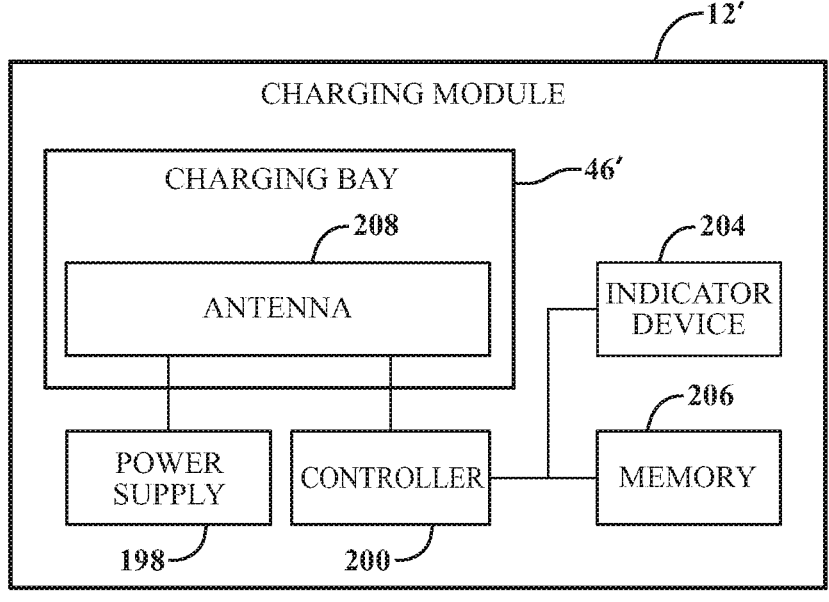

FIGS. 11A-11C further illustrate the charging module 16. As shown, the charging module 16 includes a plurality of charging bays 46 configured to receive the plurality of protrusions 44. An autoclavable container 12 may be placed onto the charging module 16 such that each protrusion 44 of the autoclavable container 12 is placed on a charging bay 46 of charging module 16.

In various instances, the charging module 16 may include any suitable number of charging bays 46. For example, in FIG. 11A, the charging module 16 includes six charging bays 18. In other instances, the charging module 16 may include any number of charging bays 46 greater than one (e.g. the charging module 16 may include two, three, four, eight, etc. charging bays 46) and a structure of the charging module 16 may vary accordingly. In some instances, a number of charging bays 46 in a row R and a number of charging bays 46 in a column C may be different from one another such that the charging module 16 may accommodate autoclavable containers 12 that include different numbers of protrusions 44. For example, the charging module 16 in FIG. 11A includes a row R with three charging bays 46 and a column C with two charging bays 46. As such, an autoclavable container 12 with three protrusions 44 and an autoclavable container 12 with two protrusions 44 may be placed on the charging module 12.

The charging module 16 may receive one autoclavable container 12 or a plurality of autoclavable containers 12. Referring to FIG. 1, three autoclavable containers 12 are placed along the three columns C of the charging module 16. In other instances, a fewer number of autoclavable containers 12 may be placed onto the charging module 16. Additionally, the autoclavable containers 12 may be placed along the rows R. Furthermore, when an autoclavable container 12 is placed on a row R or a column C of the charging module 16, the protrusions 44 of the autoclavable container 12 need not be disposed within all charging bays 16 of the row R or the column C. For instance, the autoclavable containers 12 include two protrusions 44 and may be placed along a row R such that the two protrusions 44 are disposed within two of the three charging bays 46 of the row R.

The charging bays 46 may be arranged in any suitable fashion. For example, in FIG. 11A, the six charging bays 46 are arranged in two rows R with each row R including three charging bays 46. The six charging bays 46 of FIG. 11A may also be described as being arranged into three columns C with each column C including two charging bays 46. Alternatively, in other arrangements, the charging module 16 may include a single charging bay 48 for receiving a protrusion 44 of an autoclavable container 12. In another instance, the charging bays 48 may be arranged in a single row R or column C.

In various instances, the charging module 16 may be shaped in any suitable manner for charging wirelessly chargeable batteries 14. For example, referring to FIG. 11A, the charging bays 46 of the charging module 16 are illustrated as substantially flat surfaces configured to receive the protrusions 44 of the autoclavable container 12. In other instances, the charging bays 46 may be substantially flat surfaces similar to a charging surface of a Wireless Power Consortium (Qi) charger. In some instances, the charging bays 46 may include a frictional surface to prevent wirelessly chargeable batteries 14 from sliding.

As shown in FIG. 11A, each charging bay 48 may include a power antenna 194 and a communication antenna 196. The power antenna 194 is illustrated as a phantom coil in each charging bay 46. The power antenna 194 of a charging bay 48 is configured to provide charging power to a wirelessly chargeable battery 14 disposed within a receptacle 42 of an autoclavable container 12 when the wirelessly chargeable battery 14 is within a proximity of the charging bay 14 such that the induction coil 130 of wirelessly chargeable battery 14 is within a proximity of the power antenna 194. The communication antenna 196 is illustrated as a phantom antenna in each charging bay 46. The communication antenna 196 of a charging bay 48 is configured to establish communication with the battery microcontroller 140 of a wirelessly chargeable battery 16 disposed within a receptacle 42 of an autoclavable container 12 in response to the wirelessly chargeable battery 16 being within a proximity of the charging bay 48.

For example, each receptacle 42 and protrusion 44 of an autoclavable container 12 is shaped to align with a corresponding charging bay 46 of a charging module 16. As such, by placing a wirelessly chargeable battery 16 in a receptacle 42 and the autoclavable container 12 on the charging module 16, the wirelessly chargeable battery 14 is within a proximity of the power antenna 194 and the communication antenna 196 such that the power antenna 194 provides charging power to the wirelessly chargeable battery 16 and the communication antenna 196 communicates with the battery microcontroller 140 of the wirelessly chargeable battery 16.

Also shown in FIG. 11A, the charging module 16 may include a power source, illustrated by phantom rectangular block 198. Also internal to the charging module 16 is a charger controller, illustrated by phantom rectangular block 200. When the wirelessly chargeable battery 14 is placed on the charging module 16, the power supply 198 applies a charging current to the battery cells 126. Charger controller 200 regulates the charging of the wirelessly chargeable battery 14 by the power supply 198. The charger controller 200 is also capable of retrieving data from and writing data to a memory internal to the wirelessly chargeable battery 14.

Furthermore, referring to FIG. 11B, the power antenna 194 and the communication antenna 196 are coupled to the charger controller 200. As such, when the autoclavable container 12 is positioned proximate to a charging module 16 such that each wirelessly chargeable battery 14 within an associated receptacle 42 of the autoclavable container 12 is positioned proximate to a charging bay 46, the wirelessly chargeable battery 14 may communicate with the charger controller 200 via a communication antenna 196 of a charging bay 46 and may receive charging power via power antenna 194 of the charging bay 46.

The charging module 16 may include a display area 202 that includes a plurality of indicators that provide information relating to the status of the wirelessly chargeable batteries 14 being charged by the charging module 16. In one instance, a charging display 202 is associated with each charging bay 46 of the charging module 16. The charging display 202 may include an indicator representing a state of charge of the wirelessly chargeable battery 14 being charged by the charging bay 46. The charging display 202 may also include an indicator representing a state of health of the wirelessly chargeable battery 14 (not shown) being charged by the charging bay 46. In one instance, the state of health of each wirelessly chargeable battery 14 may be determined in a manner similar to that described in U.S. Patent Publication No. US 2018/0372806 A1, entitled "SYSTEM AND METHOD FOR DETERMINING AN AMOUNT OF DEGRADATION OF A MEDICAL DEVICE BATTERY", the disclosure of which is incorporated herein in its entirety. Each indicator may be implemented using one or more indicator devices 204. Accordingly, each indicator 204 may include an LED or other light source that illuminates all or a portion of the indicator 204 to display the state of health and/or the state of charge to a user. Alternatively, each indicator 204 may include any other suitable device or display that enables a user to view the data representing the state of health and/or the state of charge of each wirelessly chargeable battery 14. Additionally or alternatively, one or more of the indicators 204 may be provided on or within each wirelessly chargeable battery 14.

As described more fully herein, data representative of the state of health and the state of charge of each wirelessly chargeable battery 14 may be transmitted by each wirelessly chargeable battery 14 to the charging module 16 through a communication antenna 196 of a charging bay 46 that the wirelessly chargeable battery 14 is proximate to. The data is transmitted from the communication antenna 196 to the charger controller 200. The charger controller 200 controls the display area 202 to cause a state of charge indicator and/or a state of health indicator to reflect the state of charge data and the state of health data received from wirelessly chargeable battery 14.

In some instances, the display area 202 may also include a temperature indicator (not shown) that displays data representative of an ambient temperature of an environment in which charging module 16 is positioned. The charger controller 200 may receive one or more signals from a temperature sensor indicative of the sensed ambient temperature. The charger controller 200 may control the temperature indicator to display the sensed temperature in the form of a digital display or any other suitable display.

In another instance, the display area 202 may include a refresh icon (not shown) that a user may select or press. The charger controller 200 may receive a signal in response to the user selecting or pressing the refresh icon, and the charger controller 200 may initiate a refresh of the display area 202 in response. The refresh of the display area 202 may include a re-determination and re-display of the state of charge of each wirelessly chargeable battery 14, the state of health of each wirelessly chargeable battery 14, and the ambient temperature of the environment in which the charging module 16 is placed.

In one instance, the charging module 16 and/or the autoclavable container 12 may include one or more sensors that measure a sterility of each wirelessly chargeable battery 14 and/or the sterile volume 30 (shown in FIG. 2B). The sensors may transmit signals representative of the measured sterility to the charger controller 200, and the charger controller 200 may cause an associated indicator (not shown) within the display area 202 to display the measured sterility.

Additionally or alternatively, the charger controller 200 may cause an indicator (not shown) within the display area 202 to display a sterility state of each wirelessly chargeable battery 14 and/or the volume 30. For example, when wirelessly chargeable batteries 14 are placed within the autoclavable container 12 and the autoclavable container 12 is sterilized, a temperature sensor within the autoclavable container 12 may detect the exposure of the autoclavable container 12 to a temperature indicative of an autoclave process (e.g., a temperature of more than 120 degrees Celsius) or other sterilization process and may cause a pin or portion of data stored in a memory (not shown) to reflect that the volume 30 and the wirelessly chargeable batteries 14 disposed therein are in a sterile state. Another sensor may detect when the autoclavable container 12 is opened (e.g., when the top portion is removed) and may cause the pin or portion of data stored in memory to reflect that the volume 30 and the wirelessly chargeable batteries 14 disposed therein may no longer be in a sterile state. The charger controller 200 may receive a signal representative of the sterile state of the autoclavable container 12 and may cause the indicator within display area 202 to reflect the sterile state.

FIG. 11B is a block diagram of the charging module 16. In the instance shown in FIG. 11A, the charging module 16 is a wireless charging module that provides a wireless charging signal to wirelessly chargeable battery 14 to wirelessly charge wirelessly chargeable battery 14. FIG. 11C is a block diagram of charging module 16', which is an instance of charging module 16. The charging module 16' is also a wireless charging module that provides a wireless charging signal to wirelessly chargeable battery 14 to wirelessly charge wirelessly chargeable battery 14.

As illustrated in FIG. 11B, the charging module 16 includes a power supply 198, a charger controller 200, a memory 206, and one or more indicator devices 204. The charging module 16 also includes a charging bay 46, which includes a charger power antenna 194 and a charger communication antenna 196. In one instance, the charging module 16 is a charging device such as the charging module 16 shown in FIG. 11A. In other instances, charging module 16 may be a wireless mat, tray, inspection station, or other charging surface that the autoclavable container 12 may be placed upon to wirelessly charge the wirelessly chargeable battery 14. Alternatively, the charging module 16 may be embedded in tool 116 or another suitable device.

As illustrated in FIG. 11C, the charging module 16' includes the power supply 198, the charger controller 200, the memory 206, and the one or more indicator devices 204. However, charging module 16' also includes a charging bay 46', which is an instance of the charging bay 46. The charging bay 46' includes one antenna 208, which is configured to perform the tasks of the power antenna 194 and the charger communication antenna 196. As such, the antenna 208 may be configured to perform any task that the power antenna 194 and the charger communication antenna 196 are described as performing herein. In some instances, the charging module 16' may be a Wireless Power Consortium (Qi) charger.

The power supply 198 converts line current into signals that can be used to energize other components of the charging module 16. In FIG. 11B, the power supply 198 also produces a signal that is applied to the charger power antenna 194 to enable the antenna 194 to provide wireless charging power to the wirelessly chargeable battery 14. In FIG. 11C, the power supply 198 similarly produces a signal that is applied to the antenna 208 to enable the antenna 208 to provide wireless charging power to the wirelessly chargeable battery 14.

The charger power antenna 194 of FIG. 11B receives a signal from the power supply 198 and converts the signal to a wireless charging signal that is wirelessly transmitted to the wirelessly chargeable battery 14. The wireless charging signal is a radio frequency (RF) signal that is receivable by an induction coil 130 of the wirelessly chargeable battery 14. Accordingly, the charger power antenna 194 acts as a transmission component that transmits the charging signal to the wirelessly chargeable battery 14. Similarly, the antenna 208 of FIG. 11C may be configured to receive a signal from power supply 198, convert the signal to a wireless charging signal that is wirelessly transmitted to the wirelessly chargeable battery 14, and transmit the charging signal to the wirelessly chargeable battery 14.

In one instance, the charger controller 200 may operate a switching device (not shown), such as a transistor, switch, or other device, to selectively enable and disable the power antenna 194. Accordingly, in an instance in which the communication antenna 196 is activated, the charger controller 200 may control the switching device to deactivate the power antenna 194, such as by preventing current from entering the power antenna 194. Similarly, the charger controller 200 may selectively enable and disable an ability of the antenna 208 to receive the signal from the power supply 198, convert the signal to a wireless charging signal that is wirelessly transmitted to the wirelessly chargeable battery 14, and/or transmit the charging signal to the wirelessly chargeable battery 14.

The charger controller 200 may include a processor that regulates the power supply 198 to provide the signal having a suitable current, voltage, and frequency to the charger power antenna 194. The charger controller 200 controls the provision of the charging signal to wirelessly charge the wirelessly chargeable battery 14 in response to the wirelessly chargeable battery 14 requesting additional charge (referred to herein as a charging request), for example. When the charger controller 200 receives a charging request from the wirelessly chargeable battery 14, the charger controller 200 may determine if the wirelessly chargeable battery 14 has a sufficient level of health to be charged. In one instance, the charger controller 200 compares battery state of health data received from the wirelessly chargeable battery 14 with a predetermined threshold. If the battery state of health data meets or exceeds the predetermined threshold, the charger controller 200 approves the charging request and commands the power supply 198 to provide the charging signal to the wirelessly chargeable battery 14 via the charger power antenna 194 or the antenna 208.

The memory 206 is a computer-readable memory device or unit coupled to charger controller 200. In one instance, the memory 206 is a non-volatile random-access memory (NOVRAM), such as flash memory. The memory 206 includes charging sequence and charging parameter data that, when executed by the charger controller 200, regulates the wireless charging of the wirelessly chargeable battery 14. In one instance, the memory 206 also stores data indicating a state of health and/or state of charge of the wirelessly chargeable battery 14. For example, in one instance, the wirelessly chargeable battery 14 transmits data representative of the state of health and/or state of charge of the wirelessly chargeable battery 14 to the charger communication antenna 196. The charger communication antenna 196 transmits the state of health and state of charge data to the charger controller 200, which then stores the data in the memory 206. In an instance where the memory 206 is a flash memory, such as the flash memory 156 (further described herein), the charger communication antenna 196 may receive the data representative of the state of health and/or the state of charge of the wirelessly chargeable battery 14 when the wirelessly chargeable battery 14 is unpowered and/or without communicating with the battery microcontroller 140.

The charger communication antenna 196 may be configured to communicate bi-directionally with the battery communication device 142. In one instance, the charger communication antenna 196 receives battery state of health and/or state of charge data from the memory 206 and provides the data to the charger controller 200. In addition, the charger communication antenna 196 may receive a charging request from the wirelessly chargeable battery 14 and may transmit the charging request to the charger controller 200. Similarly, the antenna 208 of FIG. 11C may be configured to communicate bi-directionally with the battery communication device 142, receive battery state of health and/or state of charge data from the memory 206, provide the data to the charger controller 200, receive a charging request from the wirelessly chargeable battery 14, and transmit the charging request to the charger controller 200.

In one instance, the charger controller 200 may operate a switching device (not shown), such as a transistor, switch, or other device, to selectively enable and disable communication antenna 196. Accordingly, in an instance in which the power antenna 194 is activated, the charger controller 200 may control the switching device to deactivate the communication antenna 196, such as by preventing current from entering the communication antenna 196. Similarly, the charger controller 200 may selectively enable and disable an ability of the antenna 208 to communicate bi-directionally with the battery communication device 142, receive battery state of health and/or state of charge data from memory 206, provide the data to the charger controller 200, receive a charging request from the wirelessly chargeable battery 14, and transmit the charging request to the charger controller 200.

The indicator devices 204 indicate a status of the charging module 16 and/or the wirelessly chargeable battery 14. The indicator device 204 may include at least one of a display, a speaker, and a light source, such as a light-emitting diode (LED). The display may be an LCD, LED, or other type of display. In some instances, multiple indicators may be used to indicate the status of the charging module 16, 16' and/or the wirelessly chargeable battery 14. As illustrated in FIG. 11A, the indicator device 204 may be one or more LEDs. In one instance, the charger controller 200 may activate the one or more indicator devices 204 based on the battery state of health and/or state of charge data received from wirelessly chargeable battery 14. For example, the charger controller 200 may cause an LED to emit a green color (or another suitable color) if the battery state of health data meets or exceeds the predetermined threshold. The charger controller 200 may cause an LED to emit a red color (or another suitable color) if the battery state of health data is less than the predetermined threshold. The indicator devices 204 thus can indicate to a user the overall health status of the wirelessly chargeable battery 14. The indicator devices 204 may additionally or alternatively be used to indicate a state of charge of the wirelessly chargeable battery 14. For example, the indicator devices 204 may include one or more LEDs or other light sources that emit a first color of light when the wirelessly chargeable battery 14 is not fully charged and may emit a second color of light when the wirelessly chargeable battery 14 is fully charged. It is further contemplated that the wirelessly chargeable battery 14 may include one or more indicator devices 204 that indicate the battery state to a user, and as such, the wirelessly chargeable battery 14 itself may include a light source, display, or speaker.

In one instance, the charging module 16 may include a plurality of charging bays 46 that each includes a separate power antenna 194 and communication antenna 196. Similarly, charging module 16' may include a plurality of charging bays 46' that each include an antenna 208. Accordingly, each charging bay 46 and 46' may be shaped and sized to receive a separate wirelessly chargeable battery 14 as described more fully herein. For example, the charging modules 12, 12' may include two charging bays 46, 46', respectively, of a similar shape, or two or more charging bays 46, 46', respectively, of different shapes to accommodate batteries having different shapes and/or sizes. Each charging bay 46 may therefore communicate with a respective wirelessly chargeable battery 14 that is placed proximate to the charging bay 46 via the communication antenna 196 and may provide charging power to the wirelessly chargeable battery 14 via the power antenna 194. Similarly, each charging bay 46' may communicate with a respective wirelessly chargeable battery 14 that is placed proximate to a charging bay 46' via the antenna 208, and may provide charging power to the wirelessly chargeable battery 14 via the antenna 208. Each charging bay 46 and 46' may be configured as a recessed volume within the surface of the charger. Alternatively still, the charger modules 12, 12' may include a plurality of charging bays 46, 46', respectively, each being shaped and sized identically.

In one instance, each power antenna 194 of each charging bay 46 may only provide charging power when a wirelessly chargeable battery 14 is placed proximate to a charging bay 46. Accordingly, when a wirelessly chargeable battery 14 is not placed proximate to a charging bay 46 (i.e., if charger controller 200 does not detect the proximity of wirelessly chargeable battery 14 with respect to charging bay 46), charger controller 200 may deactivate or otherwise disable the power antenna 194 of that charging bay 46 to conserve power.

Figure 12:
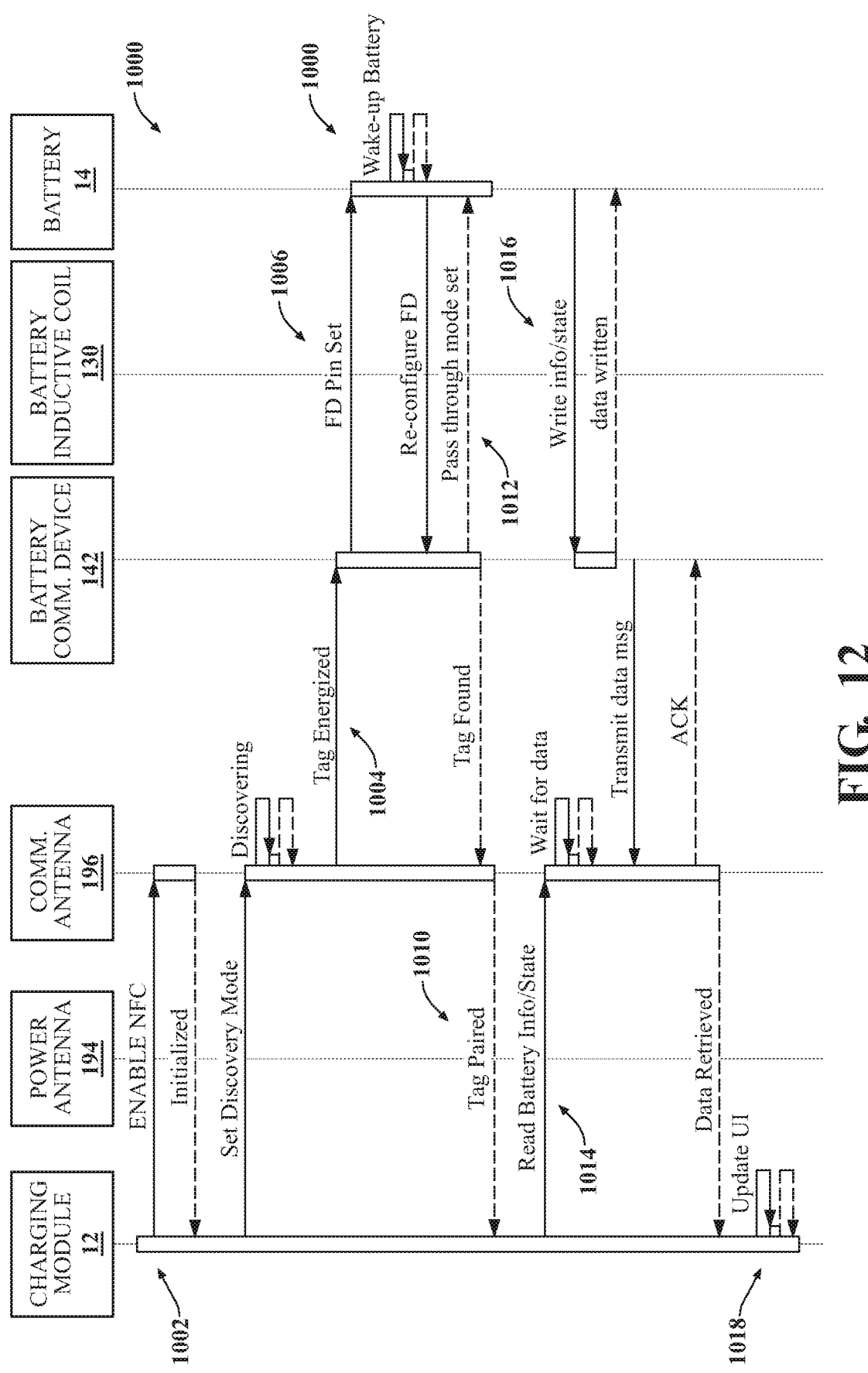
FIGS. 12-14 are flowcharts of an exemplary method of providing charge to a wirelessly chargeable battery.
Figure 13:
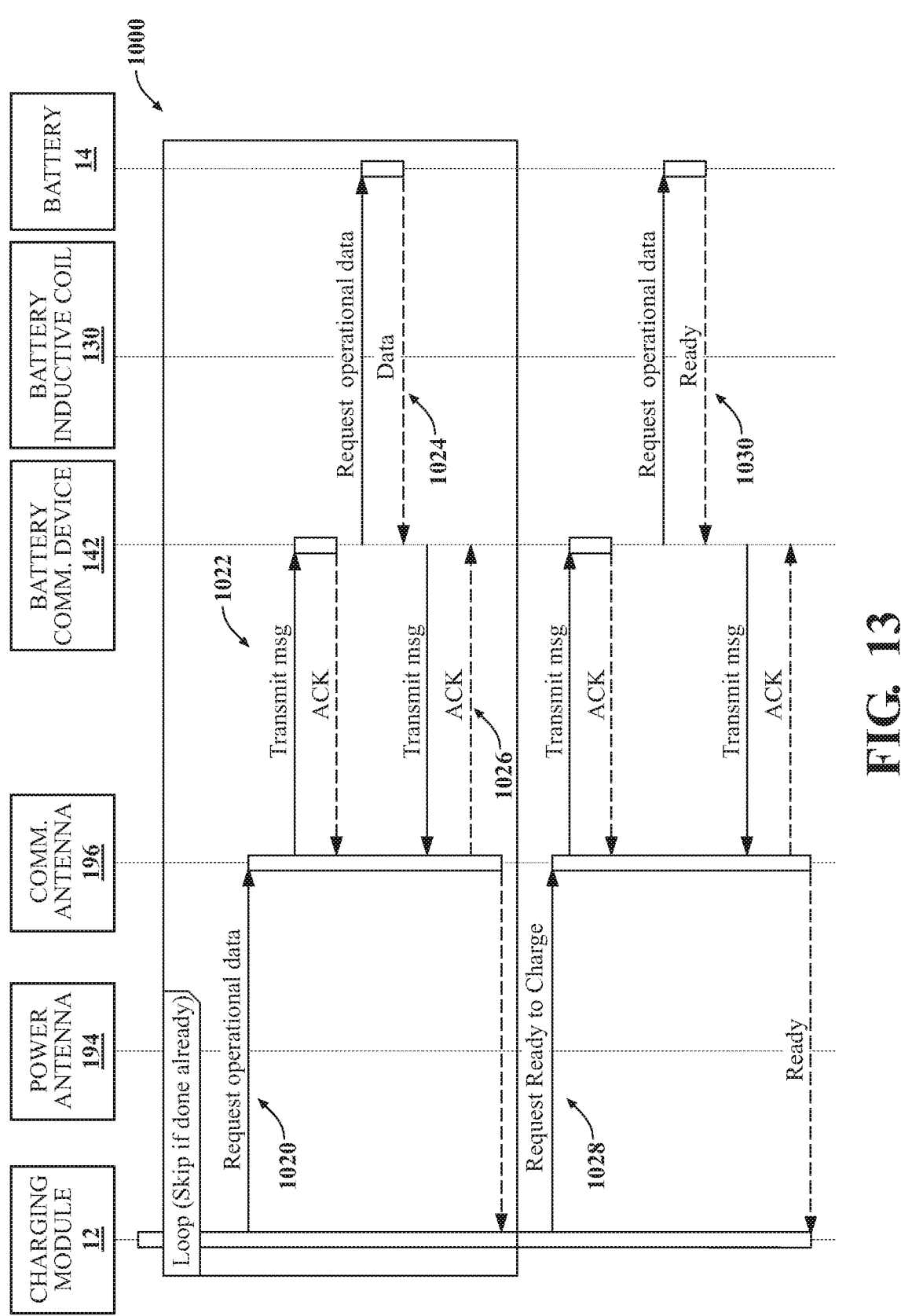
Figure 14:
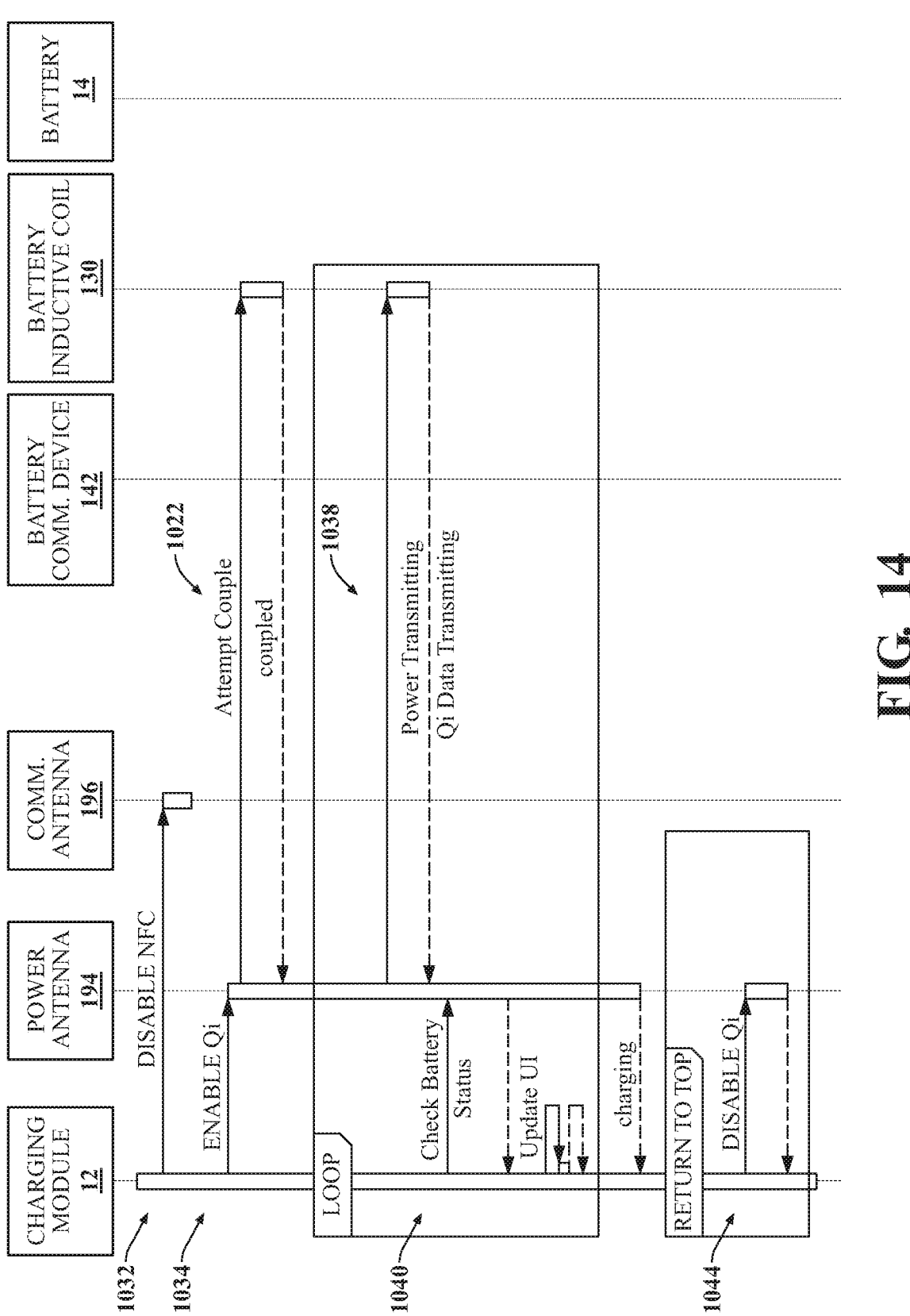

FIGS. 12-14 are flowcharts of an exemplary method 1000 of providing charge to (or "charging") a battery that may be used with the wirelessly chargeable battery 14 and the charging module 16 described herein. In one instance, method 1000 is performed by executing computer-readable instructions stored within one or more memory devices of charging module 16 and/or wirelessly chargeable battery 14. For example, charger controller 200 and/or battery microcontroller 140 may execute instructions stored within memory 206 and/or flash memory 156 to perform the functions of method 1000 described herein.

Referring to FIG. 12, in one instance, charging module 16 enables or activates 1002 communication antenna 196 to detect one or more wirelessly chargeable batteries 14 positioned in proximity to charging module 16. In a specific instance, the communication antenna 196 is activated while power antenna 194 is deactivated. Once communication antenna 196 is activated, charging module 16 enters a discovery mode. During the discovery mode, charging module 16 detects a proximity of a wirelessly chargeable battery 14 when wirelessly chargeable battery 14 is placed proximate to a charging bay 46. For example, when an autoclavable container 12 including a wirelessly chargeable battery 14 is placed onto charging module 16 such that the wirelessly chargeable battery 14 is positioned proximate to a charging bay 46, the wireless communication field generated by communication antenna 196 energizes 1004 a tag 148 within battery communication device 142. Wirelessly chargeable battery 14 may initially be in a low power state in which one or more components of wirelessly chargeable battery 14 (e.g., battery microcontroller 140) are at least partially deactivated. Additionally or alternatively, battery microcontroller 140 may detect when wirelessly chargeable battery 14 is placed in proximity to charging module 16 based on the presence of the electromagnetic field, for example.

In response to tag 148 being energized, a field detection pin or device within tag 148 may be set 1006. In another instance, the field detection pin may be enabled when wirelessly chargeable battery 14 is paired to the charging bay 46 that wirelessly chargeable battery 14 is positioned proximate to as described more fully herein. The setting of the field detection pin 1006 causes wirelessly chargeable battery 14 to exit 1008 the low power state (or "wake up") and enter an operational or full power state in which the components of wirelessly chargeable battery 14 are activated. In one instance, wirelessly chargeable battery 14 draws power from battery cells 126 during the low power state and the full power state until charging power is provided by charging module 16 (e.g., until an electromagnetic field is established by power antenna 194 to provide charging power to wirelessly chargeable battery 14).

As used herein, the low power state may refer to a power state in which at least some portions of wirelessly chargeable battery 14 are disabled and wirelessly chargeable battery 14 consumes less power than in a full power state in which all portions of the battery are enabled. In one instance, battery microcontroller 140 may draw a current of about 20 milliamps (ma) or lower while wirelessly chargeable battery 14 is in the low power state. Alternatively, the low power state may be characterized as a power state in which at least some components of wirelessly chargeable battery 14 are disabled, and portions of battery microcontroller 140 are disabled such that battery microcontroller 140 draws a current that is less than 5% of the current that battery microcontroller 140 draws when wirelessly chargeable battery 14 is in the full power state.

In one instance, when tag 148 is energized by the electromagnetic field generated by communication antenna 196, an antenna within tag 148 or battery communication device 142 transmits a pairing message to communication antenna 196 to cause battery communication device 142 to be paired 1010 with communication antenna 196 (and therefore to pair wirelessly chargeable battery 14 with charging bay 46 and charging module 16). In a specific instance, tag 148 is an NFC tag that enables battery communication device 142 to pair with communication antenna 196 using an NFC protocol in response to the energizing of tag 148 by communication antenna 196. Alternatively, wirelessly chargeable battery 14 may be paired with charging module 16 and/or charging bay 46 using Bluetooth or any other suitable protocol. During the pairing of wirelessly chargeable battery 14 and charging module 16, authentication data may be received from wirelessly chargeable battery 14 to enable charging module 16 to authenticate wirelessly chargeable battery 14. In one instance, the battery authentication data may be stored within tag 148 and may be readable by charger controller 200 via communication antenna 196 to enable charging module 16 to authenticate wirelessly chargeable battery 14. In such a manner, charging module 16 may ensure that only approved wirelessly chargeable batteries 14 are provided with charging power from charging module 16.

In one instance, the wirelessly chargeable battery 14 may exit 1008 the low power state in stages. In a first stage, the energizing 1004 of tag 148 may cause battery communication device 142 to exit the low power state to enable the battery communication device 142 to pair with charging bay 46. In a second stage, in response to the pairing of battery communication device 142 to charging bay 46, the remaining portions of wirelessly chargeable battery 14 (including battery microcontroller 140) may exit 1008 the low power state. Alternatively, the energizing 1004 of tag 148 may cause all portions of wirelessly chargeable battery 14 to exit the low power state at substantially the same time, or any other suitable sequence of exiting the low power state may be performed by wirelessly chargeable battery 14.

In one instance, battery microcontroller 140 may wait a predetermined amount of time (such as 150 milliseconds or another suitable time) after wirelessly chargeable battery 14 has exited 1008 the low power state before moving to the next step of method 1000. After the predetermined amount of time has elapsed, battery microcontroller 140 may reconfigure the field detection pin to place wirelessly chargeable battery 14 in a "pass through" mode 1012. In the pass-through mode 1012, data stored within the tag 148 is transmitted to charging module 16 via communication antenna 196, and data may also be transmitted from charging module 16 to tag 148. It should be recognized that data stored within tag 148 may be readable by charging module 16 even if battery microcontroller 140 is inactive, in a low power state, damaged, or is otherwise unable to communicate with charging module 16 and/or tag 148.

Once the tag 148 is paired and the pass through mode is set 1012, charging module 16 begins receiving 1014 data relating to the battery state (hereinafter referred to as "battery state data") from wirelessly chargeable battery 14. In one instance, charging module 16 transmits one or more messages to battery communication device 142 via communication antenna 196 to request the battery state data from battery microcontroller 140. Battery microcontroller 140 receives the messages from battery communication device 142 and provides 1016 the battery state data in response. In one instance, battery microcontroller 140 temporarily stores the battery state data in tag 148 in preparation for transmission to charging module 16. Charging module 16 may then read the battery state data directly from tag 148 and may store the battery state data in memory 206 of charging module 16.

The battery state data may include a state of charge, a state of health, and/or any other suitable data of wirelessly chargeable battery 14. The state of charge may include data representing an amount of capacity of wirelessly chargeable battery 14 and a present charge level of wirelessly chargeable battery 14 or an amount of charge needed to reach a fully charged state of wirelessly chargeable battery 14.

In a specific instance, battery microcontroller 140 may store the battery state data in tag 148 in predetermined blocks of data that are transmitted to charging module 16. As each block of data is transmitted to charging module 16, charger controller 200 transmits an acknowledgement message or signal to battery microcontroller 140 via communication antenna 196 to confirm successful receipt of the block of data. In a particular instance, each block of data is 64 bytes. Alternatively, each block of data may include any suitable number of bytes.

After charging module 16 has received the battery state data, charging module 16 may update 1018 the display to reflect the data received. For example, charger controller 200 may transmit a command or signal to display area 202 to cause a state of charge indicator to reflect the present state of charge of wirelessly chargeable battery 14 and to cause a state of health indicator to reflect the present state of health of wirelessly chargeable battery 14 based on the data received.

Referring to FIG. 13, after the battery state data has been received and display area 202 has been updated, charging module 16 may request 1020 battery operational data from wirelessly chargeable battery 14. In one instance, the battery operational data may include the data stored within the data structure 168 as described above with reference to FIG. 10. Additionally or alternatively, any other suitable data may be requested and received by charging module 16. Charger controller 200 may transmit a signal or request to communication antenna 196 to receive the battery operational data. Communication antenna 196 may transmit 1022 the signal or request to battery communication device 142 which in turn transmits a signal or request to battery microcontroller 140. In response to receiving the signal or request, battery microcontroller 140 may store the battery operational data in tag 148 of battery communication device 142 in preparation for transmission to charging module 16.

In a specific instance, battery microcontroller 140 may store 1024 the battery operational data in tag 148 in predetermined blocks of data that are transmitted to charging module 16. In a similar manner as described above, as each block of data is transmitted 1026 to charging module 16, charger controller 200 transmits an acknowledgement message or signal to battery microcontroller 140 via communication antenna 196 to confirm successful receipt of the block of data. In a particular instance, each block of data is 64 bytes. Alternatively, each block of data may include any suitable number of bytes. Charging module 16 may continually request additional blocks of battery operational data until battery microcontroller 140 transmits a message indicating that the transmission of the battery operational data is complete. Alternatively, charging module 16 may continually request additional blocks of battery operational data until a predetermined amount of the battery operational data has been received by charging module 16. In one instance, the predetermined amount of battery operational data includes 3 kilobytes of data. In another instance, the predetermined amount of battery operational data includes a size of the data structure 168 (i.e., the amount of data able to be stored within data structure 168).

After the transmission of the battery operational data is complete, charging module 16 may transmit 1028 a message to battery microcontroller 140 requesting that the battery microcontroller 140 respond that it is ready to begin receiving charging power from the charging module 16. This request may be referred to as a "ready to charge request". When battery microcontroller 140 receives the ready to charge request, battery microcontroller 140 may determine whether one or more battery parameters are within an acceptable range. For example, battery microcontroller 140 may determine whether a voltage output from cells 126 is within an acceptable range. If battery microcontroller 140 determines that the battery parameters are within the acceptable range, battery microcontroller 140 may transmit 1030 a message back to charging module 16 indicating that wirelessly chargeable battery 14 is ready to receive charging power. This message may be referred to as a "ready to charge confirmation". The ready to charge confirmation message may also serve as a notification to charger controller 200 that wirelessly chargeable battery 14 (and its components) has exited the low power state and is in a full power state. Battery microcontroller 140 may also disable or deactivate battery communication device 142 in preparation for receiving charging power. For example, battery microcontroller 140 may receive a signal or message from charger controller 200 that charging module 16 is switching to a power delivery state or is otherwise preparing to provide the charging power to wirelessly chargeable battery 14. When charging module 16 receives the ready to charge confirmation, charging module 16 begins providing charging power to wirelessly chargeable battery 14 as described with reference to FIG. 14. However, if battery microcontroller 140 does not transmit the ready to charge confirmation, or instead transmits an error message due to one or more battery parameters being outside of the acceptable range, charging module 16 may prevent the delivery of power to wirelessly chargeable battery 14 and method 1000 may end.

In one instance, the error message may be generated by battery microcontroller 140 in response to a self-diagnosis procedure or other test executed by battery microcontroller 140. For example, battery microcontroller 140 may receive sensor signals representative of one or more parameters of wirelessly chargeable battery 14 and may compare the sensor signals to predetermined thresholds or usage criteria to determine if wirelessly chargeable battery 14 is operating correctly or is otherwise in an acceptable state of health. The error message may be transmitted by battery microcontroller 140 via battery communication device 142 and may be received by charging module 16 via communication antenna 196. The error message may be reflected in a state of health indicator of charging module 16. For example, a state of health indicator may indicate that wirelessly chargeable battery 14 has an error or is otherwise in an unacceptable state for charging and should be replaced. A state of health indicator may display an indication that wirelessly chargeable battery 14 should be replaced by displaying text, a graphic, and/or a light having a predetermined color to indicate that replacement is suggested.

Referring to FIG. 14, charging module 16 begins the process of providing charging power to wirelessly chargeable battery 14 by disabling or deactivating 1032 communication antenna 196 (e.g., by removing power to communication antenna 196) and enabling or activating 1034 power antenna 194 (e.g., by providing power to power antenna 194). Charger controller 200 then attempts to inductively couple 1036 power antenna 194 to battery induction coil 130 to transmit charging power to wirelessly chargeable battery 14. In one instance, charger controller 200 executes the Wireless Power Consortium (Qi) wireless charging protocol to inductively couple 1036 power antenna 194 to battery induction coil 130 to provide the charging power to wirelessly chargeable battery 14. Alternatively, charger controller 200 may execute any other suitable protocol to provide wireless charging power to wirelessly chargeable battery 14 via power antenna 194 and battery induction coil 130.

After the power antenna 194 and the battery induction coil 130 are inductively coupled, charging power is wirelessly provided 1038 from charging module 16 to wirelessly chargeable battery 14 via the respective antennas. In one instance, charger controller 200 operates the charging process in a loop in which charging power is provided for a predetermined amount of time. In an instance, the predetermined amount of time is 2 minutes. Alternatively, the predetermined amount of time is 30 seconds or any other suitable amount of time. During the charging process loop, charger controller 200 periodically transmits 1040 a request to wirelessly chargeable battery 14 to receive the battery state of charge data. Battery microcontroller 140 receives the request and transmits a response message to charger controller 200 containing the present state of charge of wirelessly chargeable battery 14. Charger controller 200 may then update 1042 display area 202, such as by updating a state of charge indicator, to reflect the present state of charge of wirelessly chargeable battery 14. If charger controller 200 determines that wirelessly chargeable battery 14 has not yet reached a full state of charge, charger controller 200 may continue the charging process loop until the predetermined amount of time has elapsed. After charging power 1038 has been provided for the predetermined amount of time, charger controller 200 disables or deactivates 1044 power antenna 194 and returns to the beginning of method 1000 (i.e., step 1002). In such a manner, charger controller 200 causes method 1000 to be executed in a loop until wirelessly chargeable battery 14 has reached a full state of charge. Alternatively, charger controller 200 may continually provide charging power 1038 to wirelessly chargeable battery 14 until wirelessly chargeable battery 14 is fully charged, without periodically returning to the top of method 1000.

If, during execution of the charging loop, charger controller 200 determines that wirelessly chargeable battery 14 has reached a full state of charge, charger controller 200 may update display area 202 to reflect the completed charging of wirelessly chargeable battery 14 (e.g., by causing a state of charge indicator to be illuminated with a particular color such as green or blue). Charger controller 200 then stops providing charging power to wirelessly chargeable battery 14 and disables or deactivates 1044 power antenna 194. Wirelessly chargeable battery 14 may then be removed from charging bay 46 and/or autoclavable container 12 and may be used as desired.

During the charging process, wirelessly chargeable battery 14 may visually indicate the state of charge and/or state of health in addition to charging module 16 displaying the state of charge and state of health on the charging module display area 202. For example, battery microcontroller 140 may be coupled to one or more LEDs, such as the battery status indicator. Battery microcontroller 140 may cause the battery status indicator to emit a first color of light (such as blue) when wirelessly chargeable battery 14 is not fully charged and may cause the battery status indicator to emit a second color of light (such as green) when battery is fully charged. Battery microcontroller 140 may cause the battery status indicator to emit a third color of light (such as red) if the battery state of health indicates an error or an unacceptable level of health or degradation. In instances where the housing 108 is at least partially transparent, the emission of light from the battery status indicator may be visible to a user when wirelessly chargeable battery 14 is microbially sealed within container 12.

While method 1000 has been described herein as operating with only power antenna 194 or communication antenna 196 being activated at one time, it should be recognized that both power antenna 194 and communication antenna 196 may be activated concurrently such that power is applied to each antenna at the same time. In such an instance, charger controller 200 may use either antenna independently of the other such that data is only transmitted through one antenna at a time. Alternatively, charger controller 200 may operate both power antenna 194 and communication antenna 196 concurrently such that charger controller 200 transmits and/or receives data and/or power using both antennas at the same time.

Figure 15:
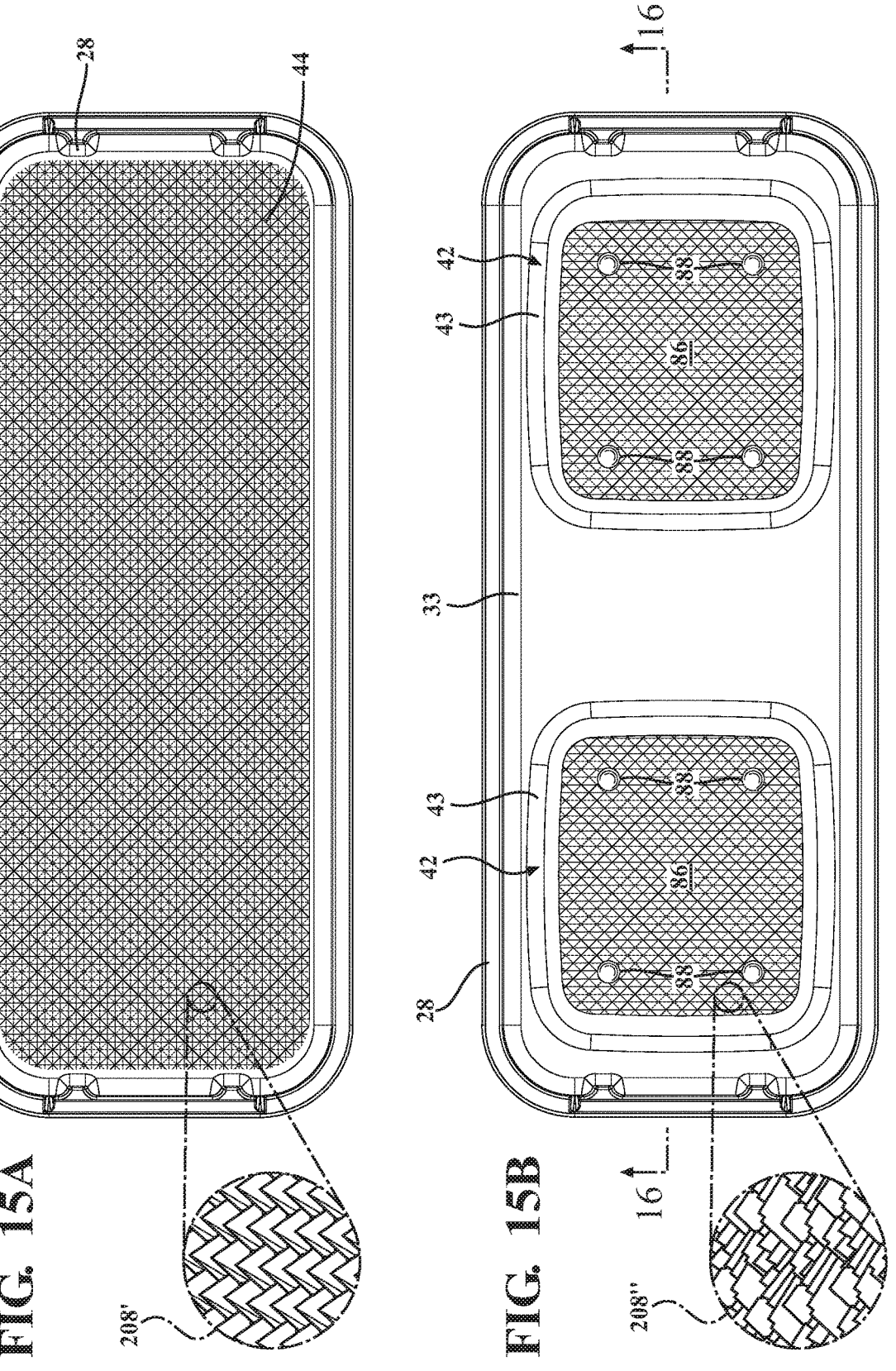
FIGS. 15A and 15B are top views of two instances of a textured inner surface of a base of an autoclavable container.

A base 28 for an autoclavable container 12 for a more effective sterilization process is disclosed. The base allows for more effectively eliminating germs and for improving drying properties during sterilization by including a textured surface. As shown in FIG. 15A the base 28 may include an inner surface 33 textured with a texture 208' for improving drying properties (herein, an inner surface 33 textured with a texture may be referred to as a textured inner surface 33). The textured inner surface 33 may be hydrophilic and exhibit a water contact angle of less than 90 degrees. As will be discussed further herein, the hydrophilic nature of a textured surface of the base 28 allows for a more effective sterilization process.

Any suitable base 28 for the autoclavable container 12 may include a textured surface for improving drying properties. For example, the base 28 in FIG. 15B optionally includes receptacles 42, such that the inner surface 33 includes the floors 86 and walls 43 of the receptacles 42. In the instance of FIG. 15B, the floors 86 of the receptacles also are textured with a texture 208" (herein, a floor 86 textured with a texture may be referred to as a textured floor 86). As such, the textured surface for improving drying properties of the base 28 in FIG. 15B includes the textured inner surface 33, which includes the textured floors 86. Other instances of the base 28 contemplated herein, but not illustrated by FIGS. 15A and 15B, may also include a suitable textured surface.

Figures 16, 17A, 17B:
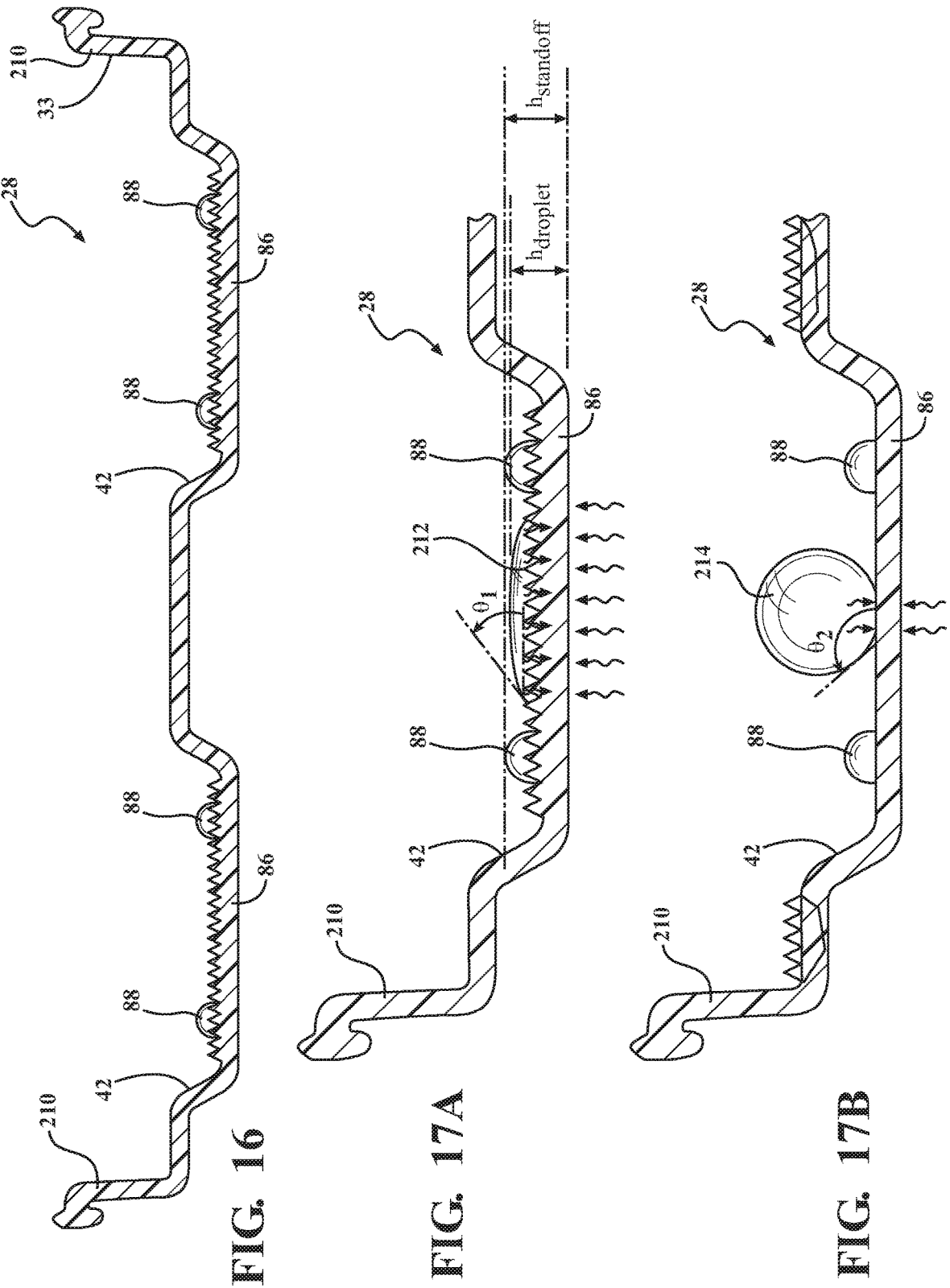
FIG. 16 is a side cutaway view of the textured inner surface of the base of FIG. 15B.
FIG. 17A is a partial side cutaway view of the textured inner surface of the base of FIG. 15B with a water droplet disposed on the base.
FIG. 17B is a partial side cutaway view an untextured inner surface of a base of an autoclavable container with a water droplet disposed on the base.

FIG. 16 illustrates a side view of the base 28 of FIG. 15B. As shown, the inner surface 33 of the receptacle, including the floors 86, are textured with the texture 208". In other instances, any element of the base 28 may be textured or un-textured. For example, in other instances, the outer surface 29 of the base 28, walls 210 of the inner surface 33, the walls 43 of the receptacles 42, and the standoffs 88 may be textured. In another example, only the floor 86 may be textured. In still another example, only the floor 86 may be un-textured. In some instances, other elements of the autoclavable container 12 may include a textured surface. For example, the outer surface 27 and/or the inner surface 31 of lid 26 may be textured.

FIGS. 17A and 17B illustrate how the hydrophilic nature of a textured surface allow for a more effective sterilization process. In FIG. 17A, a water droplet 212 is disposed on a textured surface, the textured floor 86 of the base 28 of FIG. 15B. In FIG. 17B, a water droplet 214 is disposed on an un-textured surface, an un-textured floor 86. As shown, the water droplet 212 forms a contact angle $\theta_1$ is less than 90 degrees with the textured floor 86 that is less than 90 degrees, such that the textured floor 86 is hydrophilic. In contrast, the water droplet 214 forms a contact angle $\theta_2$ with the un-textured floor 86 that is greater than 90 degrees, such that the un-textured floor 86 is hydrophobic. Because the contact angle $\theta_1$ is less than 90 degrees and the contact angle $\theta_2$ is greater than 90 degrees, an amount of the water droplet 212 in contact with the textured floor 86 is greater than an amount of the water droplet 214 in contact with the un-textured floor 86. In other instances, the textured surface of the base 28 may be hydrophilic and the contact angle $\theta_1$ between a water droplet and the textured surface may be less than 80 degrees, 70 degrees, 60 degrees, 50 degrees, 40 degrees, 30 degrees, 20 degrees, or 10 degrees.

During an autoclave process, the autoclavable container 12 first enters a sterilization phase. During the sterilization phase, sterilant permeates the autoclavable container 12 and condenses onto the inner surface 33 and/or the floor 86 of the base 28. For example, during an autoclave process that uses steam as the sterilant, the steam condenses as high-temperature water droplets onto the inner surface 33 and/or floor 86 of the base 28. As previously stated, an amount of contact between a water droplet and a textured surface is greater than an amount of contact between a water droplet and an un-textured surface. As such, a high-temperature water droplet contacting a textured surface conducts more heat to the inner surface 33, eliminating more bacteria on the inner surface 33. This phenomenon is illustrated in FIGS. 17A and 17B, where a greater amount of heat is conducted to the inner surface 33 from the water droplet 212 than is conducted to the inner surface 33 from the water droplet 214.

After the sterilization phase, the autoclavable container 12 then enters a drying phase. During the drying phase, a temperature of the base 28 increases, conducting heat to the inner surface 33 of the base 28 to evaporate the water droplets from the sterilization phase. As previously stated, an amount of contact between a water droplet and a textured surface is greater than an amount of contact between a water droplet and an un-textured surface. As such, as the temperature of the base 28 increases, more heat is conducted to a water droplet on a textured surface, causing the water droplet to dry faster. This phenomenon is illustrated in FIGS. 17A and 17B, where a greater amount of heat is conducted to the water droplet 212 from the base 28 than is conducted to the water droplet 214 from the base 28.

The textured surface of the base 28 may include any suitable texture such that the textured surface is hydrophilic, and the textured surface exhibits a water contact angle less than 90 degrees. For example, the texture 208' in FIG. 15A includes pyramidal peaks of uniform size and uniform spacing. The texture 208" in FIG. 15B includes pyramidal peaks of variable size and variable spacing. In other instances, the texture may include peaks of any suitable shape, and with uniform or variable size and spacing. For instance, the textured surface of the base 28 may be textured with a texture that includes hemispherical peaks of uniform size and variable spacing.

The height of the standoffs 88, illustrated as $h_{standoff}$ in FIGS. 17A and 17B, may be based on the textured surface. As previously stated, $h_{standoff}$ may be minimized in order to maximize efficiency of the charging power transfer between the power antenna 194 and the induction coil 130, while still allowing sterilant to contact the bottom surface of the wirelessly chargeable battery 14. Additionally, $h_{standoff}$ may be chosen such that a water droplet disposed on the textured surface does not contact the bottom surface of the wirelessly chargeable battery 14 to facilitate proper sterilization of and proper drying of the wirelessly chargeable battery 14 and the autoclavable container 12. As such, $h_{standoff}$ may be chosen such that a height of the water droplet $h_{droplet}$ is less than $h_{standoff}$ as shown in FIG. 17A. In one such instance, $h_{standoff}$ may be no greater than 4 millimeters such that a water droplet disposed on the textured surface does not contact the bottom surface of the wirelessly chargeable battery 14, while allowing sterilant to contact the bottom surface of the wirelessly chargeable battery 14 and preserving an efficiency of charging power transfer of greater than 10%, 25%, 50%, 75%, or 90%.

Figures 18A, 18B, 18C, 18D:
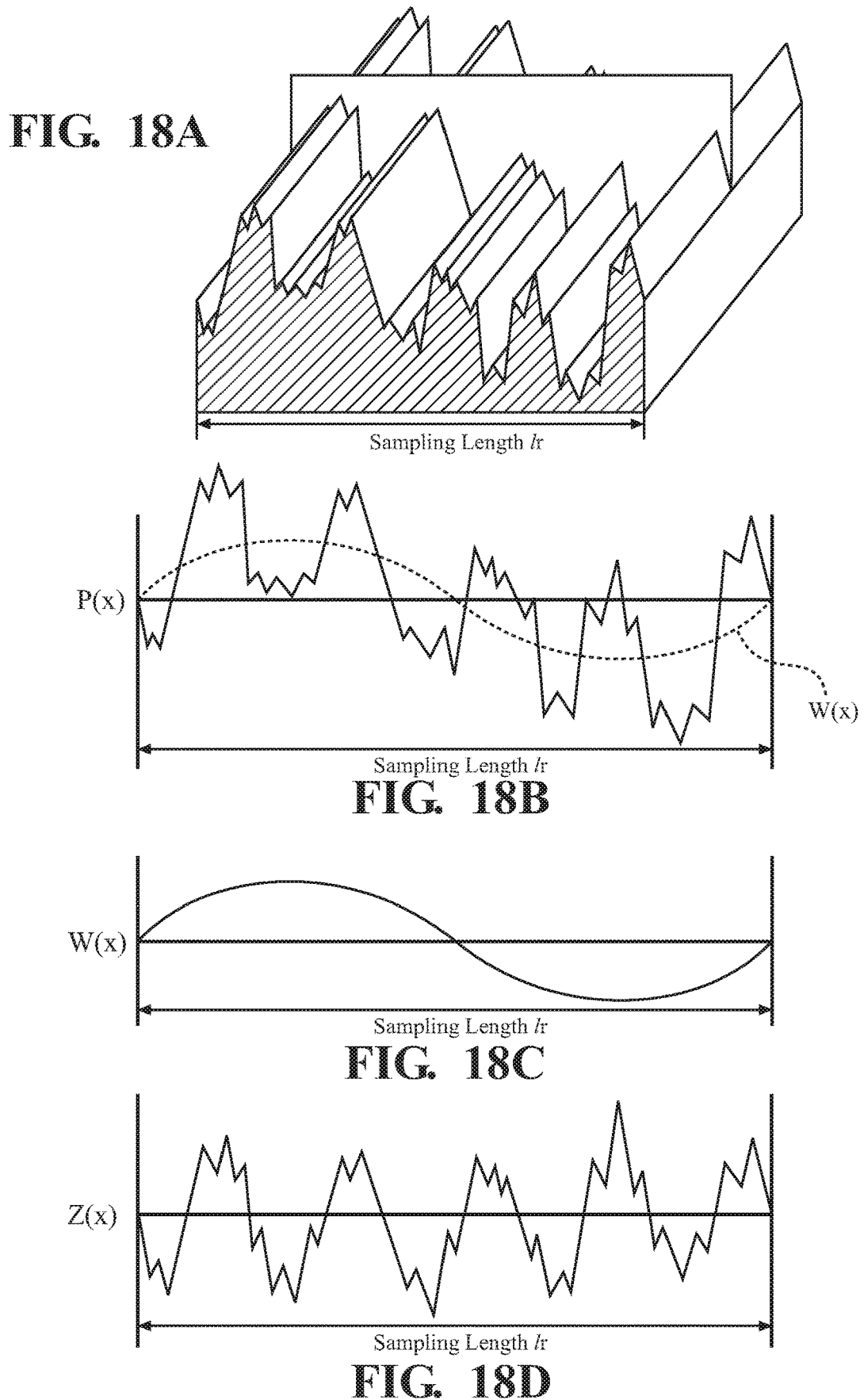
FIG. 18A is a partial side view of an example texture of a textured surface.
FIG. 18B is a plot of the example texture of a textured surface.
FIG. 18C is a plot of a waviness of the example texture of a textured surface.
FIG. 18D is a plot of a roughness of the example texture of a textured surface.

In addition to shape and variable or uniform size and spacing, the texture of the textured surface may also be defined using a roughness profile. An example texture is shown in FIG. 18A. The texture of the textured surface is captured in FIG. 18B using a texture profile P(x). As shown, the texture profile P(x) captures smaller peaks and valleys of the texture, as well as larger curvatures of the texture. In the interest of analyzing the smaller peaks and valleys of the texture, it is advantageous to remove the larger curvatures captured by the texture profile P(x). The larger curvatures of the texture are captured using a waviness profile W(x), shown in FIG. 18C. To remove the larger curvatures, the waviness profile W(x) is filtered from the texture profile P(x), outputting the roughness profile Z(x), shown in FIG. 18D.

The roughness profile Z(x) allows the texture of the textured surface to be defined using a variety of parameters. Three example parameters are shown in FIGS. 18E-18G. Each of the example parameters reference a mean line 216, which is defined such that an area between the roughness profile R(x) and the mean line 216 above the mean line 216 is equal to an area between the roughness profile R(x) and the mean line 216 below the mean line 216. Additionally, each roughness profile Z(x) is analyzed over a sampling length $l_r$.

In FIG. 18E, an arithmetical mean height $R_a$ is used to define the roughness profile Z(x). The arithmetical mean height $R_a$ is defined as an average absolute value of the difference between the roughness profile Z(x) and the mean line 216 over the sampling length $l_r$. The arithmetical mean height $R_a$ of the roughness profile Z(x) may be any suitable value such that the textured surface may be hydrophilic and exhibit a water contact angle less than 90 degrees. For example, the arithmetical mean height $R_a$ may be greater than 2 micrometers and less than 4 micrometers.

In FIG. 18F, a root mean square deviation $R_q$ is used to define the roughness profile Z(x). The root mean square deviation $R_q$ is defined as a root mean square of the difference between the roughness profile Z(x) and the mean line 216 over the sampling length $l_r$. The root mean square deviation $R_q$ of the roughness profile Z(x) may be any suitable value such that the textured surface may be hydrophilic and exhibit a water contact angle less than 90 degrees. For example, the arithmetical mean height $R_a$ may be greater than 2 micrometers and less than 5 micrometers.

In FIG. 18G, a mean width of profile elements $RS_m$ is used to define the roughness profile Z(x). The mean width of profile elements $RS_m$ is defined as an average value of the length of profile elements over the sampling length $l_r$. The profile elements are illustrated in FIG. 18G as $X_{s1}$, $X_{s2}$, $X_{s3}$, $X_{si}$, and $X_{sm}$. The mean width of profile elements $RS_m$ may be any suitable value such that the textured surface may be hydrophilic and exhibit a water contact angle less than 90 degrees. For example, the mean width of profile elements $RS_m$ may be greater than 10 micrometers and less than 40 micrometers.

Other parameters not shown in the figures may also be used to define the roughness profile Z(x). For example, a maximum height of the profile $R_z$ is defined as a maximum peak-to-peak height of the roughness profile Z(x). The maximum height of the profile $R_z$ of the roughness profile Z(x) may be any suitable value such that the textured surface may be hydrophilic and exhibit a water contact angle less than 90 degrees. For example, the maximum height of the profile $R_z$ may be greater than 20 micrometers and less than 30 micrometers.

The base 28 including a textured surface may be manufactured using a variety of methods. For example, the base 28 may be molded from a polymeric material permitting the transmission of an electromagnetic wave therethrough and having a glass transition temperature above 140 degrees Celsius. The base 28 may be molded such that an inner surface of the base 28 exhibits a contact angle less than 90 degrees. In another example, the base 28 may be molded from the polymeric material, but the base 28 may be textured after being molded. For example, after the base 28 is molded from the polymeric material, the base 28 may be textured with a laser.

CLAUSES

I. An autoclavable wirelessly chargeable battery comprising:
   a housing;
   a cell disposed within said housing;
   a ferrite base disposed between said cell and said housing;
   an induction coil disposed on said ferrite base, said induction coil being configured to receive electromagnetic waves;
   a radiofrequency coil disposed on said ferrite base, said radiofrequency coil being configured to receive radiofrequency signals;
   a microcontroller disposed between said housing and said cell and coupled to said induction coil and said radiofrequency coil; and
   a thermally insulative material at least partially disposed between said cell and said ferrite base.

II. The autoclavable wirelessly chargeable battery of clause I, wherein the autoclavable wirelessly chargeable battery includes a second thermally insulative material at least partially disposed between said cell and said housing.

III. The autoclavable wirelessly chargeable battery of any preceding clause, wherein said housing includes a top portion and a bottom portion, wherein said top portion and said bottom portion are configured to be coupled.

IV. The autoclavable wirelessly chargeable battery of clause III, wherein said microcontroller is disposed above said cell and below said top portion of said housing.

V. The autoclavable wirelessly chargeable battery of any preceding clause, wherein said thermally insulative material is disposed above said cell and below said microcontroller.

VI. The autoclavable wirelessly chargeable battery of clause II, wherein said second thermally insulative material is disposed below said cell and above said ferrite base.

VII. The autoclavable wirelessly chargeable battery of any preceding clause, aid thermally insulative material having a thermal conductivity less than 30 mW/(m*K) at 298 Kelvin.

VIII. The autoclavable wirelessly chargeable battery of any preceding clause, wherein said thermally insulative material comprises an aerogel.

IX. The autoclavable wirelessly chargeable battery of clause II, said second thermally insulative material having a thermal conductivity less than 30 mW/(m*K) at 298 Kelvin.

X. The autoclavable wirelessly chargeable battery of clause II, wherein said second thermally insulative material comprises an aerogel.

XI. An autoclavable wirelessly chargeable battery comprising:

a housing;

a cell disposed within said housing;

a thermally insulative material at least partially disposed between said housing and said cell;

a ferrite base disposed between said cell and said housing;

an induction coil disposed on said ferrite base, said induction coil being configured to receive electromagnetic waves;

a radiofrequency coil disposed on said ferrite base, said radiofrequency coil being configured to receive radiofrequency signals;

wherein said ferrite base is a monolithic component and said radiofrequency coil and said induction coil share said ferrite base; and a microcontroller disposed between said housing and said cell and coupled to said induction coil and said radiofrequency coil.

XII. The autoclavable wirelessly chargeable battery of clause XI, wherein said induction coil and said radiofrequency coil are concentrically disposed on said ferrite base.

XIII. The autoclavable wirelessly chargeable battery of any one of clauses XI and XII, wherein said induction coil and said radiofrequency coil are concentrically disposed on said ferrite base such that said induction coil is disposed within said radiofrequency coil.

XIV. The autoclavable wirelessly chargeable battery of any one of clauses XI-XIII, wherein said induction coil and said radiofrequency coil are disposed on said ferrite base such that said induction coil and said radiofrequency coil are coplanar.

XV. The autoclavable wirelessly chargeable battery of clauses XI-XIV, wherein said induction coil comprises a temperature rating of at least 155 degrees Celsius.

XVI. The autoclavable wirelessly chargeable battery of clauses XI-XV, wherein said ferrite base comprises a relative permeability of at least 700.

XVII. The autoclavable wirelessly chargeable battery of clauses XI-XVI, wherein said ferrite base comprises a Q factor of at least 20.

XVIII. An autoclavable wirelessly chargeable battery comprising:

a housing;

a cell disposed within said housing;

a thermally insulative material at least partially disposed between said housing and said cell;

a ferrite base disposed between said cell and said housing;

an induction coil disposed on said ferrite base, said induction coil being configured to receive electromagnetic waves;

a radiofrequency coil embedded in a medium of a flexible printed circuit board such that adjacent windings of said radiofrequency coil are fixed relative to one another by said medium of said flexible printed circuit board, said flexible printed circuit board being disposed on said ferrite base, said radiofrequency coil being configured to receive radiofrequency signals;

wherein said ferrite base is a monolithic component and said radiofrequency coil and said induction coil share said ferrite base; and a microcontroller disposed between said housing and said cell and coupled to said induction coil and said radiofrequency coil.

XIX. The autoclavable wirelessly chargeable battery of clause XVIII, wherein said medium of said flexible printed circuit board comprises a resin.

XX. A polymeric autoclavable container for sterilization having improved drying properties, the autoclavable container comprising:

a lid; and a base comprising a polymeric material permitting transmission of an electromagnetic wave therethrough and having a glass transition temperature above 140 degrees Celsius, said base having an inner surface which is hydrophilic;

wherein at least one of said base and said lid define a plurality of apertures configured to allow a sterilant to permeate the autoclavable container.

XXI. A method of manufacturing a base for an autoclavable container, the method comprising:

molding the base for an autoclavable container from a polymeric material permitting transmission of an electromagnetic wave therethrough and having a glass transition temperature above 140 degrees Celsius such that an inner surface exhibits a contact angle less than 45 degrees.

XXII. The method of clause XXI, wherein the inner surface exhibits a water contact angle of less than 80 degrees.

XXIII. The method of any one of clauses XXI and XXII, wherein the inner surface exhibits a water contact angle of less than 70 degrees.

XXIV. The method of any one of clauses XX-XXIII, wherein the inner surface exhibits a water contact angle of less than 60 degrees.

XXV. A method of manufacturing a base for an autoclavable container, the method comprising:

molding the base for an autoclavable container from a polymeric material permitting transmission of an electromagnetic wave therethrough and having a glass transition temperature above 140 degrees Celsius; and texturing the molded base such that an inner surface of the base exhibits a water contact angle of less than 45 degrees.

XXVI. The method of clause XXV, wherein the step of texturing the molded base further includes a step of texturing a floor of the base using laser texturing.

XXVII. A wirelessly chargeable battery comprising:

an antenna configured to receive an electromagnetic wave; and a housing comprising an alignment feature configured to align said wirelessly chargeable battery within an autoclavable container configured to receive said wirelessly chargeable battery such that said antenna is aligned with an induction coil of a wireless charging device when the autoclavable container is disposed on the wireless charging device.

XXVIII. An autoclavable container for sterilizing a wirelessly chargeable battery, the autoclavable container comprising:

a base comprising a polymeric material permitting transmission of an electromagnetic wave therethrough and having a glass transition temperature above 140 degrees Celsius, wherein said base defines a receptacle shaped to receive a wirelessly chargeable battery comprising an antenna configured to receive an electromagnetic wave, wherein said base comprises an alignment feature configured to align the wirelessly chargeable battery within said receptacle such that the antenna of the wirelessly chargeable battery and an induction coil of a wireless charging device are aligned when said receptacle receives the wirelessly chargeable battery and said autoclavable container is disposed on the wireless charging device.

XXIX. An autoclavable container for sterilizing a wirelessly chargeable battery, the autoclavable container comprising:

a lid; and a base defining a receptacle shaped to receive a wirelessly chargeable battery;

wherein:

one of said base and said lid define a plurality of apertures configured to allow a sterilant to permeate said autoclavable container;

said receptacle comprises a floor and a standoff extending from said floor such that the wirelessly chargeable battery received by said receptacle is disposed on said standoff and a bottom surface of the wirelessly chargeable battery is spaced from said floor to allow circulation of a sterilant underneath the wirelessly chargeable battery such that a majority of the bottom surface is exposed to the sterilant; and said floor of said receptacle comprises a textured surface exhibiting a water contact angle of less than 45 degrees.

Although specific features of various instances of the disclosure may be shown in some drawings and not in others, this is for convenience only. In accordance with the principles of the disclosure, any feature of a drawing or other instance may be referenced and/or claimed in combination with any feature of any other drawing or instance.

In some implementations of the autoclavable container 12, the lid 26 does not include metal. For example, lid may include a polymeric material or a material other than metal that still facilitates drying of contents thereof by retaining heat from the autoclave.

In some implementations of the autoclavable container 12, the base 28 does not include a polymeric material. For example, the base 28 may include non-polymeric materials such as metal or glass.

In some implementations of the autoclavable container 12, the base 28 need not include a plurality of protrusions and/or receptacles. For example, the base 28 may include one protrusion and receptacle. The base 28 may also be free of protrusions and/or receptacles.

In some implementations of the autoclavable container 12, one of the base 28 and the lid 26 define a plurality of apertures configured to allow a sterilant to permeate the autoclavable container 12.

In some implementations, the autoclavable container 12 may sterilize surgical instruments other than wirelessly chargeable batteries 14. or instance, the methods described herein may be used to sterilize manual surgical instruments, such as scalpels, forceps and osteo-tomes. The methods described herein may also be used to sterilize powered surgical instruments, such as rotary handpieces, drills, or endoscopes.

This written description uses examples to describe instances of the disclosure and also to enable any person skilled in the art to practice the instances, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for sterilizing a wirelessly chargeable battery, the system comprising:

a wirelessly chargeable battery comprising a bottom surface; and a container configured to receive the wirelessly chargeable battery and configured to be placed on a charging module adapted to transfer power to the wirelessly chargeable battery for charging the wirelessly chargeable battery when the wirelessly chargeable battery is received by the container, the container comprising:

a lid, the lid comprising a mount configured to receive a filter defining a microbial barrier; and a base comprising a polymeric material permitting transmission of an electromagnetic wave therethrough and having a glass transition temperature above 140 degrees Celsius, the base defining a receptacle being shaped to receive a wirelessly chargeable battery, wherein one of the lid and the base defining a plurality of apertures configured to allow a sterilant to permeate the lid or base;

wherein the receptacle comprises a floor and a standoff extending from the floor such that the wirelessly chargeable battery received by the receptacle is disposed on the standoff and the bottom surface of the wirelessly chargeable battery is spaced from the floor to allow circulation of a sterilant underneath the wirelessly chargeable battery such that a majority of the bottom surface is exposed to the sterilant, the floor having a textured surface exhibiting a water contact angle of less than 45 degrees, and wherein a height of the standoff is no greater than 4 millimeters such that:

the height of the standoff prevents a water droplet disposed on the floor of the receptacle from contacting the bottom surface of the wirelessly chargeable battery, and the height of the standoff permits transmission of electromagnetic waves from the charging module to the wirelessly chargeable battery with an efficiency greater than 50%.

2. The system of claim 1, comprising at least three standoffs, the bottom surface of the wirelessly chargeable battery contacting the at least three standoffs when the wirelessly chargeable battery is received by the receptacle.

3. The system of claim 1, wherein the majority of the bottom surface comprises at least 50% of the bottom surface.

4. The system of claim 1, wherein the majority of the bottom surface comprises at least 75% of the bottom surface.

5. The system of claim 1, wherein the majority of the bottom surface comprises at least 90% of the bottom surface.

6. The system of claim 1, wherein the lid comprises metal having a thermal conductivity greater than 1 W/(m*K) at 298 Kelvin such that the lid is configured to retain heat to facilitate drying of contents thereof after the container is removed from a sterilizer.

7. The system of claim 1, wherein the lid comprises a thermal conductivity of greater than 10 W/(m*K) at 298 Kelvin.

8. The system of claim 1, wherein the height of the standoff is selected to allow sterilant to contact the bottom surface of the wirelessly chargeable battery.

9. The system of claim 1, wherein the standoff is integrally formed with the receptacle.

10. The system of claim 1, wherein the textured surface comprises a roughness profile comprising an arithmetical mean height (Ra) greater than 2 micrometers and less than 4 micrometers.

11. The system of claim 1, wherein the textured surface comprises a roughness profile comprising a maximum height (Rz) greater than 20 micrometers and less than 30 micrometers.

* * * * *